United States Patent [19]
Ohashi et al.

[11] Patent Number: 5,723,497
[45] Date of Patent: Mar. 3, 1998

[54] AMINE DERIVATIVE AND DERMATOLOGIC PREPARATION CONTAINING THE SAME

[75] Inventors: Yukihiro Ohashi, Utsunomiya; Yukihiro Yada, Haga-gun; Yoshinori Takema, Haga-gun; Taketoshi Fujimori, Haga-gun; Akira Kawamata, Utsunomiya; Hiroyuki Ohsu; Kazuhiko Higuchi, both of Haga-gun; Genji Imokawa, Utsunomiya; Hiroshi Kusuoku, Haga-gun; Ayumi Ogawa, Haga-gun; Tsutomu Fujimura, Haga-gun, all of Japan

[73] Assignee: Kao Corporation, Tokyo, Japan

[21] Appl. No.: 513,872

[22] PCT Filed: Mar. 17, 1994

[86] PCT No.: PCT/JP94/00436

§ 371 Date: Sep. 18, 1995

§ 102(e) Date: Sep. 18, 1995

[87] PCT Pub. No.: WO94/21595

PCT Pub. Date: Sep. 29, 1994

[30] Foreign Application Priority Data

| Mar. 17, 1993 | [JP] | Japan | 5-057248 |
| Mar. 17, 1993 | [JP] | Japan | 5-057249 |
| Mar. 17, 1993 | [JP] | Japan | 5-057251 |
| Mar. 18, 1993 | [JP] | Japan | 5-058875 |
| Mar. 19, 1993 | [JP] | Japan | 5-060599 |
| Mar. 19, 1993 | [JP] | Japan | 5-060600 |
| Mar. 19, 1993 | [JP] | Japan | 5-060601 |
| Mar. 19, 1993 | [JP] | Japan | 5-060602 |
| Mar. 19, 1993 | [JP] | Japan | 5-060603 |
| Mar. 19, 1993 | [JP] | Japan | 5-060604 |
| Feb. 17, 1994 | [JP] | Japan | 6-020184 |
| Mar. 10, 1994 | [JP] | Japan | 6-039480 |
| Mar. 11, 1994 | [JP] | Japan | 6-041324 |

[51] Int. Cl.$^6$ ............................................. A61K 31/13
[52] U.S. Cl. ................... 514/669; 514/668; 514/670; 514/844; 514/845; 514/873; 564/506; 564/507
[58] Field of Search ........................ 564/506, 507; 514/669, 670, 668, 844, 845, 873

[56] References Cited

U.S. PATENT DOCUMENTS

| 3,891,709 | 6/1975 | Higuchi et al. | 260/584 R |
| 4,083,872 | 4/1978 | Schwarze et al. | 260/584 R |
| 5,552,445 | 9/1996 | Ohashi et al. | 514/669 |

*Primary Examiner*—Brian M. Burn
*Attorney, Agent, or Firm*—Oblon, Spivak, McClelland, Maier & Neustadt, P.C.

[57] ABSTRACT

The present invention relates to an amine derivative represented by the following general formula (I) or (II):

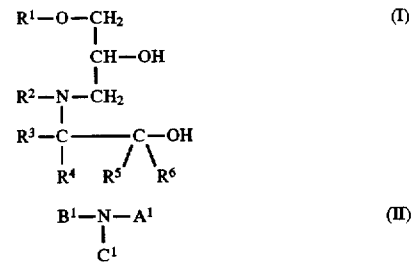

wherein $R^1$ means a heteroatom-containing $C_1$–$C_{40}$ hydrocarbon group which may have a ring structure, or the like; $R^2$–$R^5$ each denote a $C_1$–$C_{20}$ hydrocarbon group, hydrogen or the like; $A^1$ represents

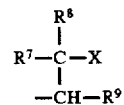

or $R^{15}$—$Z$—$^{16}$—$(CH_2)_n$—; $B^1$ stands for hydrogen, a $C_1$–$C_{10}$ hydrocarbon group, nitrogen or the like; $C^1$ denotes hydrogen, a $C_1$–$C_{10}$ hydrocarbon group, nitrogen, alcohol residue, phosphoric acid residue or the like; a dermatologic preparation containing the same; and a process for producing the amine derivative. This amine derivative has excellent effects of smoothing or removing wrinkles and improving keratinization.

22 Claims, No Drawings

AMINE DERIVATIVE AND DERMATOLOGIC PREPARATION CONTAINING THE SAME

This application is a 35USC371 of PCT/JP94/00436, filed Mar. 17, 1994.

1. Technical Field

The present invention relates to an amine derivative which has excellent effects of preventing and smoothing or removing wrinkles, makes it possible to maintain the normal functions of the skin and moreover is useful for the prevention of dandruff and in improving the skin after sunburn, and an external skin care preparation (hereinafter referred to as "a dermatologic preparation") containing such an amine derivative.

2. Background Art

In recent years, it has been a matter of significant concern to maintain a healthy and beautiful skin irrespective of age or sex. However, the skin is delicately affected by temperature, humidity, ultraviolet rays, cosmetic compositions, aging, diseases, stress, eating habits and the like. Therefore, various troubles such as the decrement of various functions (functions of preventing the loss of water and the like from the vital body, controlling the homeostatic maintenance of the body heat, protecting the body from physical and chemical stimulation and various bacteria and keeping the resilience of the skin to determine its surface form, and the like) of the skin and aging of the skin occur.

Of these, wrinkles, which are one of dermal troubles, occur due to aging or dermal aging by sunlight. More specifically, cells for producing the fibrous tissue of the dermis are made small and lessened by exposure to sunlight or with the increase in age, and particularly, collagen fibers are lost to a great extent, and so the skin is aged by degeneration of the dermis, reduction of subcutaneous adipose tissue and the like, which forms the cause of wrinkles, relaxation and loss of resilience.

Various compositions and methods have heretofore been proposed for preventing or removing wrinkles caused by such an aging effect (Japanese Patent Application Laid-Open Nos. 185005/1987, 502546/1987, 72157/1990 and 288822/1990, etc.).

However, all of these proposals have not exhibited a satisfactory effect of preventing or smoothing wrinkles.

On the other hand, vulgaris cutaneous troubles such as xeroderma, fatty skin and seborrhea sicca in epidermis occur due to the functional aberration of skin tissue caused by intracorporeal and extracorporeal factors, which act on the vital body, such as changes of external environment (seasonal changes, ultraviolet rays, etc.) and variations in physiological functions (attendant on aging or a disease), dermal hypertrophy and parakeratosis induced thereby, etc.

In order to prevent and improve such cutaneous troubles, it has been attempted, for example, to apply a synthetic or natural humectant to the skin, thereby preventing the drying of the skin and enhancing the moistening ability of the skin, or to apply a blood-circulation-accelerating agent to the skin, thereby accelerating the circulation of blood.

However, these methods have involved various problems in respect of the preventing and improving effects on the various cutaneous troubles, persistency thereof, stability and safety of the agents used, and the like. That is, since these methods generally are intended to supply the water of the surface of the epidermis, in particular, of the horny layer, or a part of the humectant, the efficacy and effect thereof have been temporary, and so persistent improvement of the skin has been unable to be expected.

There has thus been a demand for development of a substance having excellent effects of preventing the occurrence of wrinkles and smoothing or removing the wrinkles and on the other hand, possessing marked inhibitory effects on parakeratosis of the skin, dermal hypertrophy, metabolic aberration of lipid and the like.

In view of the foregoing circumstances, the present inventors have carried out an extensive investigation. As a result, it has been found that a specific amine derivative, which will be described subsequently, exhibits marked effects of smoothing or removing wrinkles and improving keratinization, thus leading to completion of the present invention.

DISCLOSURE OF THE INVENTION

The present invention is directed to a method of smoothing or removing wrinkles, which comprises applying, to the skin, an amine derivative represented by the following general formula (I) or (II):

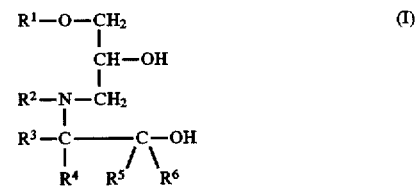

wherein $R^1$ means a hydrocarbon group having 1–3 carbon atoms or a heteroatom-containing hydrocarbon group having 1–40 carbon atoms, which may have a ring structure, and $R^2$, $R^3$, $R^4$, $R^5$ and $R^6$ are identical with or different from one another and denote individually a hydrogen atom or a hydrocarbon group having 1–20 carbon atoms, which may have at least one hydroxyl group,

wherein $A^1$ means

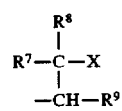

[$R^7$ means a hydrogen atom, a hydrocarbon group having 1–40 carbon atoms, which may have a hydroxyl, carboxyl, alkoxyl, alkylthio, acylamino or acyloxy group, or —$R^{10}$—Y ($R^{10}$ denotes a linear or branched hydrocarbon group having 8–40 carbon atoms, which may have a hydroxyl group, and Y is —$OR^{11}$, —$COOR^{12}$ or

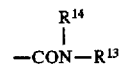

($R^{11}$, $R^{12}$, $R^{13}$ and $R^{14}$ each mean a hydrogen atom or a hydrocarbon group having 1–20 carbon atoms, which may contain an oxygen atom)), $R^8$ denotes a hydrogen atom or a hydrocarbon group having 1–40 carbon atoms, which may have a hydroxyl, carboxyl, alkoxyl, alkylthio, acylamino or acyloxy group, $R^9$ stands for a hydrogen atom, a hydrocarbon group having 1–40 carbon atoms, which may have a hydroxyl, carboxyl, alkoxyl, alkylthio, acylamino or acyloxy group, a carboxyl group, or $$-CH_2OP(OH)_2,$$

and X is a hydrogen atom, hydroxyl group or $$-OP(OH)_2] \text{ or } R^{15}-Z-R^{16} \atop |\atop -(CH_2)_n$$

[$R^{15}$ denotes a linear branched or cyclic hydrocarbon group having 1–40 carbon atoms, which may have a heteroatom. $R^{16}$ means a hydrocarbon group having 1–7 carbon atoms, which may have a hydroxyl or alkoxyl group or $$-OP(OH)_2,$$

Z denotes —COO—, —O—, —S— or —CONR$^{17}$ ($R^{17}$ is a hydrogen atom or a hydrocarbon group having 1–10 carbon atoms, which may have a hydroxyl group), and n stands for an integer of 1–5]; $B^1$ denotes a hydrogen atom, a hydrocarbon group having 1–10 carbon atoms, which may have a hydroxyl group, or a nitrogen atom; and $C^1$ stands for a hydrogen atom, a hydrocarbon group having 1–10 carbon atoms, which may have a hydroxyl group, alkoxyl group, hydroxyalkyloxy group, phosphoric acid residue, carboxyl group or alkoxycarbonyl group, a nitrogen atom, or —$R^{18}$—O—X' [$R^{18}$ means a hydrocarbon group having 2–10 carbon atoms, which may have a hydroxyl group, and X' denotes a hydrogen atom or $$-P(OH)_2],$$

and $B^1$ and $C^1$ may form a heterocyclic ring, which may contain an oxygen atom, together with the adjacent nitrogen atom, or an acid-added salt or quaternized product thereof.

The present invention is also directed to a method of improving keratinization, which comprises applying the amine derivative represented by the general formula (I) or (II), or an acid-added salt or quaternized product thereof to the skin.

The present invention is further directed to a dermatologic preparation comprising the amine derivative represented by the general formula (I) or (II), or an acid-added salt or quaternized product thereof.

The present invention is still further directed to an amine derivative represented by the following general formula (Ia'):

$$\begin{array}{c} R^{21'}-O-CH_2 \\ | \\ CH-OH \\ | \\ R^{22'}-N-CH_2 \\ | \\ R^{23'}-C\underset{R^{24'}\;R^{25'}}{\overset{}{\rule{2em}{0.4pt}}}\overset{}{\underset{R^{26'}}{C}}-OH \end{array} \quad (Ia')$$

wherein $R^{21'}$ means a hydrocarbon group having 8–22 carbon atoms and a hydroxyl or alkoxyl group on its carbon chain, $R^{22'}$, $R^{23'}$ and $R^{24'}$ are identical with or different from one another and denote individually a hydrogen atom, or a methyl, hydroxymethyl or 2-hydroxyethyl group, and $R^{25'}$ and $R^{26'}$ stand for a hydrogen atom, or an acid-added salt thereof.

The present invention is yet still further directed to an amine derivative represented by the following general formula (Ib'):

$$\begin{array}{c} R^{27'}-O-CH_2 \\ | \\ CH-OH \\ | \\ R^{28'}-N-CH_2 \\ | \\ R^{29'}-C\underset{R^{30'}\;R^{31'}}{\overset{}{\rule{2em}{0.4pt}}}\overset{}{\underset{R^{32'}}{C}}-OH \end{array} \quad (Ib')$$

wherein $R^{27'}$ means a tocopheryl or 9,10-(isopropylidenedioxy)octadecyl group, and $R^{28'}$, $R^{29'}$, $R^{30'}$, $R^{31'}$ and $R^{32'}$ are identical with or different from one another and denote individually a hydrogen atom or a hydrocarbon group having 1–10 carbon atoms, which may be substituted by a hydroxyl group, or an acid-added salt thereof.

The present invention is yet still further directed to an amine derivative represented by the following general formula (IId'):

$$\begin{array}{c} R^{57'} \\ | \\ X^{2'}-R^{56'}-C-Y^{3'} \\ | \\ R^{59'}-N-CH-R^{58'} \\ | \\ R^{60'} \\ | \\ OH \end{array} \quad (IId')$$

wherein $R^{56'}$ means a linear or branched hydrocarbon group having 8–40 carbon atoms, $R^{57'}$, $R^{58'}$ and $R^{59'}$ are identical with or different from one another and denote individually a hydrogen atom or a hydrocarbon group having 1–7 carbon atoms, which may have one or more hydroxyl groups, $R^{60'}$ is a hydrocarbon group having 2–6 carbon atoms, which may have one or more hydroxyl groups, $X^{2'}$ stands for —$OR^{61'}$, —$CO_2OR^{62'}$ or $$-CON-R^{63'} \atop | \atop R^{64'}$$

($R^{61'}$, $R^{62'}$, $R^{63'}$ and $R^{64'}$ are identical with or different from one another and denote individually a hydrogen atom or a hydrocarbon group having 1–20 carbon atoms, which may contain an oxygen atom), and $Y^{3'}$ means a hydroxyl group, or an acid-added salt thereof.

The present invention is yet still further directed to an amine derivative represented by the following general formula (IId"):

$$\begin{array}{c} R^{57''} \\ | \\ X^{2'}-R^{56''}-C-Y^{3'} \\ | \\ R^{59''}-N-CH-R^{58''} \\ | \\ R^{60''} \\ | \\ OH \end{array} \quad (IId'')$$

wherein $R^{56''}$ means an undecamethylene, dodecamethylene, tridecamethylene or tetradecamethylene group, $R^{57''}$, $R^{58''}$ and $R^{59''}$ denote individually a hydrocarbon group having 1–7 carbon atoms, which may have one or more hydroxyl groups, $R^{60''}$ is a hydrocarbon group having 2–6 carbon atoms, which may have one or more hydroxyl groups, $X^{2'}$ stands for a hydroxyl group, and $y^{3'}$ means a hydrogen atom, or an acid-added salt thereof.

The present invention is yet still further directed to an amine derivative represented by the following general formula (IIe'):

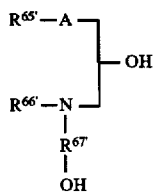

wherein $R^{65'}$ means a linear or branched hydrocarbon group having 7–24 carbon atoms and containing an oxygen atom, $R^{66'}$ and $R^{68'}$ denote individually a hydrogen atom or a hydrocarbon group having 1–10 carbon atoms, which may be substituted by a hydroxyl group, $R^{67'}$ stands for a hydrocarbon group having 2–10 carbon atoms, which may be substituted by a hydroxyl group, and A represents —CO$_2$—, —S— or

or an acid-added salt thereof.

BEST MODE FOR CARRYING OUT THE INVENTION

The amine derivatives useful in the practice of the present invention are represented by the general formula (I) or (II).

In the general formula (I), the hydrocarbon groups represented by $R^1$–$R^6$ may be either saturated or unsaturated, and any of linear, branched and cyclic hydrocarbon groups. In $R^1$, the hydrocarbon groups having 1–3 carbon atoms include alkyl or alkenyl groups having 1–3 carbon atoms, specifically, methyl, ethyl, propyl, isopropyl and allyl. In the heteroatom-containing hydrocarbon groups in $R^1$, which have 1–40 carbon atoms and may have a ring structure, examples of the heteroatoms contained in these groups include oxygen, nitrogen, silicon, fluorine, chlorine, bromine, iodine, sulfur and phosphorus atoms. Of these, oxygen, nitrogen, silicon and fluorine atoms are preferred. The heteroatom-containing hydrocarbon groups each have a structure that one or more hydrogen atoms of a hydrocarbon group containing no heteroatom have been substituted by the corresponding number of heteroatoms and/or heteroatom-containing atomic groups. Examples of the atomic groups include hydroxyl, alkoxyl, carboxyl, alkoxycarbonyl, acylamino, acyl, acyloxy, alkoxycarbonyloxy, aminocarbonyloxy, amino, alkylsilyl, mercapto, alkylthio, sulfonyl, sulfonyloxy and phosphoryloxy groups. Of these, hydroxyl, alkoxyl, carboxyl, alkoxycarbonyl, acylamino and alkylsilyl group are preferred.

Examples of the hydrocarbon moiety containing no heteroatom include hydrocarbon groups such as octyl, nonyl, decyl, undecyl, dodecyl, tridecyl, tetradecyl, pentadecyl, hexadecyl, heptadecyl, octadecyl, dotriacontyl, 2-ethylhexyl and 9-octadecenyl.

These hydrocarbon groups represented by $R^1$ may have a ring structure. Such a hydrocarbon group may be either a group composed of only a ring structure or a group partially having a ring structure. The ring structure may be any of alicyclic, aromatic and heterocyclic rings. Examples thereof include benzene, pyran, tetrahydropyran, furan, tetrahydrofuran, dioxolane and dioxane.

Preferable specific examples of the heteroatom-containing hydrocarbon groups and the hydrocarbon groups having a ring structure in $R^1$ include groups such as 2-hydroxyethyl, 3-hydroxypropyl, 2,3-dihydroxypropyl, 2,2-bis(hydroxymethyl)-3-hydroxypropyl, carboxymethyl, aminocarbonylmethyl, 1-(N,N-dimethylamino)ethyl, 12-hydroxyoctadecyl, 12-hydroxydodecyl, 9-hydroxynonyl, 9,10-dihydroxyoctadecyl, 12-hydroxy-9-octadecenyl, 12-methoxy-octadecyl, 10-(2-ethylhexyloxy)decyl, 11-carboxyundecyl, 11-butoxycarbonylundecyl, 11-(2-ethylhexanoylamino)undecyl, 11-(butyldimethylsilyl) undecyl, tocopheryl, 4-dodecyloxyphenyl, 4-(9-hydroxynonyloxy)phenyl, 9-(4-butoxyphenyloxy)nonyl, 4-(dodecylaminocarbonyl)phenyl, 11-(cyclohexanecarbonylamino)undecyl, 11-(phenyldimethylsilyl)undecyl and 9,10-(isopropylidenedioxy)octadecyl.

In the general formula (I), examples of $R^2$, $R^3$, $R^4$, $R^5$ and $R^6$ include a hydrogen atom and hydrocarbon groups which have 1–20 carbon atoms, preferably 1–5 carbon atoms and may be substituted by 1–5 hydroxyl groups. Preferable specific examples thereof include a hydrogen atom; alkyl groups having 1–20 carbon atoms, such as methyl, ethyl, butyl, hexyl, tetradecyl and octadecyl; aryl groups such as phenyl; aralkyl groups such as benzyl; and alkyl groups substituted by 1–5 hydroxyl groups, such as hydroxymethyl, 2-hydroxyethyl, 1,2-dihydroxypropyl, 1,2,3-trihydroxybutyl, 1,2,3,4-tetrahydroxypentyl and 1,2,3,4,5-pentahydroxyhexyl.

These amine derivatives represented by the general formula (I) are prepared in accordance with various known processes, and no particular limitation is hence imposed on the preparation processes thereof. However, they may be prepared, for example, by deriving a glycidyl ether derivative (IV) from a heteroatom-containing alcohol (III) and adding an amine (V) to this glycidyl ether derivative as represented by the following reaction scheme. At this time, if the heteroatom-containing alcohol (III) has a reactive functional group such as a hydroxyl, carboxyl or amino group, the reaction may be carried out after the above functional group is protected by an appropriate protective group, and deblocking may be finally conducted to prepare the amine derivative (I).

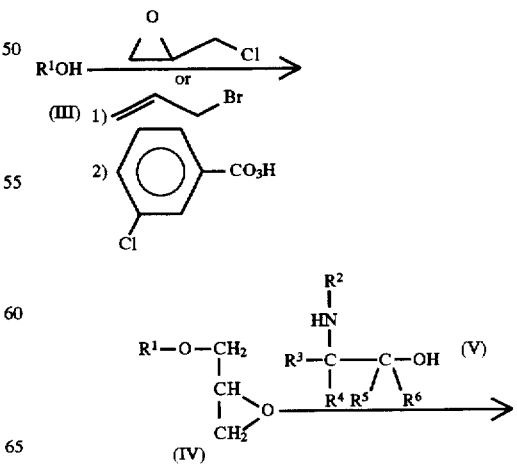

-continued

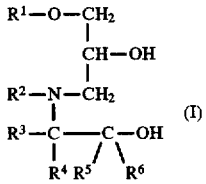
(I)

wherein $R^1$, $R^2$, $R^3$, $R^4$, $R^5$ and $R^6$ have the same meaning as defined above.

In $R^7$, $R^8$ and $R^9$ in the general formula (II), the hydrocarbon groups having 1–40 carbon atoms, which may have a hydroxyl, carboxyl, alkoxyl, alkylthio, acylamino or acyloxy group may be either saturated or unsaturated, and any of linear, branched and cyclic hydrocarbon groups. Specific examples thereof include groups such as methyl, ethyl, propyl, butyl, pentyl, hexyl, octyl, decyl, dodecyl, tetradecyl, pentadecyl, hexadecyl, heptadecyl, eicosyl, methyl-branched isopalmityl, 4,8,12-trimethyltridecyl, cyclohexyl, phenyl, benzyl, hydroxymethyl, 1-hydroxyethyl, 1-hydroxypropyl, 1-hydroxybutyl, 1-hydroxypentyl, 1-hydroxydodecyl, 1-hydroxytetradecyl, 1-hydroxypentadecyl, 1-hydroxyhexadecyl, 1-hydroxyheptadecyl, 9-hydroxynonyl, 13-hydroxytridecyl, 14-hydroxytetradecyl, 1,2-dihydroxyethyl, 1,2,3-trihydroxy-propyl, 1,2,3,4-tetrahydroxybutyl, 1,2,3,4,5-pentahydroxypentyl, methoxymethyl, dodecyloxymethyl, tetradecyloxymethyl, methyl-branched isostearyloxymethyl, 4-methyl-3-pentenyl, 1-pentadecenyl, 7-hexadecenyl, 1-heptadecenyl, 1-nonenyl, 1-undecenyl, 1-tridecenyl, 1-nonadecenyl, 11-hydroxyheptadecenyl, 13-hydroxynonadecenyl, 9-methylhexadecyl, 11-methyloctadecenyl, carboxy, 8-carboxyoctyl, 12-carboxydodecyl, 13-carboxytridecyl, dodecyloxymethyl, tetradecyloxymethyl, hexadecyloxymethyl, methyl-branched isostearyloxymethyl, 12-hydroxyoctadecyloxymethyl, 15-hydroxypentadecyloxymethyl, 9-(2-ethylhexyloxy) nonyloxymethyl, dodecylthiomethyl, tetradecylthiomethyl, dodecanoylaminomethyl, tetradecanoylaminomethyl, hexadecanoylaminomethyl, methyl-branched isostearoylaminomethyl, 12-hydroxyoctadecanoylaminomethyl, 15-hydroxypentadecanoylaminomethyl, 16-hydroxyhexadecanoylaminomethyl, 12-(2-ethylhexyloxy)dodecanoylaminomethyl, 11-(2-ethylhexanoylamino)undecanoylaminomethyl, dodecanoyloxymethyl, tetradecanoyloxymethyl, methyl-branched isostearoyloxymethyl and 2-ethylhexyloxymethyl.

The linear or branched divalent hydrocarbon group having 8–40 carbon atoms indicated by $R^{10}$, which may have a hydroxyl group, may be either saturated or unsaturated. Specific examples thereof include groups such as octamethylene, nonamethylene, decamethylene, undecamethylene, dodecamethylene, tridecamethylene, tetradecamethylene, hexadecamethylene, triacontamethylene, hexadecane-1,10-diyl, 7-hexadecene-1,10-diyl, 2-hydroxyundecane-1,11-diyl, 2-hydroxytridecane-1,13-diyl and 2-hydroxytetradecane-1,14-diyl.

In $R^{11}$, $R^{12}$, $R^{13}$ and $R^{14}$, the hydrocarbon groups having 1–20 carbon atoms, which may contain an oxygen atom may be any of linear, branched and cyclic hydrocarbon groups. Specific examples thereof include groups such as methyl, ethyl, butyl, hexyl, octyl, dodecyl, hexadecyl, octadecyl, 2-ethylhexyl, allyl, 2-hydroxyethyl, 2,3-dihydroxypropyl, 2-hydroxypropyl, 6-hydroxyhexyl, 9-hydroxynonyl, 12-hydroxydodecyl, phenyl, benzyl and tetrahydropyranyl.

In the linear, branched or cyclic hydrocarbon group having 1–40 carbon atoms represented by $R^{15}$, which may have a heteroatom, examples of the heteroatom contained in $R^{15}$ include oxygen, sulfur, nitrogen and silicon atoms. Of these, an oxygen atom is particularly preferred. The hydrocarbon group of $R^{15}$ may be either saturated or unsaturated. Specific examples thereof include groups such as methyl, ethyl, propyl, butyl, pentyl, hexyl, heptyl, octyl, nonyl, decyl, undecyl, dodecyl, tridecyl, tetradecyl, pentadecyl, heptadecyl, hexadecyl, octadecyl, docosyl, hentriacontyl, dotriacontyl, methyl-branched isoheptadecyl, methyl-branched isostearyl, 2-ethylhexyl, 2-heptylundecyl, 5,7,7-trimethyl-2-(1,3,3-trimethylbutyl)octyl, 9-octadecenyl, 9,12-octadecadienyl, cyclohexyl, phenyl, benzyl, cholesteryl, 12-hydroxyoctadecyl, 12-hydroxydodecyl, 9-hydroxynonyl, 9,10-dihydroxyoctadecyl, 12-hydroxy-9-octadecenyl, 12-methoxyoctadecyl, 10-(2-ethylhexyloxy) decyl, 11-carboxyundecyl, 11-butoxycarbonylundecyl, 11-(2-ethylhexanoylamino)undecyl, 11-(butyldimethylsilyl) undecyl, tocopheryl, 9,10-isopropylidenedioxyoctadecyl, hepta-3-yl, heptadeca-8-yl, 8-heptadecenyl, 8,11-heptadecadienyl, 9-decenyl, cyclohexyl, phenyl, 8-hydroxyoctyl, 11-hydroxyundecyl, 14-hydroxytetradecyl, 15-hydroxypentadecyl, 11-hydroxyheptadecyl, 8,9-dihydroxyheptadecyl, 11-hydroxy-8-heptadecenyl, 11-methoxyheptadecyl, 9-(2-ethylhexyl)nonyl, 10-carboxydecyl, 10-butoxycarbonyldecyl, 10-(2-ethylhexanoylamino)decyl, 10-(butyldimethylsilyl)decyl and 8,9-isopropylidenedioxyheptadecyl.

The hydrocarbon group having 1–7 carbon atoms represented by $R^{16}$, which may have a hydroxyl or alkoxyl group or

may be either linear or branched and saturated or unsaturated. Specific examples thereof include groups such as methylene, dimethylene, ethylidene, isopropylidene, hydroxydimethylene and,

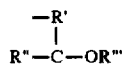

(R' means a hydrocarbon group having 1–3 carbon atom, R" denotes a hydrogen atom or a hydrocarbon group having 1–3 carbon atoms, and R"' is a hydrogen atom, a hydrocarbon group having 1–3 carbon atoms or

In $R^{17}$ and $B^1$, specific examples of the hydrocarbon groups having 1–10 carbon atoms, which may have a hydroxyl group, include groups such as methyl, ethyl, butyl, hexyl, phenyl, benzyl, hydroxyethyl, 2,3-dihydroxypropyl, 2,3,4-trihydroxybutyl, 2,3,4,5-tetrahydroxypentyl and 2,3,4,5,6-pentahydroxyhexyl.

In $C^1$, the hydrocarbon group having 1–10 carbon atoms, which may have a hydroxyl group, alkoxyl group, hydroxyalkyloxy group, phosphoric acid residue, carboxyl group or alkoxycarbonyl group, may be any of linear, branched and cyclic hydrocarbons, and either saturated or unsaturated. Specific examples thereof include groups such as methyl, ethyl, propyl, hexyl, cyclohexyl, phenyl, benzyl and the following groups:

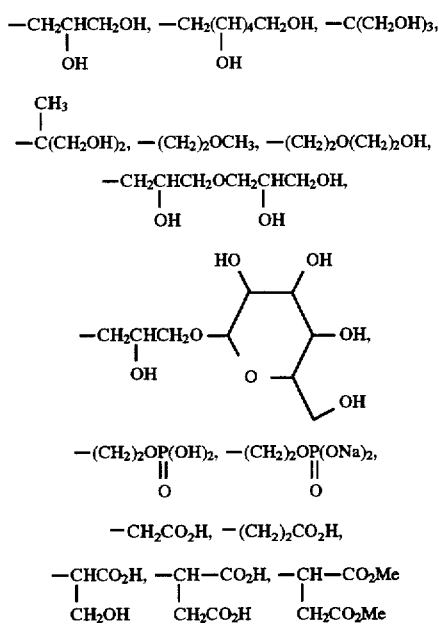

Specific examples of the hydrocarbon group having 2–10 carbon atoms represented by $R^{18}$, which may have a hydroxyl group, include $-(CH_2)_2-$, $-(CH_2)_3-$, $-(CH_2)_4-$,

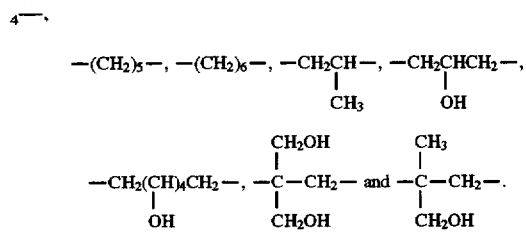

Examples of the ring formed by $B^1$ and $C^1$ include the following rings:

These amine derivatives (II) are prepared in accordance with various known processes, for example, the following reaction schemes 1 to 11.

Reaction Scheme 1:

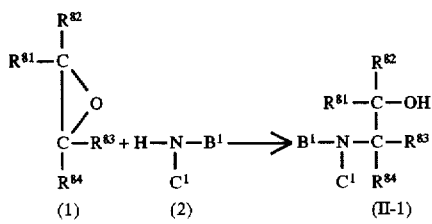

wherein $R^{81}$ means a hydrogen atom, a hydrocarbon group having 1–40 carbon atoms, which may have a hydroxyl, carboxyl, alkoxyl, alkylthio, acylamino or acyloxy group, $-R^{10}-Y$ ($R^{10}$ and Y having the same meaning as defined above). $R^{82}$ denotes a hydrogen atom or a hydrocarbon group having 1–40 carbon atoms, which may have a hydroxyl, carboxyl, alkoxyl, alkylthio, acylamino or acyloxy group. $R^{83}$ stands for a hydrogen atom, a hydrocarbon group having 1–40 carbon atoms, which may have a hydroxyl, carboxyl, alkoxyl, alkylthio, acylamino or acyloxy group, or a carboxyl group. $R^{84}$ represents a hydrogen atom or a methyl group, and $B^1$ and $C^1$ have the same meaning as defined above.

Namely, an amine (2) is added to an epoxide (1), thereby obtaining an amine derivative (II-1).

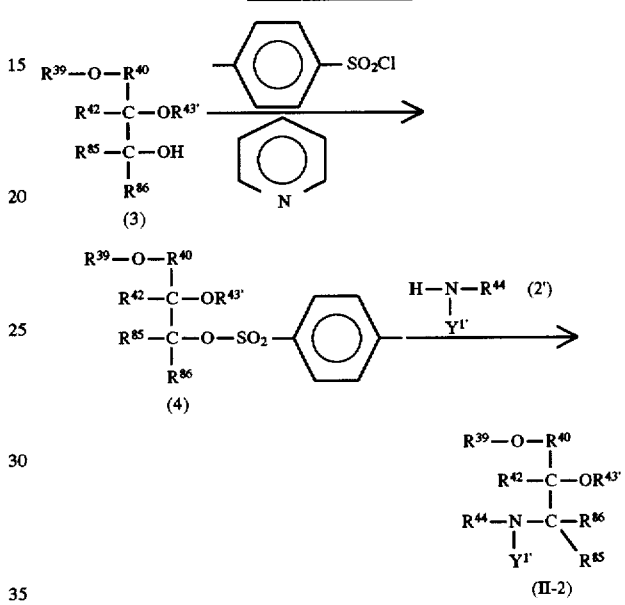

wherein $R^{39}$ means a linear, branched or cyclic hydrocarbon group having 1–40 carbon atoms, which may have a heteroatom. $R^{40}$ denotes a divalent hydrocarbon group having 1–3 carbon atoms. $R^{42}$ represents a hydrogen atom or a hydrocarbon group having 1–3 carbon atoms. $R^{43'}$ stands for a hydrocarbon group having 1–3 carbon atoms. $R^{44}$ is a hydrogen atom or a hydrocarbon group having 1–10 carbon atoms, which may have one or more hydroxyl groups. $Y^{1'}$ means a hydrocarbon group having 1–10 carbon atoms and containing one or more groups selected from the group consisting of hydroxyl, alkoxyl, hydroxyalkyloxy, carboxyl and alkoxycarbonyl groups, and $R^{85}$ and $R^{86}$ denote individually a hydrogen atom or a methyl group.

Namely, an alcohol (3) is converted to a p-toluenesulfonate (4), and the resultant p-toluene sulfonate is then reacted with an amine (2'), thereby obtaining an amine derivative (II-2).

Reaction Scheme 3:

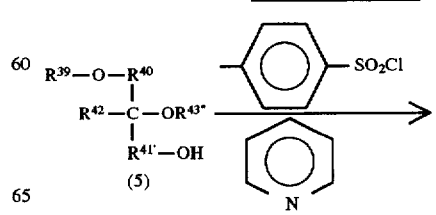

Reaction Scheme 3:

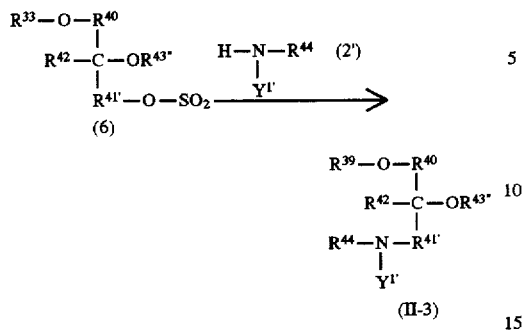

(II-3)

wherein $R^{41}$ means —$(CH_2)_\alpha$— ($\alpha$ is 2 or 3), $R^{43''}$ denotes a hydrogen atom or a hydrocarbon group having 1–3 carbon atoms, and other groups have the same meaning as defined above.

Namely, an alcohol (5) is converted to a p-toluenesulfonate (6), and the resultant p-toluene sulfonate is then reacted with an amine (2'), thereby obtaining an amine derivative (II-3).

Reaction Scheme 4:

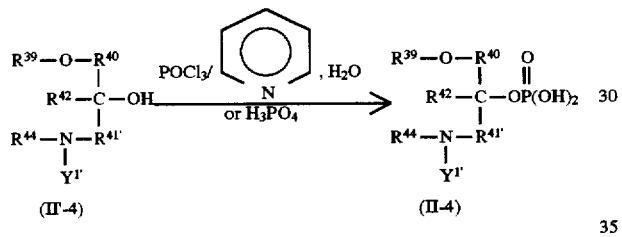

wherein $R^{39}$, $R^{40}$, $R^{41}$, $R^{42}$, $R^{44}$ and $Y^{1'}$ have the same meaning as defined above.

Namely, an amine derivative (II-4) obtained in Reaction Scheme 1 or 3 is phosphorylated in the presence of a phosphorylating agent such as $POCl_3$ or $H_3PO_4$, thereby obtaining an amine derivative (II-4).

Reaction Scheme 5:

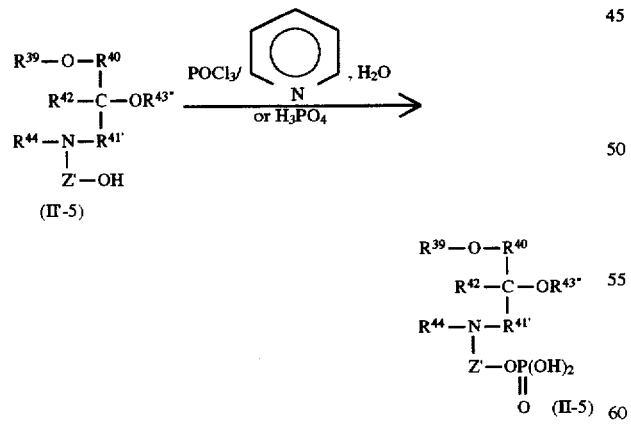

wherein Z' means a hydrocarbon group having 1–10 carbon atoms, which may contain one or more of hydroxyl, alkoxyl, hydroxyalkyloxy, carboxyl and alkoxycarbonyl groups, and other groups have the same meaning as defined above.

Namely, an amine derivative (II-5) obtained in any of Reaction Schemes 1 to 4 is phosphorylated with a phosphorylating agent such as $POCl_3$ or $P_2O_5$, thereby obtaining an amine derivative (II-5).

Reaction Scheme 6:

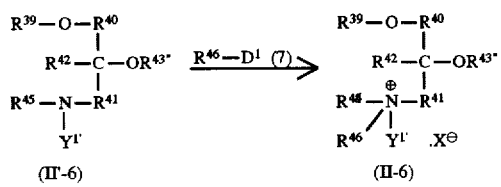

wherein $R^{45}$ and $R^{46}$ are identical with or different from each other and mean individually a hydrocarbon group having 1–3 carbon atoms, which may have 1–3 hydroxyl groups, $D^1$ denotes a halogen atom, and other groups have the same meaning as defined above.

Namely, an amine derivative (II-6) obtained in any of Reaction Schemes 1 to 5 is quaternized with an alkyl halide (7), thereby obtaining an amine derivative (II-6).

Reaction Scheme 7:

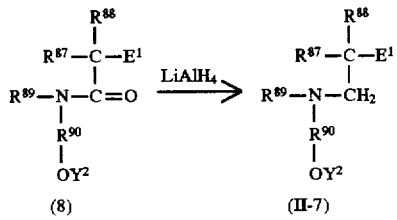

wherein $R^{87}$ means a hydrogen atom, a linear, branched or cyclic hydrocarbon group having 1–40 carbon atoms or $X^2$—$R^{56}$— [$R^{56}$ is a linear or branched hydrocarbon group having 8–40 carbon atoms, which may have a hydroxyl group, and $X^2$ is —$OR^{61}$, —$CO_2R^{62}$ or

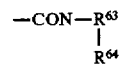

($R^{61}$, $R^{62}$, $R^{63}$ and $R^{64}$ are identical with or different from one another and denote individually a hydrogen atom or a hydrocarbon group having 1–20 carbon atoms, which may contain an oxygen atom)], $R^{88}$ and $R^{89}$ are identical with or different from each other and denote individually a hydrogen atom or a hydrocarbon group having 1–7 carbon atoms, which may have one or more hydroxyl groups, $R^{90}$ stands for a divalent hydrocarbon group having 2–6 carbon atoms, which may have one or more hydroxyl groups, $E^1$ represents a hydrogen atom or a hydroxyl group, and $Y^2$ is a hydrogen atom or

Namely, an amide (8) is reduced with $LiAlH_2$ or the like, thereby obtaining an amine derivative (II-7).

Reaction Scheme 8:

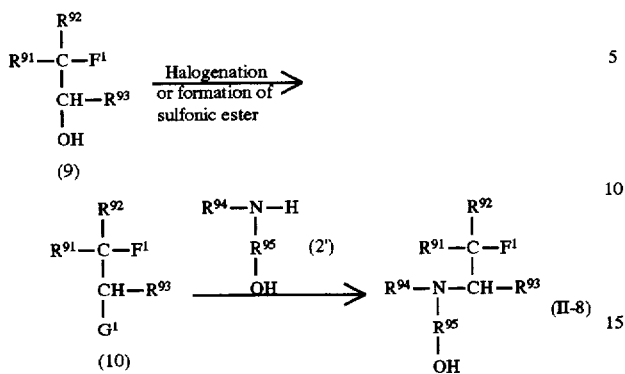

wherein $R^{91}$ means a hydrogen atom, a linear, branched or cyclic hydrocarbon group having 1–40 carbon atoms or $X^2-R^{56}-(X^2$ and $R^{56}$ have the same meaning as defined above), $R^{92}$, $R^{93}$ and $R^{94}$ are identical with or different from one another and denote individually a hydrogen atom or a hydrocarbon group having 1–7 carbon atoms, which may have one or more hydroxyl groups, $R^{95}$ stands for a divalent hydrocarbon group having 2–6 carbon atoms, which may have one or more hydroxyl groups, $F^1$ represents a hydrogen atom or a hydroxyl group, and $G^1$ represents a chlorine, bromine or iodine atom, or

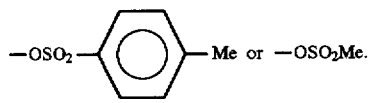

Namely, an amine (2') is added to a compound (10) obtained by subjecting an alcohol (9) to halogenation or formation of a sulfonic ester, thereby obtaining an amine derivative (II-8).

Reaction Scheme 9:

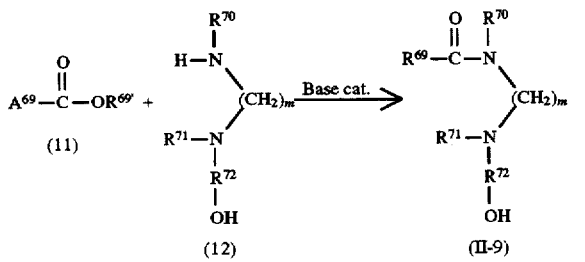

wherein $R^{69}$ means a linear, branched or cyclic hydrocarbon group having 1–40 carbon atoms, which may contain a heteroatom, $R^{69'}$ denotes a lower alkyl group, $R^{70}$ and $R^{71}$ are identical with or different from each other and represent individually a hydrogen atom or a hydrocarbon group having 1–10 carbon atoms, which may have one or more hydroxyl groups, $R^{72}$ represents a hydrocarbon group having 2–6 carbon atoms, which may have one or more hydroxyl groups, and m stands for an integer of 2–6.

Namely, an ester (11) is reacted with an amine (12) in the presence of a base catalyst, thereby obtaining an amine derivative (II-9).

Reaction Scheme 10:

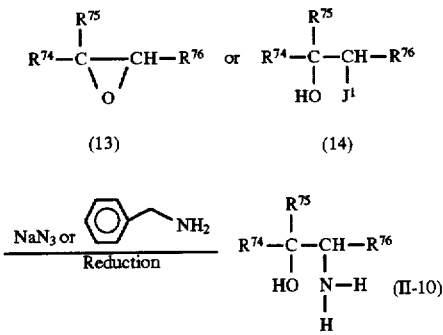

wherein $R^{74}$ and $R^{75}$ are identical with or different from each other and mean individually a hydrogen atom or a hydrocarbon group having 1–40 carbon atoms, which may have a hydroxyl, carboxyl, alkoxyl, alkylthio, acylamino or acyloxy group, $R^{76}$ denotes a hydrogen atom or a hydrocarbon group having 1–40 carbon atoms, which may have an alkoxyl, alkylthio, acylamino or acyloxy group, or a hydrocarbon group having 1–40 carbon atoms, which may have a hydroxyl or carboxyl group, with the proviso that the total number of carbon atoms contained in $R^{74}$, $R^{75}$ and $R^{76}$ is at least 5, and $J^1$ stands for a chlorine, bromine or iodine atom, or

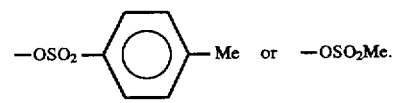

Namely, an epoxide (13), or a halide or sulfonic ester (14) is reacted with NaN₃ or benzylamine, and the resultant product is then reduced, thereby obtaining an amine derivative (II-10).

Reaction Scheme 11:

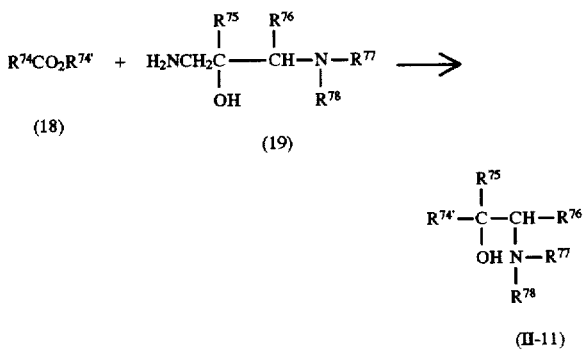

wherein $R^{74'}$ means a lower alkyl group, $R^{74'}$ denotes $R^{74}$—CONHCH₂—, $R^{77}$ and $R^{78}$ are identical with or different from each other and represent individually a hydrogen atom, a hydrocarbon group having 1–10 carbon atoms or a nitrogen atom, or form together a cyclic hydrocarbon group, which may have an ether oxygen, and other groups have the same meaning as defined above.

Namely, an ester (18) is reacted with an amine (19), thereby obtaining an amine derivative (II-11).

In these reactions, if a reactive functional group such as a carboxyl or hydroxyl group exists in a compound used as a raw material, the reaction may be carried out after such a functional group is protected by an appropriate protective group, and deblocking may be finally conducted to prepare the amine derivative (II).

Among these amine derivatives (I) or (II), those represented by the following formulae (Ia)–(Ic) and (IIa)–(IIh) are particularly preferred. (Ia):

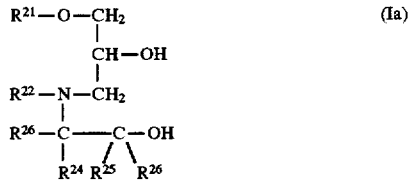

wherein $R^{21}$ means a linear or branched hydrocarbon group having 7–40 carbon atoms and containing a heteroatom. $R^{22}$, $R^{23}$, $R^{24}$, $R^{25}$ and $R^{26}$ are identical with or different from one another and denote individually a hydrogen atom or a hydrocarbon group having 1–10 carbon atoms, which may have one or more hydroxyl groups.

Preferable examples of $R^{22}$–$R^{26}$ include a hydrogen atom, alkyl groups having 1–6 carbon atoms and alkyl groups having 1–6 carbon atoms and substituted by 1–5 hydroxyl groups. Particularly preferable examples thereof include a hydrogen atom, and hydroxymethyl, 2-hydroxyethyl and 1,2,3,4-tetrahydroxybutyl groups.

In the general formula (Ia), compounds in which $R^{21}$ is a hydrocarbon group having 8–22 carbon atoms and a hydroxyl or alkoxyl group on their carbon chains, and $R^{22}$–$R^{26}$ are individually a hydrogen atom or a methyl, hydroxymethyl, 2-hydroxyethyl or 1,2,3,4-tetrahydroxybutyl group are further preferred. Of these, compounds in which $R^{21}$ is a hydrocarbon group having 8–22 carbon atoms and a hydroxyl or alkoxyl group on their carbon chains, and $R^{22}$–$R^{26}$ are individually a hydrogen atom; or compounds in which $R^{21}$ is a hydrocarbon group having 8–22 carbon atoms and a hydroxyl or alkoxyl group on their carbon chains, and $R^{22}$ is a methyl or 2-hydroxyethyl group, and $R^{23}$–$R^{26}$ are individually a hydrogen atom are particularly preferred.

Besides, compounds in which $R^{21}$ is a hydrocarbon group having 8–22 carbon atoms and a hydroxyl or alkoxyl group on their carbon chains, $R^{22}$, $R^{23}$ and $R^{24}$ are individually a hydrogen atom or a methyl, hydroxymethyl or 2-hydroxyethyl group, and $R^{25}$ and $R^{26}$ are individually a hydrogen atom are novel compounds. Therefore, the present invention also provides such compounds or acid-added salts thereof. (Ib):

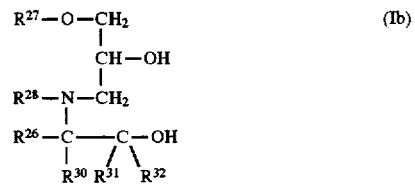

wherein $R^{27}$ means a hydrocarbon group having 7–40 carbon atoms, which has a ring structure and contains a heteroatom, and $R^{28}$, $R^{29}$, $R^{30}$, $R^{31}$ and $R^{32}$ are identical with or different from one another and denote individually a hydrogen atom or a hydrocarbon group having 1–10 carbon atoms, which may be substituted by a hydroxyl group.

Examples of the heteroatom contained in $R^{27}$ of the amine derivatives represented by the general formula (Ib) include O, S, N, Si, etc.

In the general formula (Ib), the hydrocarbon group represented by $R^{27}$ and having a ring structure may be either a group composed of only a ring structure or a group partially having a ring structure. The ring structure may be any of alicyclic, aromatic and heterocyclic rings. Examples thereof include benzene, pyran, tetrahydropyran, furan, tetrahydrofuran, dioxolane and dioxane.

Groups such as tocopheryl, 4-dodecyloxyphenyl, 4-(9-hydroxynonyloxy)phenyl, 9-(4-butoxyphenyloxy)nonyl, 4-(dodecylamonocarbonyl)phenyl, 11-(cyclohexanecarbonylamino)-undecyl, 11-(phenyldimethylsilyl)undecyl and 9,10-(isopropylidenedioxy)octadecyl are preferred as $R^{27}$.

Preferable examples of $R^{28}$, $R^{29}$, $R^{30}$, $R^{31}$ and $R^{32}$ include a hydrogen atom and hydrocarbon groups such as methyl, ethyl, butyl, hexyl, phenyl, benzyl, hydroxymethyl, hydroxyethyl, 1,2-dihydroxyethyl, 1,2,3-trihydroxypropyl, 1,2,3,4-tetrahydroxybutyl and 1,2,3,4,5-pentahydroxypentyl.

In the general formula (Ib), amine derivatives (Ib') in which $R^{27}$ is a tocopheryl or 9,10-(isopropylidenedioxy) octadecyl group are novel compounds. Therefore, the present invention also provides such compounds or acid-added salts thereof. (Ic):

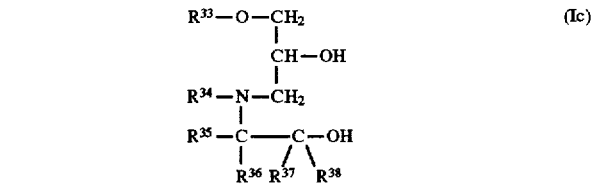

wherein $R^{33}$ means a hydrocarbon group having 1–3 carbon atoms or a heteroatom-containing hydrocarbon group having 1–5 carbon atoms, and $R^{34}$, $R^{35}$, $R^{36}$, $R^{37}$ and $R^{38}$ are identical with or different from one another and denote individually a hydrogen atom or a hydrocarbon group having 1–20 carbon atoms, which may be substituted by at least one hydroxyl group.

In the general formula (Ic), examples of the hydrocarbon group having 1–3 carbon atoms of $R^{33}$ include alkyl or alkenyl groups having 1–3 carbon atoms. Groups such as methyl, ethyl, propyl, isopropyl and allyl are preferred. Examples of the heteroatom-containing hydrocarbon group having 1–5 carbon atoms of $R^{33}$ include hydrocarbon groups containing an oxygen atom, nitrogen atom, silicon atom, sulfur atom, phosphorus atom and/or fluorine atom. Of these, hydrocarbon groups containing an oxygen atom and/or nitrogen atom are preferred, with 2-hydroxyethyl, 3-hydroxypropyl, 2,3-dihydroxypropyl, 2,2-bis (hydroxymethyl)-3-hydroxypropyl, carboxymethyl, aminocarbonylmethyl, 1-(N,N-dimethylamino)ethyl and the like being preferred. Of these, alkyl groups having 1–5 carbon atoms, which have been substituted by 1–3 hydroxyl groups, are particularly preferred.

In the general formula (Ic), a hydrogen atom and hydrocarbon groups having 1–20 carbon atoms, preferably 1–5 carbon atoms, which may be substituted by 1–5 hydroxyl groups, are preferred as $R^{34}$, $R^{35}$, $R^{36}$, $R^{37}$ and $R^{38}$. Of these, are particularly preferred a hydrogen atom; alkyl groups having 1–20 carbon atoms, such as methyl, ethyl, butyl, hexyl, tetradecyl and octadecyl; aryl groups such as phenyl; aralkyl groups such as benzyl; and alkyl groups substituted by 1–5 hydroxyl groups, such as hydroxymethyl, 2-hydroxyethyl, 1,2-dihydroxypropyl, 1,2,3-trihydroxybutyl, 1,2,3,4-tetrahydroxypentyl and 1,2,3,4,5-pentahydroxyhexyl.

In the general formula (Ic), compounds in which $R^{33}$ is an alkyl group having 1–3 carbon atom or an alkyl group having 1–5 carbon atoms, which has been substituted by 1–3 hydroxyl groups. $R^{34}$ is a hydrogen atom, or a 2-hydroxyethyl, methyl or benzyl group, and $R^{35}$, $R^{36}$, $R^{37}$ and $R^{38}$ are individually a hydrogen atom, or a methyl, hydroxymethyl, 2-hydroxyethyl or 1,2,3,4-tetrahydroxypentyl group are particularly preferred. (IIa), (IIb):

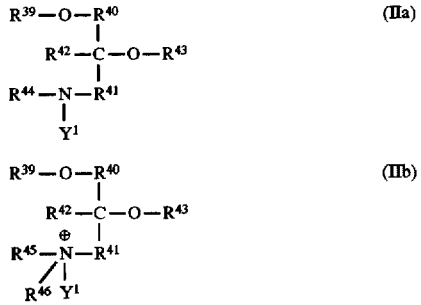

wherein $R^{39}$ means a linear, branched or cyclic hydrocarbon group having 1–40 carbon atoms, which may contain a heteroatom. $R^{40}$ and $R^{41}$ are identical with or different from each other and denote individually a divalent hydrocarbon group having 1–3 carbon atoms, $R^{42}$ represents a hydrogen atom or a hydrocarbon group having 1–3 carbon atoms, $R^{43}$ stands for a hydrogen atom or a hydrocarbon group having 1–3 carbon atoms or

$R^{44}$ is a hydrogen atom or a hydrocarbon group having 1–10 carbon atoms, which may have one or more hydroxyl groups, $R^{45}$ and $R^{46}$ are identical with or different from each other and represent individually a hydrocarbon group having 1–3 carbon atoms, which may have 1–3 hydroxyl groups, and $Y^1$ means a hydrocarbon group having 1–10 carbon atoms and containing one or more groups selected from the group consisting of a hydroxyl group, alkoxyl group, hydroxyalkyloxy group, phosphoric acid residue, carboxyl group and alkoxycarbonyl group, with the proviso that in the formula (IIa), the case where both $R^{40}$ and $R^{41}$ are —CH$_2$—, both $R^{42}$ and $^{43}$ are hydrogen atoms, and $Y^1$ is the following formula (a):

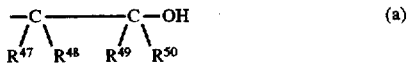

in which $R^{47}$, $R^{48}$, $R^{49}$ and $R^{50}$ have the same meaning as $R^{44}$, is excluded.

In the general formula (IIa) or (IIb), the hydrocarbon group represented by $R^{39}$ may be either saturated or unsaturated. Such a group is preferably a linear, branched or cyclic hydrocarbon group having 1–25 carbon atoms, more preferably a linear or branched hydrocarbon group having 1–25 carbon atom, further preferably a linear or branched hydrocarbon group having 1–3 or 14–22 carbon atoms, particularly preferable a linear or branched alkyl or alkenyl group having 1–3 or 14–22 carbon atoms.

Examples of the heteroatom contained in $R^{39}$ include oxygen, nitrogen, silicon and sulfur atoms. Of these, an oxygen atom and/or a nitrogen atom is preferred, with an oxygen atom being particularly preferred. The heteroatom in $R^{39}$ is contained in the form of an atomic group containing at least one heteroatom. Example of such an atomic group include hydroxyl, alkoxyl, alkoxycarbonyl, alkanoyl, alkanoylamino, amino, mono-, di- or tri-alkylamino, trialkylsilyl and alkylidenedioxy groups. The numbers of carbon atoms in the alkyl and alkanoyl groups included in such atomic groups are preferably 1–6.

Particularly preferable specific examples of $R^{39}$ include groups such as methyl, ethyl, propyl, butyl, hexyl, heptyl, octyl, decyl, dodecyl, tetradecyl, pentadecyl, hexadecyl, octadecyl, docosyl, dotriacontyl, methyl-branched isostearyl, 2-ethylhexyl, 2-heptylundecyl, 5,7,7-trimethyl-2-(1,3,3-trimethylbutyl)octyl, 9-octadecenyl, 9,12-octadecadienyl, cyclohexyl, phenyl, benzyl, cholesteryl, 12-hydroxyoctadecyl, 12-hydroxydodecyl, 9-hydroxynonyl, 9,10-dihydroxyoctadecyl, 12-hydroxy-9-octadecenyl, 12-methoxyoctadecyl, 10-(2-ethylhexyloxy)decyl, 11-carboxyundecyl, 11-butoxycarbonylundecyl, 11-(2-ethylhexanoylamino)undecyl, 11-(butyldimethylsilyl) undecyl, tocopheryl and 9,10-isopropylidenedioxyoctadecyl. Of these, methyl, methyl-branched isostearyl and 12-hydroxyoctadecyl are particularly preferred.

$R^{40}$ and $R^{41}$ are preferably alkylene or alkylidene groups having 1–3 carbon atoms. Specific examples thereof include methylene, ethylene, trimethylene, propylene, ethylidene and isopropylidene.

$R^{42}$ is preferably a hydrogen atom or an alkyl group having 1–3 carbon atoms. Specific examples thereof include a hydrogen atom, methyl, ethyl, n-propyl and isopropyl.

Examples of the hydrocarbon group of $R^{43}$ include alkyl or alkenyl groups having 1–3 carbon atoms. Preferable specific examples thereof include methyl, ethyl, n-propyl, isopropyl, vinyl and allyl groups. The group

which may be indicated by $R^{43}$, may form a salt with sodium, potassium or the like Of these groups indicative of $R^{43}$, a hydrogen atom and methyl group are particularly preferred.

As the hydrocarbon groups represented by $R^{44}$, $R^{47}$, $R^{48}$, $R^{49}$ and $R^{50}$, are preferred alkyl, alkenyl, aryl or aralkyl groups having 1–10 carbon atoms, which may have one or more hydroxyl groups. Further preferable examples thereof include alkyl groups having 1–6 carbon atoms, such as methyl, ethyl, propyl, butyl, pentyl and hexyl groups; phenyl group, benzyl group, and alkyl groups having 1–6 carbon atoms, which have been substituted by 1–6 hydroxyl groups, such as 2-hydroxyethyl, 2,3-dihydroxypropyl, 2,3,4-trihydroxybutyl, 2,3,4,5-tetrahydroxypentyl and 2,3,4,5,6-pentahydroxyhexyl groups.

Examples of the hydrocarbon groups represented by $R^{45}$ and $R^{46}$, which may have 1–3 hydroxyl groups, include alkyl and alkenyl groups having 1–3 carbon atoms, and groups derived from these groups, which have been substituted by 1–3 hydroxyl groups. Specific examples thereof include methyl, ethyl, n-propyl, isopropyl, allyl, hydroxymethyl and 2-hydroxyethyl groups. Of these groups indicative of $R^{45}$ and $R^{46}$, methyl, ethyl, n-propyl and 2-hydroxyethyl groups are preferred, with a methyl group being particularly preferred.

Examples of the hydrocarbon groups represented by $Y^1$ and having 1–10 carbon atoms include alkyl, alkenyl, aryl or aralkyl groups having 1–10 carbon atoms. Examples of alkoxyl, hydroxyalkyloxy and alkoxycarbonyl groups which are substitutable on these hydrocarbon groups include alkoxyl group having 1–6 carbon atoms; hydroxyalkyloxy groups having 1–4 carbon atoms; and alkoxycarbonyl groups having 2–7 carbon atoms, respectively.

In some cases, $Y^1$ may be a group represented by the following formula (a):

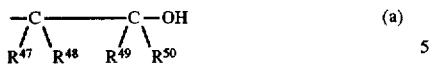

in which $R^{47}$, $R^{48}$, $R^{49}$ and $R^{50}$ have the same meaning as defined above. In the formula (IIa), the case where $Y^1$ is such a group, both $R^{40}$ and $R^{41}$ are methylene, and both $R^{42}$ and $R^{43}$ are hydrogen atoms is excluded. In the formula (a), $R^{47}$ and $R^{48}$ are preferably individually a hydrogen atom, or a hydroxymethyl, methyl, ethyl or 2-hydroxyethyl group, with a hydrogen atom, or a methyl or hydroxymethyl group being particularly preferred. Besides, $R^{49}$ and $R^{50}$ are preferably individually a hydrogen atom, or a hydroxymethyl or 1,2,3,4-tetrahydroxybutyl group, with a hydrogen atom being particularly preferred.

Preferable specific examples of $Y^1$ include groups such as —(CH$_2$)$_2$OH, —(CH$_2$)$_3$—OH, —(CH$_2$)$_6$OH,

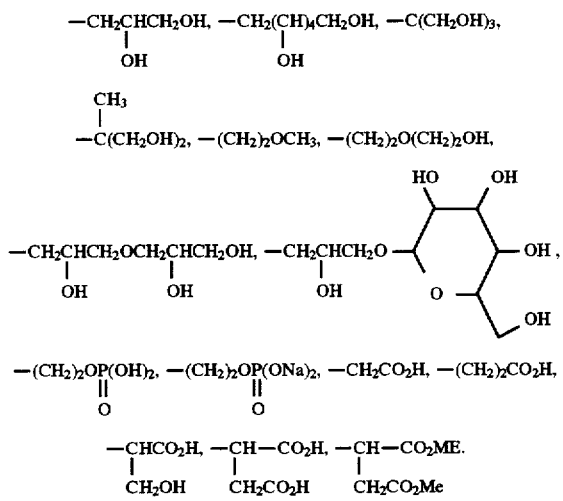

The amine derivatives (IIb) have a quaternary ammonium structure. Examples of counter ions thereof include inorganic ions such as chlorine, sulfuric acid, nitric acid and phosphoric acid, and ions of organic acids such as succinic acid, fumaric acid, lactic acid, glycolic acid, citric acid, tartaric acid and benzoic acid.

In each of the general formulae (IIa) and (IIb), compounds in which $Y^1$ is a group represented by the formula (a) are preferred. Of these, those in which $R^{39}$ is a linear, branched or cyclic hydrocarbon group having 1–25 carbon atoms, which may contain a heteroatom, $R^{43}$ is a hydrogen atom or a hydrocarbon group having 1–3 carbon atom, $R^{44}$ or $R^{45}$ and $R^{46}$ are individually a hydrocarbon group having 1–3 carbon atoms, which may have at least one hydroxyl group, and $R^{47}$, $R^{48}$, $R^{49}$ and $R^{50}$ are individually a hydrogen atom or a hydrocarbon group having 1–10 carbon atoms, which may have one or more hydroxyl groups are preferred.

Those in which $R^{39}$ is a linear or branched hydrocarbon group having 1–22 carbon atoms, which may contain an oxygen atom, $R^{43}$ is a hydrogen atom or a methyl group, $R^{44}$ or $R^{45}$ and $R^{46}$ are individually a hydrocarbon group having 1–3 carbon atoms, $R^{47}$ and $R^{48}$ are individually a hydrogen atom or a methyl or hydroxymethyl group, and $R^{49}$ and $R^{50}$ are individually a hydrogen atom are further preferred.

Those in which $R^{39}$ is a 12-hydroxyoctadecyl group, $R^{43}$ is a hydrogen atom, $R^{44}$ or $R^{45}$ and $R^{46}$ are individually a hydrocarbon group having 1–3 carbon atoms, $R^{47}$ and $R^{48}$ are individually a hydrogen atom or a methyl or hydroxym-ethyl group, and $R^{49}$ and $R^{50}$ are individually a hydrogen atom are further preferred. (IIc):

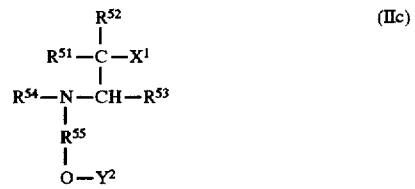

wherein $R^{51}$ means a hydrogen atom or a linear, branched or cyclic hydrocarbon group having 1–40 carbon atoms, $R^{52}$ denotes a hydrogen atom or a hydrocarbon group having 1–5 carbon atoms, which may have one or more hydroxyl groups, $R^{53}$ stands for a hydrogen atom or a hydrocarbon group having 1–22 carbon atoms, which may have one or more hydroxyl or alkoxyl groups, $R^{54}$ represents a hydrogen atom or a hydrocarbon group having 1–7 carbon atoms, which may have one or more hydroxyl groups, $R^{55}$ means a hydrogen atom or a hydrocarbon group having 2–6 carbon atoms, which may have one or more hydroxyl groups, $X^1$ denotes a hydrogen atom, hydroxyl group or

and $Y^2$ represents a hydrogen atom or

In the formula (IIc), the hydrocarbon group represented by $R^{51}$ may be either saturated or unsaturated. Preferable specific examples thereof include groups such as methyl, ethyl, propyl, butyl, hexyl, octyl, decyl, dodecyl, tetradecyl, hexadecyl, eicosyl, methyl-branched isopalmityl, 7-hexadecenyl, 4,8,12-trimethyltridecyl, 4-methyl-3-pentenyl, cyclohexyl and phenyl.

Preferable examples of the hydrocarbon group represented by $R^{52}$ include groups such as methyl, ethyl, butyl, pentyl, hydroxymethyl, 2-hydroxyethyl, 3-hydroxypropyl, 4-hydroxybutyl and 5-hydroxypentyl.

Preferable examples of the hydrocarbon group represented by $R^{53}$ include groups such as methyl, ethyl, butyl, hexyl, phenyl, benzyl, hydroxymethyl, 2-hydroxyethyl, 1,2-dihydroxyethyl, 1,2,3-trihydroxypropyl, 1,2,3,4-tetrahydroxybutyl, 1,2,3,4,5-pentahydroxypentyl, methoxymethyl, dodecyloxymethyl, tetradecyloxymethyl and methyl-branched isostearyloxy.

Preferable examples of the hydrocarbon group represented by $R^{54}$ include groups such as methyl, ethyl, butyl, hexyl, phenyl, benzyl, hydroxymethyl, 2,3-dihydroxypropyl, 2,3,4-trihydroxybutyl, 2,3,4,5-tetrahydroxypentyl and 2,3,4,5,6-pentahydroxyhexyl. Preferable groups as $R^{55}$ include —(CH$_2$)$_2$—, —(CH$_2$)$_3$—, —(CH$_2$)$_4$—, —(CH$_2$)$_5$—, —(CH$_2$)$_6$—,

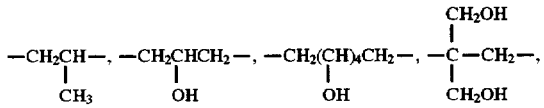

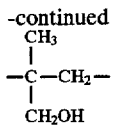

and the like.

In the general formula (IIc), the phosphoric acid residue, which may be indicated by $X^1$ and $Y^2$, may form a salt with a metal or amine. (IId):

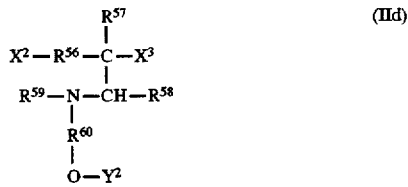

wherein $R^{56}$ means a linear or branched hydrocarbon group having 8–40 carbon atoms, which may have a hydroxyl group. $R^{57}$, $R^{58}$ and $R^{59}$ are identical with or different from each other and denote individually denotes a hydrogen atom or a hydrocarbon group having 1–7 carbon atoms, which may have one or more hydroxyl groups. $R^{60}$ stands for a hydrocarbon group having 2–6 carbon atoms, which may have one or more hydroxyl or alkoxyl groups. $X^2$ is —$OR^{61}$, —$CO_2R^{62}$ or

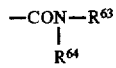

($R^{61}$, $R^{62}$, $R^{63}$ and $R^{64}$ are identical with or different from one another and denote individually a hydrogen atom or a hydrocarbon group having 1–20 carbon atoms, which may contain an oxygen atom), and $Y^3$ represents a hydrogen atom or a hydroxyl group.

In the general formula (IId), the divalent hydrocarbon group indicated by $R^{56}$ may be either saturated or unsaturated. Specific examples thereof include groups such as octamethylene, nonamethylene, decamethylene, undecamethylene, dodecamethylene, tridecamethylene, tetradecamethylene, hexadecamethylene, triacontamethylene, hexadecane-1,10-diyl, 7-hexadecene-1, 10-diyl, 2-hydroxyundecane-1,11-diyl, 2-hydroxytridecane-1,13-diyl and 2-hydroxytetradecane-1, 14-diyl.

Preferable examples of $R^{57}$, $R^{58}$ and $R^{59}$ include a hydrogen atom and groups such as methyl, ethyl, butyl, hexyl, phenyl, benzyl, hydroxymethyl, hydroxyethyl, 1,2-dihydroxyethyl, 1,2,3-trihydroxypropyl, 1,2,3,4-tetrahydroxybutyl and 1,2,3,4,5-pentahydroxypentyl.

Preferable groups as $R^{60}$ include —(CH$_2$)$_2$—, —(CH$_2$)$_3$—, —(CH$_2$)$_4$—, —(CH$_2$)$_5$—, —(CH$_2$)$_6$—,

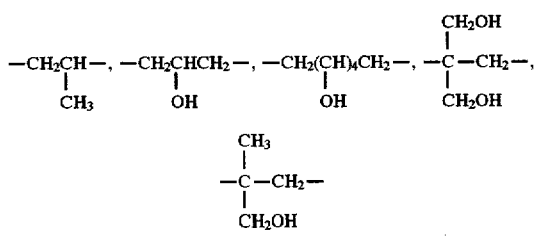

and the like.

In the general formula (IId), the hydrocarbon groups having 1–20 carbon atoms represented by $R^{61}$, $R^{62}$, $R^{63}$ and $R^{64}$, which may contain an oxygen atom, may be any of linear, branched and cyclic hydrocarbon groups. Preferable specific examples thereof include a hydrogen atom, and groups such as methyl, ethyl, butyl, hexyl, octyl, dodecyl, hexadecyl, octadecyl, 2-ethylhexyl, allyl, 2-hydroxyethyl, 2,3-dihydroxypropyl, 2-hydroxypropyl, 6-hydroxyhexyl, 9-hydroxynonyl, 12-hydroxydodecyl, phenyl, benzyl and tetrahydropyranyl.

In the general formula (IId), amine derivatives (IId') in which $R^{56}$ is a linear or branched hydrocarbon group having 8–40 carbon atoms, and $Y^3$ is a hydroxyl group, and amine derivatives (IId") in which $R^{56}$ is an undecamethylene, dodecamethylene, tridecamethylene or tetradecamethylene group, $X^2$ is a hydroxyl group, and $Y^3$ is a hydrogen atom are novel compounds. Therefore, the present invention also provides such compounds or acid-added salts thereof. (IIe):

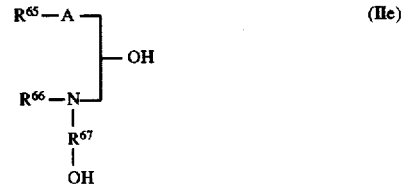

wherein $R^{65}$ means a linear, branched or cyclic hydrocarbon group having 1–40 carbon atoms, which may contain a heteroatom. $R^{66}$ and $R^{68}$ are identical with or different from each other and denote individually a hydrogen atom or a hydrocarbon group having 1–10 carbon atoms, which may have a hydroxyl group. $R^{67}$ stands for a hydrocarbon group having 2–10 carbon atoms, which may be substituted by a hydroxyl group, and A represents —$CO_2$—, —S— or

The heteroatom contained in $R^1$ of the amine derivatives represented by the general formula (IIe) is preferable O, S, N, Si or the like.

In the general formula (IIe), $R^{65}$ is a saturated or unsaturated hydrocarbon. Specific example thereof include groups such as methyl, ethyl, propyl, butyl, hexyl, octyl, decyl, dodecyl, tetradecyl, pentadecyl, hexadecyl, octadecyl, docosyl, dotriacontyl, methyl-branched isostearyl, 2-ethylhexyl, 2-heptylundecyl, 5,7,7-trimethyl-2-(1,3,3-trimethylbutyl)octyl, 9-octadecenyl, 9,12-octadecadienyl, cyclohexyl, phenyl, benzyl, cholesteryl, 12-hydroxyoctadecyl, 12-hydroxydodecyl, 9-hydroxynonyl, 9,10-dihydroxyoctadecyl, 12-hydroxy-9-octadecenyl, 12-methoxy-octadecyl, 10-(2-ethylhexyloxy)decyl, 11-carboxyundecyl, 11-butoxycarbonylundecyl, 11-(2-ethylhexanoylamino)undecyl, 11-(butyldimethylsilyl) undecyl, tocopheryl and 9,10-isopropylidenedioxyoctadecyl.

In the general formula (IIe), as $R^{66}$ and $R^{68}$ are preferred a hydrogen atom, and groups such as methyl, ethyl, butyl, hexyl, phenyl, benzyl, 2-hydroxyethyl, 2,3-dihydroxypropyl, 2,3,4-trihydroxybutyl, 2,3,4,5-tetrahydroxypentyl and 2,3,4,5,6-pentahydroxyhexyl.

Preferable examples of the hydrocarbon group represented by $R^{67}$ include —(CH$_2$)$_2$—, —(CH$_2$)$_3$—, —(CH$_2$)$_4$—, —(CH$_2$)$_5$—, —(CH$_2$)$_6$—,

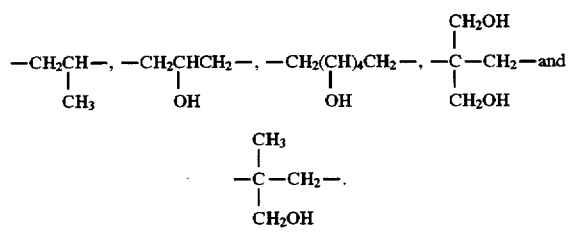

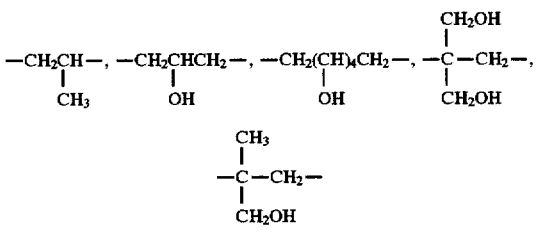

and the like.

In the general formula (IIf), m is particularly preferably 2 or 3.

Of these compounds represented by the general formula (IIf), those in which $R^{69}$ is a linear or branched hydrocarbon group having 7-24 carbon atoms and containing an oxygen atom are particularly preferred. (IIg):

(IIg)

wherein $R^{73}$ means a linear, branched or cyclic hydrocarbon group having 1–40 carbon atoms, which may have a hydroxyl group.

$X^3$ denotes $-CH_2OH$, $-CO_2H$ or $-CH_2OP(OH)_2$, and $\overset{\|}{O}$ $Y^4$ stands for $-NH_2$, $-NHCH_3$, $-N(CH_3)_2$ or $-\overset{\oplus}{N}(CH_3)_3$.

In the general formula (IIg), the hydrocarbon group indicated by $R^{73}$ may be either saturated or unsaturated. Preferable specific examples thereof include groups such as 1-pentadecenyl, pentadecyl, 1-hydroxypentadecyl, 1-heptadecenyl, heptadecyl, 1-hydroxyheptadecyl, methyl, ethyl, 1-nonenyl, 1-undecenyl, 1-tridecenyl, 1-nonadecenyl, 11-hydroxyheptadecenyl, 13-hydroxynonadecenyl, 9-methylhexadecyl and 11-methyloctadecenyl.

Four stereoisomers (D-erythro form, D-threo form, L-erythro form and L-threo form) exist in the amine derivatives represented by the general formula (IIg). In the present invention, any of them may be used, or they may be used in any combination thereof.

Of these amine derivatives (IIg), the naturally occurred products are obtained by extracting phospholipid, ceramide or the like, which contains them, from an appropriate tissue (for example, bovine brain), hydrolyzing it and then extracting them with an organic solvent.

Sphingosine analogues (IIg) can be synthesized in accordance with a process described in J. Am. Chem. Soc., Vol. 95, 4098 (1973); J. Lipid Res., Vol. 19, 250 (1978); Tetrahedron Lett., Vol. 29, 239 (1988); Tetrahedron, Vol. 42, 5961 (1986); or the like. The N-methyl-substituted products, N,N-dimethyl-substituted products and N,N,N-trimethyl-substituted products thereof can be synthesized by subjecting these sphingosine analogues to N-methylation in accordance with a process described in Biochemistry, Vol. 7, 2192 (1968) or the like. (IIh):

In the general formula (IIe), those (IIe') in which $R^{65}$ is a linear or branched hydrocarbon group having 7-24 carbon atoms and containing an oxygen atom are novel compounds. Therefore, the present invention also provides such compounds or acid-added salts thereof. Specific examples of such $R^{65}$ include groups such as 12-hydroxy-octadecyl, 12-hydroxydodecyl, 9-hydroxynonyl, 9,10-dihydroxyoctadecyl, 12-hydroxy-9-octadecenyl, 12-methoxyoctadecyl, 10-(2-ethylhexyloxy)decyl, 11-carboxyundecyl, 11-butoxycarbonylundecyl and 11-(2-ethylhexanoylamino)undecyl. (IIf):

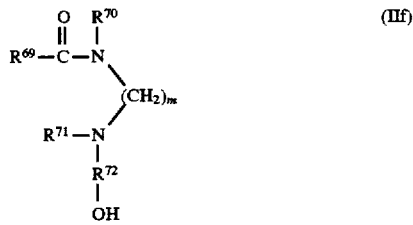

(IIf)

wherein $R^{69}$ means a linear, branched or cyclic hydrocarbon group having 1–40 carbon atoms, which may contain a heteroatom. $R^{70}$ and $R^{71}$ are identical with or different from each other and denote individually a hydrogen atom or a hydrocarbon group having 1–10 carbon atoms, which may have one or more hydroxyl groups. $R^{72}$ represents a hydrocarbon group having 2–6 carbon atoms, which may have one or more hydroxyl groups, and m stands for an integer of 2–6.

Examples of the heteroatom contained in $R^{69}$ of the amine derivatives represented by the general formula (IIf) include oxygen, sulfur, nitrogen and silicon atoms, with an oxygen atom being particularly preferred.

In the general formula (IIf), $R^{69}$ is a saturated or unsaturated hydrocarbon group. Preferable specific examples thereof include groups such as methyl, ethyl, propyl, pentyl, heptyl, nonyl, undecyl, tridecyl, pentadecyl, heptadecyl, hentriacontyl, methyl-branched isoheptadecyl, hepta-3-yl, heptadeca-8-yl, 8-heptadecenyl, 8,11-heptadecadienyl, 9-decenyl, cyclohexyl, phenyl, 8-hydroxyoctyl, 11-hydroxyundecyl, 14-hydroxytetradecyl, 15-hydroxypentadecyl, 11-hydroxyheptadecyl, 8,9-dihydroxyheptadecyl, 11-hydroxy-8-heptadecenyl, 11-methoxyheptadecyl, 9-(2-ethylhexyl)nonyl, 10-carboxydecyl, 10-butoxycarbonyldecyl, 10-(2-ethylhexanoylamino)decyl, 10-(butyldimethylsilyl)decyl and 8,9-isopropylidenedioxyheptadecyl.

As $R^{70}$ and $R^{71}$, are preferred a hydrogen atom, and groups such as methyl, ethyl, butyl, hexyl, phenyl, benzyl, 2-hydroxyethyl, 2,3-dihydroxypropyl, 2,3,4-trihydroxybutyl, 2,3,4,5-tetrahydroxypentyl and 2,3,4,5,6-pentahydroxyhexyl.

In the general formula (IIf), preferable groups as $R^{67}$ include $-(CH_2)_2-$, $-(CH_2)_3-$, $-(CH_2)_4-$, $-(CH_2)_5-$, $-(CH_2)_6-$,

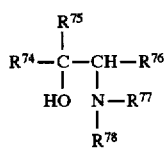

$$\begin{array}{c} R^{75} \\ | \\ R^{74}-C-CH-R^{76} \\ | \quad | \\ HO \quad N-R^{77} \\ | \\ R^{78} \end{array} \qquad \text{(IIh)}$$

wherein $R^{74}$ and $R^{75}$ mean individually a hydrogen atom or a hydrocarbon group having 1–40 carbon atoms, which may have a hydroxyl, carboxyl, alkoxyl, alkylthio, acylamino or acyloxy group, $R^{76}$ denotes a hydrogen atom or a hydrocarbon group having 1–40 carbon atoms, which may have an alkoxyl, alkylthio, acylamino or acyloxy group, or a hydrocarbon group having 1–40 carbon atoms, which may have a hydroxyl or carboxyl group, with the proviso that the total number of carbon atoms contained in $R^{74}$, $R^{75}$ and $R^{76}$ is at least 5, and $R^{77}$ and $R^{78}$ stand individually for a hydrogen atom, a hydrocarbon group having 1–10 carbon atoms or a nitrogen atom, or may form a heterocyclic ring, which may contain an oxygen atom, together with the adjacent nitrogen atom.

In the general formula (IIh), preferable examples of $R^{74}$ and $R^{75}$ include a hydrogen atom, and groups such as methyl, ethyl, decyl, dodecyl, tetradecyl, hexadecyl, cyclohexyl, phenyl, hydroxymethyl, 1-hydroxydodecyl, 1-hydroxytetradecyl, 1-hydroxyhexadecyl, 9-hydroxynonyl, 13-hydroxytridecyl, 14-hydroxytetradecyl, carboxy, 8-carboxyoctyl, 12-carboxydodecyl, 13-carboxytridecyl, dodecyloxymethyl, tetradecyloxymethyl, hexadecyloxymethyl, methyl-branched isostearyloxymethyl, 12-hydroxyoctadecyloxymethyl, 15-hydroxypentadecyloxymethyl, 9-(2-ethylhexyloxy) nonyloxymethyl, dodecylthiomethyl, tetradecylthiomethyl, dodecanoylaminomethyl, tetradecanoylaminomethyl, hexadecanoylaminomethyl, methyl-branched isostearoylaminomethyl, 12-hydroxyoctadecanoylaminomethyl, 15-hydroxypentadecanoylaminomethyl, 16-hydroxyhexadecanoylaminomethyl, 12-(2-ethylhexyloxy)dodecanoylaminomethyl, 11-(2-ethylhexanoylamino)undecanoylaminomethyl, dodecanoyloxymethyl, tetradecanoyloxymethyl, methyl-branched isostearoyloxymethyl and 2-ethylhexyloxymethyl.

Of the specific examples mentioned as $R^{74}$ and $R^{75}$, those other than hydroxymethyl and carboxyl groups are preferred as $R^{76}$. The total number of carbon atoms contained in $R^{74}$, $R^{75}$ and $R^{76}$ is preferably at least 5.

Preferable examples of $R^{77}$ and $R^{78}$ include a hydrogen atom, groups such as methyl, ethyl, propyl, hexyl, cyclohexyl, phenyl and benzyl, and the following groups formed together by $R^{77}$ and $R^{78}$:

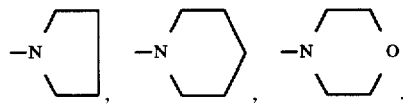

These amine derivatives (I) or (II) may be converted into acid-added salts by reacting an amine derivative (I) or (II) with an acid in accordance with the method known per se in the art. More specifically, they may be converted into salts with an inorganic acid such as hydrochloric acid, sulfuric acid, nitric acid or phosphoric acid, or salt with an organic acid such as succinic acid, fumaric acid, hexadecanoic acid, octadecanoic acid, lactic acid, glycolic acid, citric acid, tartaric acid or benzoic acid. They may also be converted into quaternized products by reacting them with a lower alkyl halide.

Since the amine derivative (I) or (II), or an acid-added salt or quaternized product thereof has an effect of preventing the occurrence of wrinkles and smoothing or removing the wrinkles, this can be applied to the skin, thereby smoothing or removing wrinkles, and so it can be used as an agent for preventing or smoothing wrinkles.

Such an agent for wrinkles may be administered in any way, for example, internal use, external application or the like. As other effective ingredients, antiphlogistics, vitamins and the like, which are routinely used, may be suitably incorporated in addition to the amine derivative (I) or (II), or the acid-added salt or quaternized product thereof as needed.

On the other hand, the amine derivative (I) or (II), or the acid-added salt or quaternized product thereof has effects of inhibiting the synthesis of epidermic cell DNA, facilitating embryonic induction and inhibiting epidermis hypertrophy. Namely, since it has an effect of normalizing the abnormal keratinization of epidermis cells, it can be applied to the skin, thereby improving keratinization. Therefore, it can be used as a keratinization-improving agent.

The amine derivative (I) or (II), or the acid-added salt or quaternized product thereof also has an effect (beautifying effect) of facilitating the keratinization of the skin and hence has an effect of accelerating the metabolism of melanin which is a causative substance of pigmentation in the skin caused by sunburn or the like, thereby improving the pigmentation in the skin. It can thus be used as a beautifier.

As with the agent for preventing or smoothing wrinkles, the keratinization-improving agent and beautifier may be administered in any way, for example, internal use, external application or the like. As other effective ingredients, antiphlogistics, vitamins and the like, which are routinely used, may be suitably incorporated in addition to the amine derivative (I) or (II), or the acid-added salt or quaternized product thereof as needed.

The amine derivative (I) or (II), or the acid-added salt or quaternized product thereof is incorporated as an effective ingredient into a dermatologic preparation (external skin care preparation). The dermatologic preparation may be used in various forms such as medicinal dermatologic preparations, cosmetic dermatologic preparations and cosmetic compositions.

Examples of the medicinal and cosmetic dermatologic preparations include various ointments containing one or more medicinally-effective ingredients.

Ointments include both those containing an oily base as a base and those containing an oil/water or water/oil emulsion-type base as a base. No particular limitation is imposed on the oily bases. For example, plant oils, animal oils, synthetic oils, fatty acids, natural and synthetic glycerides, etc. may be mentioned. No particular limitation is imposed on the medicinally-effective ingredients. For example, one or more of analgesic and antiphlogistic agents, analgesics, disinfectants, astringents, emollients, hormones, vitamins and the like may be used suitably as needed.

When used as a cosmetic composition, it is possible to incorporate those ingredients employed routinely as cosmetic ingredients such as oily substances, moisturizers, ultraviolet absorbents, beautifiers, alcohols, chelating agents, pH adjustors, antiseptics, thickeners, coloring matters, perfume bases, vegetable extracts and the like in combination as needed.

As cosmetics, cosmetic compositions of various forms and uses may be formulated including, for example, oil/water or water/oil type emulsified cosmetics, creams, cosmetic emulsions, toilet waters, oily cosmetics, lip sticks, foundations, skin cleansing compositions, hair tonics, hair styling compositions, hair grooming compositions, hair growth stimulants and bath additive compositions. The dermatologic preparations according to the present invention may be formulated into the above various forms by the conventional methods.

No particular limitation is imposed on the proportion of the amine derivative (I) or (II), or the acid-added salt or quaternized product thereof in the dermatologic preparations. In the case of the emulsion-type dermatologic preparation, however, its proportion may preferably be 0.0001–5 wt. % (hereinafter indicated merely by "%"), more preferably 0.0001–1%, particularly 0.0001–0.1% of the total weight of the composition. In the case of the oil-based dermatologic preparation containing a liquid hydrocarbon such as squalane on the other hand, its proportion may preferably be 0.0001–10%, more preferably 0.0001–1%, particularly 0.0001–0.1% of the total weight of the composition.

EXAMPLES

The present invention will hereinafter be described further by the following examples.

Example 1

Preparation of 1-(2-hydroxyethylamino)-3-(12-hydroxyoctadecyloxy)-2-propanol (1a-1):

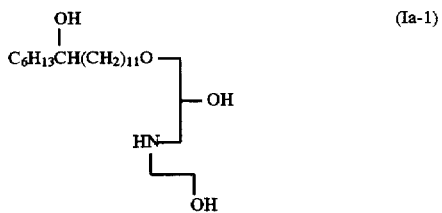

(1) Preparation of 1,12-octadecanediol:

A 5-liter flask equipped with a stirrer, dropping funnel and reflux tube was charged with 28.5 g (0.75 mol) of LiAlH$_4$ and 2 liters of tetrahydrofuran, to which a solution of 237.0 g (0.75 mol) of methyl 12-hydroxyoctadecanate in 1 liter of tetrahydrofuran was added dropwise over 5 hours with stirring. After completion of the dropping, the stirring was continued further for 1 hour at 65° C. After the reaction mixture was then cooled, 90 ml of a 5% aqueous solution of KOH were added with stirring. A salt precipitated was separated by filtration, and the resultant solution was concentrated under reduced pressure. The resulting residue was purified by column chromatography on silica gel, thereby obtaining 185.7 g (yield: 86.6%) of 1,12-octadecanediol.

(2) Preparation of 12-hydroxyoctadecyl glycidyl ether:

A 1-liter flask equipped with a stirrer, dropping funnel and reflux tube was charged with 100 g (0.35 mol) of 1,12-octadecanediol obtained above, 66.8 g (0.72 mol) of epichlorohydrin, 5.68 g (17.6 mmol) of tetrabutylammonium chloride, 50 ml of tetrahydrofuran and 50 ml of toluene. While stirring the mixture, 117 g (1.40 mol) of a 48% aqueous solution of NaOH were added dropwise over 1 hour at 50° C. After stirring for 1 hour at 50° C., the mixture was added with 400 ml of water and subjected to extraction with isopropyl alcohol. After the solvent was distilled off under reduced pressure, the resultant residue was purified by column chromatography on silica gel, thereby obtaining 47.0 g (yield: 45%) of 12-hydroxyoctadecyl glycidyl ether.

(3) Preparation of 1-(2-hydroxyethylamino)-3-(12-hydroxyoctadecyloxy)-2-propanol (Ia-1):

A 200-ml flask equipped with a stirrer, reflux condenser and dropping funnel was charged with 35.0 g (0.57 mol) of ethanolamine and 35 g of ethanol, and the mixture was heated to 80° C. with stirring in a nitrogen atmosphere. To this mixture, 13.0 g (38 mmol) of 12-hydroxyoctadecyl glycidyl ether were added dropwise over 3 hours. After the resultant mixture was stirred further for 3 hours, it was concentrated under reduced pressure and purified by column chromatography on silica gel, thereby obtaining 11.7 g (yield: 77%) of the title compound (Ia-1).

Colorless powder.
Melting point: 71.8°–72.5° C.
IR (KBr, cm$^{-1}$): 3298, 2920, 2848, 1470, 1341, 1122, 906, 852.
$^1$H-NMR (CDCl$_3$, δ): 0.88(t,J=6.43 Hz,3H), 1.10–1.70 (m,30H), 2.52–3.15(m,8H), 3.30–3.54(m,7H), 3.82–4.00(m, 1H).

Examples 2–4

Reactions were conducted in the same manner as in Example 1 except that N-methylethanolamine, diethanolamine and 2-amino-2-methyl-1,3-propanediol were respectively used in place of ethanolamine in the step (3) of Example 1, thereby preparing the following amine derivatives (Ia-2)–(Ia-4).

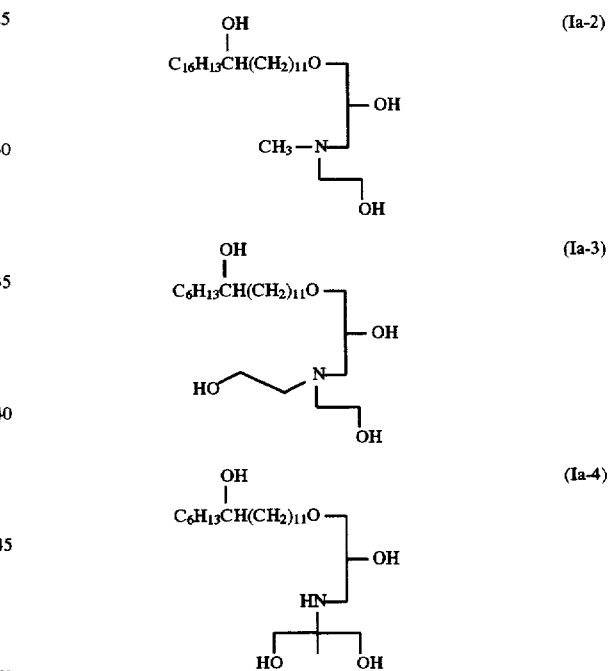

(Ia-2):
Colorless powder.
Melting point: 69.5°–71.7° C.
IR (NaCl, cm$^{-1}$): 3304, 2924, 2852, 1464, 1346, 1124, 1032.
$^1$H-NMR (CDCl$_3$, δ): 0.81–0.96(m,3H), 1.13–1.67(m, 30H), 2.33(s,3H), 2.38–3.20(m,7H), 3.33–3.69(m,7H), 3.82–3.98(m,1H).
(Ia-3):
colorless wax.
Melting point: 40.6°–43.6° C.
IR (KBr, cm$^{-1}$): 3340, 2924, 2852, 1468, 1116, 1074, 868.
$^1$H-NMR (CDCl$_3$, δ): 0.88(t,J=6.7 Hz, 3H), 1.03–1.82(m, 30H), 2.32–2.87(m,6H) , 3.30–4.40(m,10H).
(Ia-4):
Colorless powder.
Melting point: 63.2°–64.1° C.

IR (NaCl, cm$^{-1}$): 3320, 2912, 1458, 1380, 1118, 1046.

$^1$H-NMR (CDCl$_3$, δ): 0.82–0.97(m,3H), 1.10(s,3H), 1.18–1.67(m,30H), 2.72–3.06(m,2H), 3.41–3.79(m,9H), 3.79–4.92(br,6H).

Examples 5–7

Reactions were conducted in the same manner as in Examples 1 and 2 except that ethyl ricinolate was used in place of methyl 12-hydroxyoctadecanate in Examples 1 and 2, thereby preparing the following amine derivatives (Ia-5)–(Ia-7).

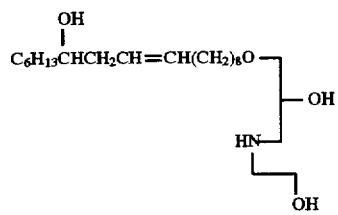

(Ia-5)

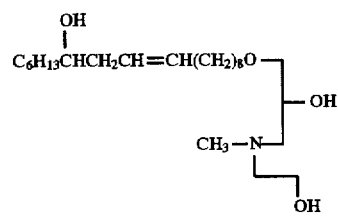

(Ia-6)

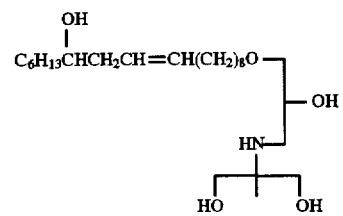

(Ia-7)

(Ia-5):

Yellow oil.

IR (NaCl, cm$^{-1}$): 3372, 2924, 2856, 1454, 1370, 1116, 1056.

$^1$H-NMR (CDCl$_3$, δ): 0.75–1.02(m,3H), 1.08–1.70(m, 22H), 1.90–2.30(m,4H), 2.48–2.84(m,4H), 3.08(brs,4H), 3.38–3.75(m,7H), 3.80–4.02(m,1H), 5.28–5.62(m,2H).

(Ia-6):

Pale yellow oil.

IR (NaCl, cm$^{-1}$): 3404, 2924, 2856, 1456, 1362, 1120, 1080, 1034.

$^1$H-NMR (CDCl$_3$, δ): 0.81–0.96(m,3H), 1.12–1.67(m, 22H), 1.96–2.13(m,2H), 2.21(t,J=6.6 Hz,2H), 2.34(s,3H), 2.37–2.77(m,7H), 3.32–3.53(m,4H), 3.53–3.62(m,3H), 3.82–3.97(m,1H), 5.30–5.63(m,2H).

(Ia-7):

Pale yellow oil.

IR (NaCl, cm$^{-1}$): 3352, 2924, 2856, 1458, 1360, 1116, 1040.

$^1$H-NMR (CDCl$_3$, δ): 0.80–1.04(m,3H), 0.97(s,3H), 1.10–1.66(m,22H), 1.94–2.13(m,2H), 2.21(t,J=6.6 Hz,2H), 2.53–2.82(m,2H), 2.82–3.69(m,14H), 3.83–4.00(m,1H), 5.28–5.64(m,2H).

Example 8

A reaction was conducted in the same manner as in Example 1 except that methyl 9,10-dihydroxyoctadecanate was used in place of methyl 12-hydroxyoctadecanate in Example 1, thereby preparing the following amine derivative (Ia-8).

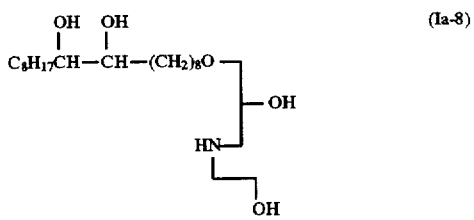

(Ia-8):

Colorless powder.

Melting point: 108.9°–109.8° C.

IR (NaCl, cm$^{-1}$): 3300, 2920, 2852, 1466, 1118, 1066.

$^1$H-NMR (CDCl$_3$, δ): 0.88(t,J=6.4 Hz,3H), 1.04–1.90(m, 28H), 2.46–3.02(m,9H), 3.18–4.00(m,9H).

Examples 9–10

Reactions were conducted in the same manner as in Example 1 except that 1,12-dodecanediol and 1,9-nonanediol were respectively used in place of 1,12-octadecanediol in the step (2) of Example 1, thereby preparing the following amine derivatives (Ia-9)–(Ia-10).

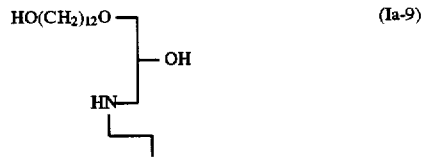

(Ia-9)

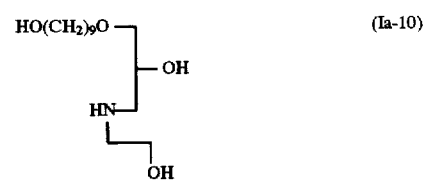

(Ia-10)

(Ia-9):

Colorless powder.

Melting point: 77.8°–78.58° C.

IR (NaCl, cm$^{-1}$): 3396, 2916, 2852, 1464, 1116, 1050.

$^1$H-NMR (CDCl$_3$, δ): 1.00–1.88(m,20H), 2.05–2.88(m, 8H), 3.10–4.05(m,9H).

(Ia-10):

Colorless powder.

Melting point: 68.6°–70.8° C.

IR (NaCl, cm$^{-1}$): 3380, 3308, 2916, 2852, 1462, 1356, 1116, 1066, 954, 864, 720.

$^1$H-NMR (CDCl$_3$, δ): 1.13–1.77(m,14H), 2.56–2.90(m, 4H), 3.30–3.99(m,9H).

Example 11

A reaction was conducted in the same manner as in Example 1 except that methyl 9,10-epoxyoctadecanate was used in place of methyl 12-hydroxyoctadecanate in Example 1, thereby preparing the following amine derivative (Ia-11).

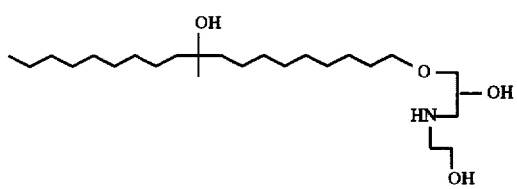

(Ia-11):
Colorless powder.
Melting point: 75.7°–78–8° C.
IR (NaCl, cm$^{-1}$) : 3376, 2920, 2852, 1466, 1122, 1052.
$^1$H-NMR (CDCl$_3$, δ): 0.88(t,J=6.4 Hz,3H), 1.16–2.50(m, 34H), 2.55–2.86(m,4H), 3.28–4.00(m,4H).

Example 12

Preparation of 1-(2-hydroxyethylamino)-3-(2-hydroxyoctadecyloxy)-2-propanol (Ia-12):

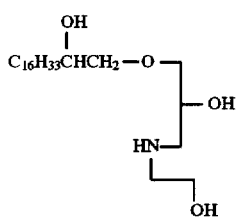

(1) Preparation of 2-hydroxyoctadecyl glycidyl ether:

A 300-ml flask equipped with a stirrer and reflux tube was charged with 58 g (1 mol) of allyl alcohol, to which 0.4 g (10 mmol) of 60% NaH were added to completely dissolve it in the alcohol. Then, 26.9 g (0.1 mol) of 1,2-epoxyoctadecane were added to the solution. The resultant mixture was heated and stirred for 6 hours at 100° C. After completion of the reaction, the reaction mixture was neutralized with hydrochloric acid and subjected to extraction with chloroform. After the solvent was distilled off under reduced pressure, the resultant residue was purified by column chromatography on silica gel, thereby obtaining 31.1 g (yield: 95%) of 1-allyloxy-2-octadeoanol.

A flask equipped with a stirrer was then charged with 31.1 g (95 mmol) of 1-allyloxy-2-octadecanol obtained above, 25.9 g (0.15 mmol) of m-chloroperbenzoic acid and 100 ml of diohloromethane, and the contents were stirred for 36 hours at room temperature. After solids precipitated were separated by filtration, the solvent was distilled off under reduced pressure, and the resultant residue was purified by column chromatography on silica gel, thereby obtaining 24.9 g (yield: 76.5%) of 2-hydroxyoctadecyl glycidyl ether.
(2) Preparation of 1-(2-hydroxyethylamino)-3-(2-hydroxyoctadecyloxy)-2-propanol (1-l):

A 300-ml flask equipped with a stirrer, reflux tube and dropping funnel was charged with 40.5 g (0.66 mol) of ethanolamine and 8.6 g of ethanol. While heating and stirring the mixture at 80° C., an ethanol solution of 4.08 g (11.8 mmol) of 2-hydroxyoctadecyl glycidyl ether was added dropwise over 3 hours. After the resultant mixture was heated and stirred further for 3 hours, it was poured into 500 ml of ice water to collect crystals formed by filtration. The thus-obtained crystals were recrystallized again from n-hexane, thereby obtaining 3.58 g (yield: 75%) of the title compound (Ia-12).
(Ia-12):
Colorless powder.
Melting point: 91.8°–92.7° C.
IR (NaCl, cm$^{-1}$) : 3432, 2916, 2848, 1466, 1116, 1046.

$^1$H-NMR (CDCl$_3$, δ): 0.88(t,J=6.4 Hz,3H), 1.00–2.40(m, 34H), 2.58–2.92(m,4H), 3.20–3.85(m,8H).

Example 13

A reaction was conducted in the same manner as in Example 1 except that methyl 12-methoxyoctadecanate was used in place of methyl 12-hydroxyoctadecanate in Example 1, thereby preparing the following amine derivative (Ia-13).

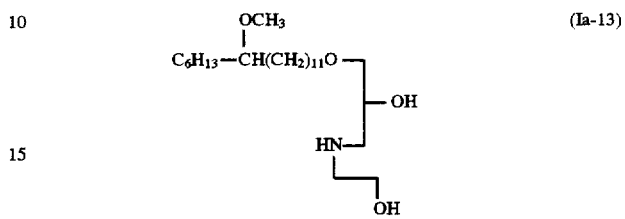

(Ia-13):
Pale yellow oil.
IR (NaCl, cm$^{-1}$) : 3312, 2928, 2856, 1458, 1372, 1100, 942, 856.
$^1$H-NMR (CDCl$_3$, δ): 0.78–1.00(m,3H), 1.08–1.70(m, 30H), 2.50–2.88(m,6H), 2.75–3.52(m,9H), 3.56–3.78(m, 2H), 3.80–4.00(m,1H).

Example 14

Preparation of 1-(2-hydroxyethylamino)-3-[10-(2-ethylhexyloxy)decyloxy]-2-propanol (Ia-14):

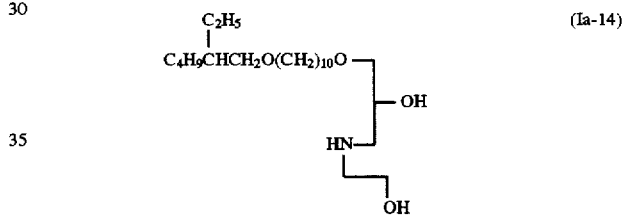

(1) Preparation of 10-(2-ethylhexyloxy)decanol:

A 1-liter flask equipped with a stirrer and distiller was charged with 25 g (0.14 mol) of 1,10-decanediol, 8.09 g (0.14 mol) of KOH and 300 ml of xylene, and the resultant mixture was heated at 120° C. for 1 hour, thereby distilling off water formed. To this reaction mixture, were added 23.1 g (0.12 mol) of 2-ethylhexyl bromide, and the resulting mixture was heated and stirred for 15 hours. After completion of the reaction, the reaction mixture was cooled to room temperature and washed with water. After the solvent was distilled off under reduced pressure, the resulting residue was purified by column chromatography on silica gel, thereby obtaining 24.8 g (yield: 72%) of 10-(2-ethylhexyloxy)decanol.
(2) Preparation of 10-(2-ethylhexyloxy)decyl glycidyl ether:

A 200-ml flask equipped with a stirrer, reflux tube and dropping funnel was charged with 24.8 g (87 mmol) of 10-(2-ethylhexyloxy)decanol, 17.7 g (0.191 mol) of epichlorohydrin, 1.4 g (4.4 mmol) of tetrabutylammonium bromide and 25 ml of hexane. While stirring the mixture at 40° C., 29.2 g (0.35 mol) of a 48% aqueous solution of NaOH were added dropwise over 3 hours. After completion of the dropping, the stirring was continued further for 2 hours at 40° C. After the resultant reaction mixture was washed with water, and the solvent was distilled off under reduced pressure, the resultant residue was purified by column chromatography on silica gel, thereby obtaining 24.6 g (yield: 82.6%) of 10-(2-ethylhexyloxy)decyl glycidyl ether.

(3) Synthesis of 1-(2-hydroxyethylamino)-3-[10-(2-ethylhexyloxy)decyloxy]-2-propanol (Ia-14):

A 200-ml two-necked flask equipped with a stirrer, reflux tube and dropping funnel was charged with 32.7 g (0.54 mol) of ethanolamine and 10.1 g of ethanol. While heating and stirring the mixture at 80° C., 1.76 g (5.14 mmol) of 10-(2-ethylhexyloxy)decyl glycidyl ether were added dropwise over 2 hours. After the resultant mixture was heated and stirred further for 18 hours, it was concentrated under reduced pressure, and the resultant residue was purified by column chromatography on silica gel, thereby obtaining 1.42 g (yield: 68%) of the title compound (Ia-14).
(Ia-14):
Yellow oil.
IR (NaCl, cm$^{-1}$) : 3400, 2924, 2856, 1464, 1114.
$^1$H-NMR (CDCl$_3$, δ): 0.75–1.05(m,6H), 1.10–2.17(m, 25H), 2.50–3.12(m,7H), 3.14–4.15(m,11H).

Example 15

Preparation of butyl 12-[2-hydroxy-3-(2-hydroxyethylamino)propoxy]dodecanate (Ia-15):

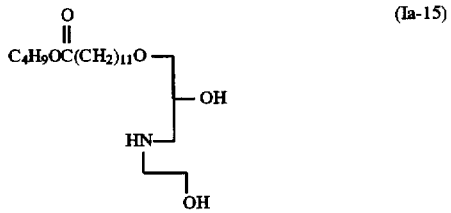

(1) Preparation of butyl 12-(2,3-epoxypropoxy)dodecanate:

A 500-ml flask equipped with a stirrer was charged with 10.8 g (50 mmol) of butyl 12-hydroxydodecanate, 18.2 g (150 mmol) of allyl bromide, 6.0 g (150 mmol) of NaH and 100 ml of dimethylformamide, and the resultant mixture was stirred for 24 hours at 50° C., to which 100 ml of butanol were further added, followed by stirring at 50° C. for 2 hours. The reaction mixture was then added with water and subjected to extraction with isopropyl alcohol, and the solvent was distilled off under reduced pressure.

The thus-obtained residue was then charged into a 100-ml flask, and 10.2 g (50 mmol) of m-chloroperbenzoic acid and dichloromethane were added thereto. The resultant mixture was stirred at room temperature for 48 hours. After separating solids formed, the solvent was distilled off under reduced pressure, and the resultant residue was purified by column chromatography on silica gel, thereby obtaining 8.67 g (yield: 52.8%) of butyl 12-(2,3-epoxypropoxy) dodecanate.

(2) Preparation of butyl 12-[2-hydroxy-3-(2-hydroxyethylamino)propoxy]dodecanate (Ia-15):

A 100-ml flask equipped with a stirrer and dropping funnel was charged with 23.7 g (250 mmol) of ethanolamine and 23.7 g of ethanol. While stirring the mixture at 80° C., an ethanol solution of 8.20 g (25 mmol) of butyl 12-(2,3-epoxypropoxy)-dodecanate was added dropwise over 1 hour. After completion of the reaction, water was added to the reaction mixture, followed by extraction with chloroform. The resultant chloroform solution was concentrated under reduced pressure, and the resultant residue was purified by column chromatography on silica gel, thereby obtaining 5.40 g (yield: 55.4%) of the title compound (Ia-15).
(Ia-15):
Pale yellow solid.
Melting point: 48.6°–50.2° C.

IR (NaCl, cm$^{-1}$) : 3452, 2940, 1728, 1466, 1326, 1116, 1050 862.
$^1$H-NMR (CDCl$_3$, δ): 0.93(t,J=7.2 Hz,3H), 1.21–1.87(m, 22H), 2.29(t,J=7.4 Hz,2H), 2.42–3.03(m,7H), 3.34–3.61(m, 4H), 3.62–3.80(m,2H), 3.82–4.00(m,1H), 4.07(t,J=6.6 Hz,2H).

Example 16

Preparation of 12-[2-hydroxy-3-(2-hydroxyethylamino) propoxy]dodecanoic acid hydrochloride (Ia-16):

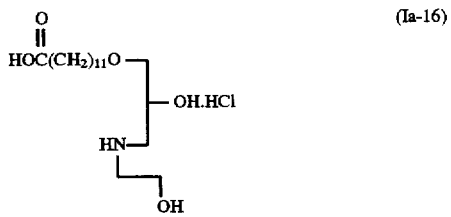

A 200 ml-flask equipped with a stirrer was charged with 3.90 (10 mmol) of the amine derivative (Ia-15) obtained in Example 15, 11 g (0.1 mol) of a 50% aqueous solution of KOH and 100 ml of ethanol. The mixture was stirred at 40° C. for 2 hours. After completion of the reaction, the reaction mixture was acidified with hydrochloric acid, followed by extraction with chloroform. The resultant chloroform solution was treated with active carbon and then concentrated under reduced pressure, thereby obtaining 2.67 g (yield: 72.2%) of the title compound (Ia-16).
(Ia-16):
Pale yellow wax.
IR (NaCl, cm$^{-1}$) : 3264, 3032, 2924, 1724, 1628, 1458, 1116, 1066, 998, 746.
$^1$H-NMR (CDCl$_3$, δ): 1.17–1.70(m,18H), 2.27 (t,J=7.4 Hz,2H), 2.98–3.25(m,4H), 3.38–3.89(m,6H), 3.94–4.16(m, 1H).

Example 17

Preparation of N-[11-[2-hydroxy-3-(2-hydroxyethylamino)propoxy]undecyl]-2-ethylhexanamide (Ia-17):

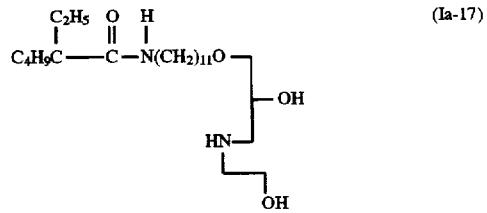

(1) Preparation of N-[11-(2,3-epoxypropoxy)undecyl]-2-ethylhexanamide:

A 200-ml flask equipped with a stirrer and dropping funnel was charged with 9.37 g (50 mmol) of 11-aminoundecanol, 9.48 g (120 mmol) of pyridine and 50 ml of dichloromethane. While stirring the mixture at room temperature, 8.13 g (50 mmol) of 2-ethylhexanoyl chloride were added. After stirring at room temperature for 1 hour, the mixture was added with water and subjected to extraction with chloroform, and the resultant chloroform solution was concentrated under reduced pressure.

The thus-obtained residue was then charged into a 200-ml flask equipped with a stirrer, reflux tube and dropping funnel, and 13.9 g (150 mmol) of epichlorohydrin, 0.81 g (2.5 mmol) of tetrabutylammonium bromide and 20 ml of hexane were added thereto. While stirring the mixture at 40° C., 20.8 g (250 mmol) of a 48% aqueous NaOH were added dropwise to the resultant mixture over 2 hours. After completion of the dropping, the resultant mixture was stirred further for 48 hours at 40° C., washed with water and concentrated under reduced pressure. The resultant residue was then purified by column chromatography on silica gel, thereby obtaining 11.3 g (yield: 61.2%) of N-[11-(2,3-epoxypropoxy)undecyl]-2-ethylhexanamide.

(2) Preparation of N-[12-[2-hydroxy-3-(2-hydroxyethylamino)propoxy]undecyl]-2-ethylhexanamide (Ia-17):

A 100-ml flask equipped with a stirrer, reflux tube and dropping funnel was charged with 16.8 g (0.28 mol) of ethanolamine and 3.4 g of ethanol. While heating and stirring the mixture at 80° C., an ethanol solution of 6.77 g (18.3 mmol) of N-[12-(2,3-epoxypropoxy)undecyl]-2-ethylhexanamide was added dropwise over 3 hours. After the heating and stirring were conducted further for 30 minutes, the reaction mixture was concentrated under reduced pressure, and the resultant residue was purified by column chromatography on silica gel, thereby obtaining 6.47 g (yield: 82%) of the title compound (Ia-17).

(Ia-17):
Colorless solid.
Melting point: 76.1°–77.3° C.
IR (KBr, cm$^{-1}$) : 3300, 3468, 2924, 2856, 1638, 1458, 1376, 1350, 1112, 1042.
$^1$H-NMR (CDCl$_3$, δ): 0.88(t,J=7.3 Hz,6H), 1.08–1.98(m, 26H), 2.50–2.88(m,8H), 3.15–3.55(m,6H), 3.57–3.75(m, 2H), 3.82–3.98(m,1H), 5.46–5.62(m,1H).

Example 18

Preparation of 1-(2-hydroxyethylamino)-3-[11-(butyldimethylsilyl)undecyloxy]-2-propanol (Ia-18):

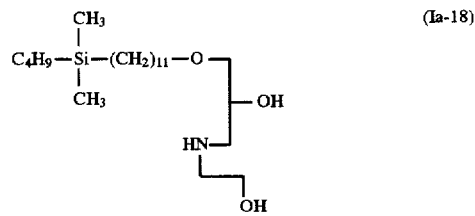

(1) Synthesis of 11-(butyldimethylsilyl)undecyl glycidyl ether:

A 100-ml flask equipped with a stirrer was charged with 13.6 g (60 mmol) of 10-undecenyl glycidyl ether, 5.8 g (50 mmol) of butyldimethylsilane and 4 mg (0.01 mmol) of H$_2$PtCl$_6$. The contents were stirred at 60° C. for 24 hours. The resultant reaction mixture was distilled under reduced pressure (145°–154° C./6×10$^{-3}$ Torr), thereby obtaining 14.15 g (yield: 82.6%) of 11-(butyldimethylsilyl)undecyl glycidyl ether.

(2) Preparation of 1-(2-hydroxyethylamino)-3-[11-(butyldimethylsilyl)undecyloxy]-2-propanol (Ia-18):

A 100-ml two-necked flask equipped with a stirrer, dropping funnel and N$_2$ inlet tube was charged with 4.58 g (75 mmol) of ethanolamine and 9.2 g of ethanol. The contents were heated to 80° C. with stirring in an N$_2$ atmosphere, and an ethanol solution of 1.71 g (5 mmol) of 11-(butyldimethylsilyl)undecyl glycidyl ether was added dropwise to the contents over 1 hour. The resultant mixture was stirred further for 1 hour at 80° C. After completion of the reaction, ethanol and excess ethanolamine were distilled off under reduced pressure, and the resultant residue was purified by column chromatography on silica gel, thereby obtaining 1.48 g (yield: 73%) of the title compound (Ia-18). (Ia-18):

Pale yellow oil.
IR (NaCl, cm$^{-1}$) : 3348, 2924, 2856, 1462, 1248, 1116, 1052, 907, 826, 726.
$^1$H-NMR (CDCl$_3$, δ): -0.13(s,6H), 0.37–0.45(m,4H), 0.81(t,J=6.6 Hz,3H), 1.05–1.62(m,22H), 2.50–2.78(m,4H), 3.23–4.08(m,10H).

Example 19

A reaction was conducted in the same manner as in Example 18 except that 1,1,1,2,3,3,3-heptamethyltrisiloxane was used in place of butyldimethylsilane in Example 18, thereby preparing the following amine derivative (Ia-19).

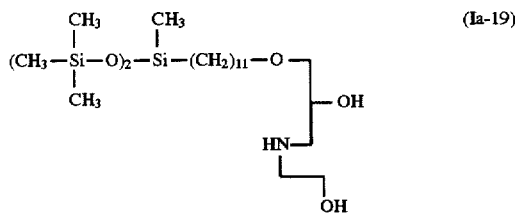

Pale yellow oil.
IR (NaCl, cm$^{-1}$) : 3312, 2924, 2852, 1448, 1348, 1252, 1046, 834.
$^1$H-NMR (CDCl$_3$, δ): -0.06(s,3H), 0.03(s,18H), 0.33–0.46(m,2H), 1.06–1.62(m,14H), 2.51–2.79(m,4H), 3.25–3.96(m,10H).

Example 20

A reaction was conducted in the same manner as in Example 1 except that 3,3,4,4,5,5,6,6,7,7,8,8,8-tridecafluorooctyl glycidyl ether was used in place of 12-hydroxyoctadecyl glycidyl ether in the step (3) of Example 1, thereby preparing the following amine derivative (Ia-20).

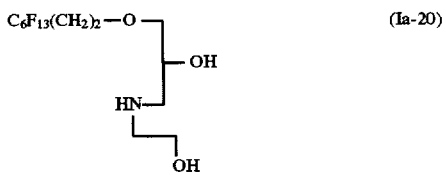

Colorless amorphous.
IR (NaCl, cm$^{-1}$) : 3316, 2908, 1449, 1194, 1143.
$^1$H-NMR (CDCl$_3$, δ): 2.42(tt,J=18.8 Hz,6.7 Hz,2H), 2.58–2.88(m,7H), 3.37–3.58(m,2H), 3.62–4.00(m,7H).

Example 21

Inhibitory effect of the amine derivatives on DNA synthesis of epidermic keratinocyte:

(1) Method:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (Ia-1) to (Ia-20) obtained in the above synthesis examples was added thereto. Further, 0.2 μCi/ml of [$^3$H] thymidine was subsequently added to incubate the culture for 4 hours. After the supernatant was then removed by suction, and the well was washed 3 times with PBS(−), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

(2) Result:

The relative amounts of the [$^3$H] thymidine incorporated at the time each of the amine derivatives (Ia-1) to (Ia-20) has been added in amounts of 10 μM and 100 μM are shown in Table 1.

TABLE 1

| Amine derivative | Relative amount of [$^3$H] thymidine incorporated (%)* | |
|---|---|---|
| | 10 μM | 100 μM |
| (Ia-1) | 21.8 | 8.2 |
| (Ia-2) | 17.3 | 4.4 |
| (Ia-3) | 47.9 | 15.5 |
| (Ia-4) | 25.5 | 8.3 |
| (Ia-5) | 16.4 | 4.2 |
| (Ia-6) | 9.4 | 1.0 |
| (Ia-7) | 31.0 | 13.0 |
| (Ia-8) | 28.3 | 7.9 |
| (Ia-9) | 70.3 | 32.0 |
| (Ia-10) | 75.3 | 30.9 |
| (Ia-11) | 18.7 | 4.2 |
| (Ia-12) | 19.3 | 2.1 |
| (Ia-13) | 11.8 | 1.1 |
| (Ia-14) | 16.1 | 4.2 |
| (Ia-15) | 59.3 | 17.0 |
| (Ia-16) | 98.7 | 13.7 |
| (Ia-17) | 11.0 | 0.9 |
| (Ia-18) | 14.3 | 1.8 |
| (Ia-19) | 51.7 | 21.4 |
| (Ia-20) | 80.2 | 33.5 |

*: Indicating the relative value where a control is assumed to be 100%.

It was apparent from Table 1 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells turn insoluble membrane (cornified envelope), i.e., become keratinized. It is understood from this fact that the amine derivatives according to the present invention are active in facilitating the keratinization of epidermis.

Example 22

Effect of the amine derivatives on the transglutaminase activity of epidermic keratinocyte:

(1) Determination of transglutaminase activity:

Keratinocytes cultured in a vegetative state in a 6-well plate were used. A medium in each well was removed by suction to add 2 ml of K-GM, to which no pituitary gland extract was added, to the well, thereby making a medium exchange. Thereafter, each of the amine derivatives (Ia-2) and (Ia-6) was added thereto. After 24 hours, each well was washed 3 times with PBS(−), and the cells were then separated and collected by a rubber policeman. The thus-obtained cell suspension was centrifuged at 2,500 rpm for 10 minutes to collect the sediment. To this sediment, were added 200 μl of a buffer (a) [10 mM Tris-HCl buffer, 10 mM DTT, 0.5 mM EDTA; pH 7.4], followed by ultrasonication twice for 1 minute. The thus-obtained suspension was centrifuged at 25,000 rpm for 30 minutes to obtain a supernatant. This supernatant was divided into equiamount portions. To each of the portions, was added a reaction solution [a solution obtained by mixing 300 mM Tris-HCl buffer, pH 8.1; 100 μl of 60 mM $CaCl_2$; 100 μl of 30 mM DTT; 100 μl of distilled water containing 540 μg of dimethylcasein; 50 μl of 12 mM putrescine; 50 μl of 2.5 μCi [$^{14}$C] putrescine; and 100 μl of distilled water]. The thus-obtained mixture was incubated at 37° C. for 1 hour. After 600 μl of 10% trichloroacetic acid were then added to the mixture, and the resultant mixture was left at rest for 30 minutes, precipitate was collected on a nitrocellulose membrane of 0.45 μm. After this membrane was washed with 15 ml of 5% trichloroacetic acid (containing 1% of putrescine) chilled with ice water, the radioactivity of the precipitate on the membrane was determined by a liquid scintillation counter.

(2) Result:

The values (dpm) of transglutaminase activities where each of the amine derivatives (Ia-2) and (Ia-6) has been added in an amount of 10 μM are shown in Table 2.

TABLE 2

| | Transglutaminase activity value (dpm) |
|---|---|
| Control | 2752.8 |
| Amine derivative (Ia-2) | 9520.1 |
| Amine derivative (Ia-6) | 13764.0 |

As apparent from the results shown in Table 2, the activity value is increased by adding the amine derivative. Namely, it is understood that the amine derivatives have an embryonic induction activity against keratinocytes.

Example 23

Effect of the amine derivatives on wrinkles formed on hairless mice by exposure to UVB:

(1) Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (Ia-1) to (Ia-18) in a concentration of 0.025% were applied 5 times a week to their corresponding groups of mice for 6 weeks in a dose of 80 μl. As a control, ethanol alone was applied in a dose of 80 μl like the samples.

After completion of the application, the degree of wrinkles was visually observed to rank the samples in accordance with the following standard (wrinkle index). The results are shown in Table 3.

(Wrinkle index)
1: Wrinkles were completely removed;
2: Wrinkles were scarcely observed;
3: Wrinkles were somewhat observed;
4: Wrinkles were observed to a great extent.

(2) In order to further analyze the particulars of wrinkles, skin replicas of the size of 1 cm² in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 3.

TABLE 3

| Amine derivative | Wrinkle index | Area percent by image analysis (%) |
| --- | --- | --- |
| Control | 3.75 ± 0.09 | 6.42 ± 0.63 |
| (Ia-1) | 3.00 ± 0.15 | 4.08 ± 0.43 |
| (Ia-3) | 2.80 ± 0.30 | 2.88 ± 0.21 |
| (Ia-4) | 3.20 ± 0.12 | 3.88 ± 0.38 |
| (Ia-5) | 3.00 ± 0.15 | 3.26 ± 0.31 |
| (Ia-8) | 3.10 ± 0.10 | 3.57 ± 0.34 |
| (Ia-9) | 2.50 ± 0.22 | 1.69 ± 0.16 |
| (Ia-10) | 3.30 ± 0.20 | 4.20 ± 0.37 |
| (Ia-11) | 3.80 ± 0.12 | 5.77 ± 0.56 |
| (Ia-12) | 3.10 ± 0.29 | 3.57 ± 0.33 |
| (Ia-13) | 3.30 ± 0.30 | 4.20 ± 0.40 |
| (Ia-14) | 2.58 ± 0.37 | 1.94 ± 0.15 |
| (Ia-15) | 2.77 ± 0.30 | 2.53 ± 0.22 |
| (Ia-16) | 2.90 ± 0.18 | 2.94 ± 0.21 |
| (Ia-17) | 3.60 ± 0.18 | 5.11 ± 0.56 |
| (Ia-18) | 3.33 ± 0.28 | 4.29 ± 0.41 |

As apparent from the result shown in Table 3, the wrinkles formed on the backs of the hairless mice can be removed by applying the amine derivatives (Ia) thereto.

Example 24

A W/O type cream having the following composition was obtained in accordance with the below-described preparation process.

| (Composition) | (wt. %) |
| --- | --- |
| (1) Amine derivative (Ia-1) | 0.1 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 25

An O/W type cream having the following composition was obtained in accordance with the below-described preparation process.

| (Composition) | (wt. %) |
| --- | --- |
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (Ia-3) | 0.001 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 26

A moisturizing sunscreen cream having the following composition was obtained in accordance with the below-described preparation process.

| (Composition) | (wt. %) |
| --- | --- |
| (1) Amine derivative (Ia-9) | 0.0005 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 27

A pack having the following composition was obtained in accordance with the below-described preparation process.

| (Composition) | (wt. %) |
| --- | --- |
| (1) Amine derivative (Ia-16) hydrochloride | 0.05 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 28

An ointment having the following composition was obtained in accordance with the below-described preparation process.

| (Composition) | (wt. %) |
|---|---|
| (1) Amine derivative (Ia-14) | 0.075 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations according to the present invention, which were prepared in Examples 24–28, had excellent effects of preventing the occurrence of wrinkles and smoothing or removing wrinkles and moreover inhibited parakeratosis of the skin, epidermic hypertrophy and metabolic aberration of lipid and were excellent in recovery of normal functions and maintenance of homeostasis.

Preparation Example 1:

Preparation of 1-(2-hydroxyethylamino)-3-tocopheryloxy-2-propanol (Ib-1):

[In the general formula (Ib), $R^{27}$:

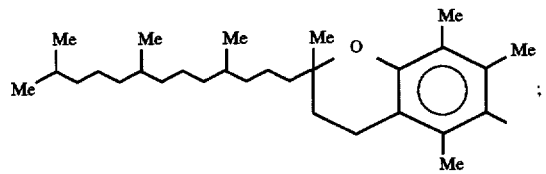

$R^{28}, R^{29}, R^{30}, R^{31}, R^{32}$: H]

A 500-ml flask equipped with a reflux condenser, dropping funnel and stirrer was charged with 61.1 g (1 mol) of ethanolamine and 100 g of ethanol. While heating and stirring the mixture at 80° C. in a nitrogen atmosphere, a solution of 24.3 g (0.05 mol) of tocopheryl glycidyl ether in 25 ml of ethanol was added dropwise over 2 hours. After the contents were heated and stirred further for 18 hours, excess ethanol was distilled off under reduced pressure, and the resultant residue was purified by column chromatography on silica gel, thereby obtaining 23.8 g (yield: 86.9%) of the title compound (Ib-1).

Pale yellow oil.

IR (NaCl, cm$^{-1}$): 3312, 2936, 1456, 1414, 1378, 1252, 1088, 1062, 916, 746.

$^1$H-NMR (CDCl$_3$, δ): 0.79–0.90(m,12H), 0.94–1.62(m, 24H), 1.68–1.87(m,2H), 2.07(s,3H), 2.13(s,3H), 2.17(s,3H), 2.56(br,5H), 2.80–2.89(m,4H), 3.63–3.75(m,4H), 4.07–4.21 (m,1H).

Preparation Example 2:

Preparation of 1-(2-hydroxyethylamino)-3-[9,10-(isopropylidenedioxy)octadecyloxy]-2-Propanol (Ib-2):

[In the general formula (Ib), $R^{27}$:

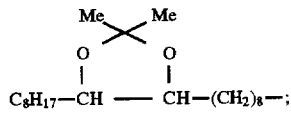

$R^{28}, R^{29}, R^{30}, R^{31}, R^{32}$: H]

A 200-ml flask equipped with a stirrer was charged with 33.05 g (100 mmol) of methyl 9,10-dihydroxyoctadecanate, 52 g (500 mmol) of 2,2-dimethoxypropane and 0.86 g (5 mmol) of p-toluenesulfonic acid. The contents were stirred at room temperature for 18 hours and neutralized with NaHCO$_3$. Thereafter, the solvent was distilled off under reduced pressure.

A 500-ml flask equipped with a stirrer and a dropping funnel was then charged with 3.8 g (100 mmol) of LiAlH$_4$ and 200 ml of tetrahydrofuran. While stirring the mixture at room temperature, an intermediate obtained in the above reaction was added to the mixture over 20 minutes. The resultant mixture was stirred further for 1 hour at room temperature. After 12 g of 5% aqueous KOH were added dropwise to decompose excess LiAlH$_4$, a salt deposited was separated by filtration, and the solvent was distilled off under reduced pressure.

The resultant residue was then transferred to a 300-ml flask equipped with a stirrer and reflux condenser, which was charged with 27.8 g (300 mmol) of epichlorohydrin and 1.61 g (5 mmol) of tetrabutylammonium chloride. While stirring the mixture at 40° C., 33.3 g (400 mmol) of 48% aqueous NaOH were added dropwise over 3 hours. After the resultant mixture was stirred further for 2 hours at 40° C., it was washed with water and concentrated under reduced pressure, and the resultant residue was purified by column chromatography on silica gel, thereby obtaining 23.9 g (yield: 60.0%) of 9,10-(isopropylideneoxy)octadecyl glycidyl ether as an intermediate.

A 200-ml flask equipped with a stirrer, reflux condenser and a dropping funnel was then charged with 30.9 g (506 mmol) of ethanolamine and 6.5 g of ethanol. While stirring the mixture at 80° C., 13.1 g (32.9 mmol) of 9,10-(isopropylideneoxy)octadecyl glycidyl were added dropwise over 2 hours. After the contents were stirred further for 1 hour, the reaction mixture was concentrated under reduced pressure, and the resultant residue was purified by column chromatography on silica gel, thereby obtaining 12.9 g (yield: 85%) of the title compound (Ib-2).

Pale yellow oil.

IR (NaCl, cm$^{-1}$): 3316, 2924, 2856, 1464, 1370, 1240, 1216 1118, 864, 748.

$^1$H-NMR (CDCl$_3$, δ): 0.88(t,J=6.25 Hz,3H), 1.10–1.70 (m,34H), 2.50–2.88(m,4H), 3.00–3.52(m,7H), 3.58–3.78(m, 2H), 3.82–4.10(m,3H).

Example 29

Effect of the amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (Ib-1) and (Ib-2) in a concentration of 0.025% were applied 5 times a week to their corresponding groups of mice for 6 weeks in a dose of 80 µl. As a control, ethanol alone was applied in a dose of 80 µl like the samples.

After completion of the application, the degree of wrinkles was visually observed to rank the samples in accordance with the following standard (wrinkle index). The results are shown in Table 4.

(Wrinkle index; evaluation standard)

1: Wrinkles were completely removed;

2: Wrinkles were scarcely observed;
3: Wrinkles were somewhat observed;
4: Wrinkles were observed to a great extent.

TABLE 4

| Group | Wrinkle index |
|---|---|
| Control | 3.75 ± 0.09 |
| Amine derivative (Ib-1) | 3.00 ± 0.15 |
| Amine derivative (Ib-2) | 3.60 ± 0.18 |

As apparent from the result shown in Table 4, the wrinkles formed on the backs of the hairless mice can be removed by applying the amine derivatives (Ib-1), (Ib-2) thereto.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 5.

TABLE 5

| Group | Area percent by image analysis (%) |
|---|---|
| Control | 6.42 ± 0.63 |
| Amine derivative (Ib-1) | 3.26 ± 0.30 |
| Amine derivative (Ib-2) | 5.14 ± 0.49 |

As apparent from the result shown in Table 5, the wrinkles formed on the backs of the hairless mice can be removed by applying the amine derivatives (Ib-1), (Ib-2) thereto.

Example 30

Inhibitory effect of the amine derivatives on DNA synthesis of epidermic keratinocyte:
(1) Method:
a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.
b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (Ib-1), (Ib-2) obtained in the above synthesis examples was added thereto. Further, 0.2 μCi/ml of [$^3$H] thymidine was subsequently added to incubate the culture for 4 hours. After the supernatant was then removed by suction, and the well was washed 3 times with PBS(-), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

TABLE 6

| Amine derivative | Relative amount of [$^3$H] thyimidine incorporated (%)* | |
|---|---|---|
| | 10 μM | 100 μM |
| (Ib-1) | 21.8 | 8.2 |
| (Ib-2) | 17.3 | 4.4 |

*: Indicating the relative value where a control is assumed to be 100%.

It was apparent from Table 6 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells turn insoluble membrane (cornified envelope), i.e., become keratinized. It is understood from this fact that the amine derivatives according to the present invention are active in facilitating the keratinization of epidermis.

Example 31

A W/O type cream having the following composition was obtained in accordance with the below-described preparation process.

| (Composition) | (wt. %) |
|---|---|
| (1) Amine derivative (Ib-1) | 0.1 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)-(7) were heated to 80° C. to melt them, and the components (8)-(11) were added to the melt. The resultant mixture was intimately mixed to prepare a W/O type cream.

Example 32

An O/W type cream having the following composition was obtained in accordance with the below-described preparation process.

| (Composition) | (wt. %) |
|---|---|
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (Ib-1) | 0.001 |
| (7) Cholesterol | 1.5 |
| (8) Cholesteryl isostearate | 1.0 |

| (Composition) | (wt. %) |
|---|---|
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 33

A sunscreen cream having the following composition was obtained in accordance with the below-described preparation process.

| (Composition) | (wt. %) |
|---|---|
| (1) Amine derivative (Ib-2) | 0.05 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 34

A pack having the following composition was obtained in accordance with the below-described preparation process.

| (Composition) | (wt. %) |
|---|---|
| (1) Amine derivative (Ib-1) hydrochloride | 0.05 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 35

An ointment having the following composition was obtained in accordance with the below-described preparation process.

| (Composition) | (wt. %) |
|---|---|
| (1) Amine derivative (Ib-2) | 0.2 |
| (2) White petrolatum | Balance |

| (Composition) | (wt. %) |
|---|---|
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations, which were prepared in Examples 31–35 and comprised the amine derivative (Ib-1) or (Ib-2) according to the present invention as an effective ingredient, had excellent effects of preventing the occurrence of wrinkles and smoothing or removing wrinkles and moreover inhibited parakeratosis of the skin, epidermic hypertrophy and metabolic aberration of lipid and were excellent in recovery of normal functions and maintenance of homeostasis.

Preparation Example 3:

Preparation of 1-(2-hydroxyethylamino)-3-methoxy-2-propanol (Ic-1) [In the general formula (Ic), $R^{33}=CH_3$; $R^{34}=R^{35}=R^{36}=R^{37}=R^{38}=H$]:

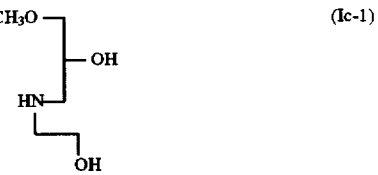

(Ic-1)

A 1000-ml two-necked flask equipped with a reflux condenser and 100-ml dropping funnel was charged with 517 g (8.46 mol) of ethanolamine and 103 g of ethanol. While heating and stirring the mixture at 80° C. in a nitrogen atmosphere, 50.0 g (0.57 mol) of methyl glycidyl ether were added dropwise over 2 hours. After the contents were heated and stirred further for 2 hours, the reaction mixture was subjected to distillation, thereby obtaining 73.0 g (yield: 80%) of the title compound (Ic-1).

Colorless solid.

Melting point: 41.5°–42.5° C.

IR (NaCl, cm$^{-1}$): 3400, 2932, 2850, 1452, 1414, 1102, 1106, 958.

$^1$H-NMR (CDCl$_3$, δ): 2.52–2.82(m,4H), 3.25–3.42(m, 5H) , 3.50–4.15(m,6H).

Preparation Example 4:

The amine derivative (Ic-1) was reacted with hydrochloric acid, glycolic acid or lactic acid in ethanol, and the solvent was distilled off under reduced pressure, thereby preparing the hydrochloride, glycolate or lactate of the amine derivative (Ic-1). Hydrochloride of (Ic-1):

Pale yellow oil.

IR (NaCl, cm$^{-1}$): 3344, 2928, 1664, 1584, 1446, 1190, 1078.

$^1$H-NMR (D$_2$O, δ): 3.07–3.31(m,4H), 3.41(s,3H), 3.55(d, 2H,J=4.3 Hz), 3.85–3.90(m,2H), 4.10–4.21(m,1H).

Lactate of (Ic-1):

Colorless oil.

IR (NaCl, cm$^{-1}$): 3340, 2944, 1588, 1456, 1418, 1198, 1124, 1038, 966, 852, 772.

$^1$H-NMR (CDCl$_3$δ): 1.29–1.39(m,3H), 2.80–4.35(m, 18H).

Glycolate of (Ic-1):

Colorless oil.

IR (NaCl, cm$^{-1}$): 3320, 2904, 1600, 1446, 1322, 1198, 1076, 968, 918, 748, 690.

$^1$H-NMR (CDCl$_3$, δ): 2.92–3.09(m,4H), 3.38(s,3H), 3.43–3.49(m,2H), 3.82–4.18(m,10H).

Preparation Example 5:

A reaction was conducted in the same manner as in Preparation Example 3 except that allyl glycidyl ether was used in place of methyl glycidyl ether in Preparation Example 3, thereby synthesizing the following amine derivative (Ic-2).

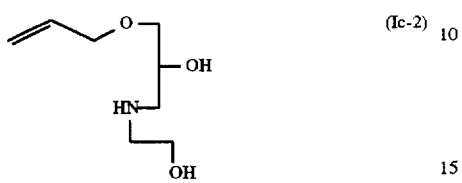

Colorless oil.

IR (NaCl cm$^{-1}$): 3320, 2920, 2860, 1648, 1460, 1428, 1356, 1106, 1056, 1000, 932, 868.

$^1$H-NMR (CDCl$_3$, δ): 2.57–2.77(m,4H), 3.40–4.02(m, 2H), 5.16–5.31(m,2H), 5.80–6.00(m,1H).

Preparation Example 6:

Preparation of 1-((1,1-bis(hydroxymethyl)ethyl)amino)-3-methoxy-2-propanol (Ic-3) [In the general formula (Ic), $R^{33}=R^{35}=CH_3$; $R^{36}=CH_2OH$; $R^{34}=R^{37}=R^{38}=H$]:

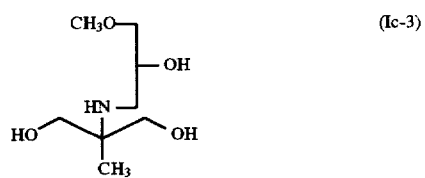

A 300-ml two-necked flask equipped with a reflux condenser and 10-ml dropping funnel was charged with 78.9 g (0.75 mol) of 2-amino-2-methyl-1,3-propanediol and 15.8 g of ethanol. While heating and stirring the mixture at 80° C. in a nitrogen atmosphere, 4.4 g (0.05 mol) of methyl glycidyl ether were added dropwise over 3 hours. After completion of the reaction, ethanol was distilled off under reduced pressure, and excess 2-amino-2-methyl-1,3-propanediol was removed by crystallization. The resultant residue was then purified by flash column chromatography on silica gel, thereby obtaining 9.1 g (yield: 94%) of the title compound (Ic-3).

Pale yellow oil.

IR (NaCl, cm$^{-1}$): 3380, 2936, 2888, 1456, 1384, 1326, 1196, 1128, 1044, 962, 864, 750.

$^1$H-NMR (CDCl$_3$, δ): 0.94(s,3H), 2.55(dd, 1H,J=8.3,11.7 Hz), 2.66(dd, 1H,J=3.5,11.7 Hz), 3.28–3.94(m,14H).

Preparation Example 7:

A reaction was conducted in the same manner as in Preparation Example 6 except that tris(hydroxymethyl)aminomethane and water were used in place of 2-amino-2-methyl-1,3-propanediol and ethanol, respectively, in Preparation Example 6, thereby synthesizing the following amine derivative (Ic-4).

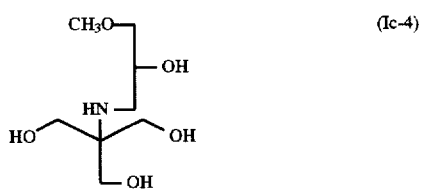

Pale yellow oil.

IR (NaCl, cm$^{-1}$): 3368, 2892, 1462, 1196, 1032, 964, 870, 751.

$^1$H-NMR (CDCl$_3$, δ): 2.63(dd,1H,J=7.7,12.1 Hz), 2.75 (dd,1H,J=3.6,12.1 Hz), 3.21–3.94(m,17H).

Preparation Example 8:

Preparation of 1-(N-(2-hydroxyethyl)-N-methylamino)-3-methoxy-2-propanol (Ic-5) [In the general formula (Ic), $R^{33}=R^{34}=CH_3$; $R^{35}=R^{36}=R^{37}=R^{38}=H$]:

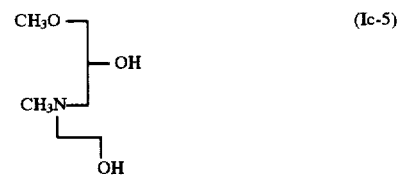

A 100-ml two-necked flask equipped with a reflux condenser was charged with 8.8 g (0.1 tool) of methyl glycidyl ether, 9.0 g (0.12 mol) of 2-(methylamino)ethanol and 1.8 g of ethanol. The contents were heated and stirred at 80° C. for 3 hours in a nitrogen atmosphere. After completion of the reaction, the reaction mixture was subjected to distillation, thereby obtaining 14.5 g (yield: 89%) of the title compound (Ic-5).

Colorless oil.

IR (NaCl, cm$^{-1}$): 3396, 2892, 1448, 1324, 1192, 1030, 874.

$^1$H-NMR (CDCl$_3$, δ): 2.33(s,3H) , 2.37–2.72(m,4H), 3.32–3.96(m,10H) .

Preparation Example 9:

Reactions were conducted in the same manner as in Preparation Example 8 except that diethanolamine and allyl glycidyl ether were used respectively in place of 2-(methylamino)ethanol in Preparation Example 8, thereby synthesizing the following amine derivatives (Ic-6) and (1c-7).

Further, the amine derivative (Ic-7) was hydrogenated by means of a Pd/C catalyst, thereby synthesizing the following amine derivative (Ic-8).

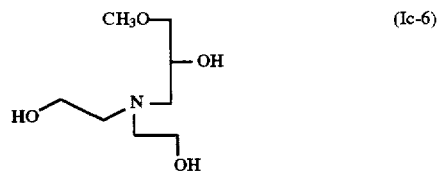

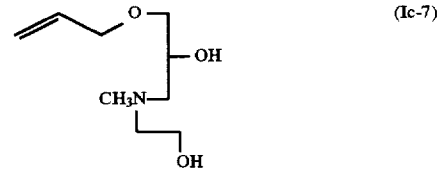

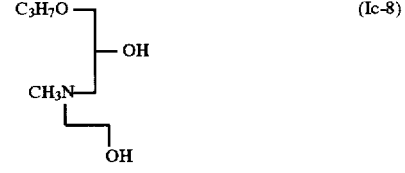

(Ic-6):
Colorless oil.

IR (NaCl, cm$^{-1}$): 3340, 2884, 1442, 1362, 1248, 1030.

$^1$H-NMR (CDCl$_3$, δ): 2.37–2.83(m,6H), 3.37–3.96(m, 10H), 4.74(bs,3H).

(Ic-7):
Colorless oil.

IR (NaCl, cm$^{-1}$): 3420, 3088, 2948, 2856, 1650, 1462, 1424, 1328, 1264, 1198, 1082, 1034, 926, 874, 800.

¹H-NMR (CDCl₃, δ): 2.32(s,3H), 2.38–2.71(m,4H), 3.37–3.66(m,6H), 3.86–4.05(m,3H), 5.16–5.33(m,2H).
(Ic-8):
Colorless oil.
IR (NaCl, cm⁻¹): 3432, 2948, 2872, 1466, 1118, 1084, 1036, 956, 872.
¹H-NMR (CDCl₃, δ): 0.92(t,3HJ=7.4 Hz), 1.60(tq,2H,J= 7.4,7.4 Hz), 2.33(s,3H), 2.39–2.72(m,4H), 3.35–3.49(m, 6H), 3.64(t,2H,J=5.3 Hz), 3.86–3.97(m,1H).

Preparation Example 10:

Preparation of 1-(N-benzyl-N-(2-hydroxyethyl)amino)-3-(2,3-dihydroxypropyloxy)-2-propanol (Ic-9)[In the general formula (Ic), $R^{33}$=HOCH₂CH(OH)CH₂; $R^{34}$=C₆H₅CH₂; $R^{35}$=$R^{36}$=$R^{37}$=$R^{38}$=H]:

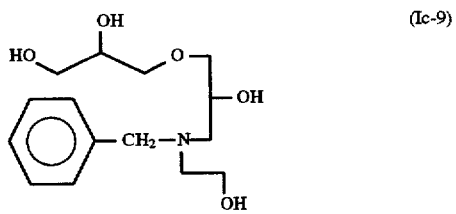

(Ic-9)

A 100-ml two-necked flask equipped with a reflux condenser was charged with 3.7 g (0.025 mol) of 2,3-dihydroxypropyl glycidyl ether, 3.8 g (0.025 mol) of 2-benzylaminoethanol and 0.8 g of ethanol. The contents were heated and stirred at 80° C. for 3 hours in a nitrogen atmosphere. After completion of the reaction, ethanol was distilled off under reduced pressure, and the resultant residue was purified by flash column chromatography on silica gel, thereby obtaining 5.3 g (yield: 71%) of the title compound (Ic-9).

Yellow oil.
IR (NaCl, cm⁻¹): 3400, 3032, 2880, 1652, 1604, 1498, 1456, 1372, 1330, 1258, 1126, 1048, 870, 794, 740, 698.
¹H-NMR (CDCl₃, δ): 2.48–2.80(m,4H), 3.33–4.03(m, 16H), 7.21–7.36(m,5H)

Preparation Example 11:

A reaction was conducted in the same manner as in Preparation Example 10 except that methyl glycidyl ether and N-methylglucamine were used in place of 3,3-dihydroxypropyl glycidyl ether and 2-benzylaminoethanol, respectively, in Preparation Example 10, thereby synthesizing the following amine derivative (Ic-10).

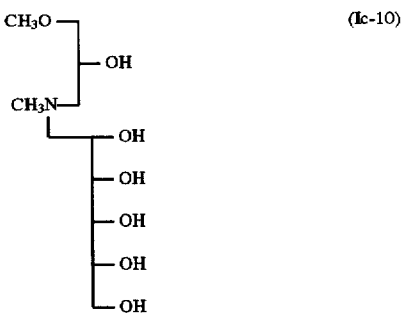

(Ic-10)

Pale yellow oil.
IR (NaCl, cm⁻¹): 3344, 2920, 1630, 1434, 1078, 870.
¹H-NMR (CDCl₃, δ): 2.33, 2.34(s, total 3H), 2.49–2.64 (m,4H), 3.30–4.07(m,12H).

Example 36

Effect of the amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm². The exposure was effected for 20 weeks. After confirming the fact that the mice had got wrinkles at their backs, they were divided into groups each consisting of 8 mice. Ethanol solutions separately containing the amine derivatives (Ic-1) to (Ic-10) in a concentration of 0.025% were applied 5 times a week to their corresponding groups of mice for 6 weeks in a dose of 80 µl. As a control, ethanol alone was applied in a dose of 80 µl like the samples.

After completion of the application, the degree of wrinkles was visually observed to rank the samples in accordance with the following standard (wrinkle index). The results are shown in Table 7.

(Wrinkle index; evaluation standard)

1: Wrinkles were completely removed;
2: Wrinkles were scarcely observed;
3: Wrinkles were somewhat observed;
4: Wrinkles were observed to a great extent.

TABLE 7

| Group | Wrinkle index |
| --- | --- |
| Control | 3.75 ± 0.09 |
| Amine derivative (Ic-1) | 2.00 ± 0.42 |
| Amine derivative (Ic-2) | 2.25 ± 0.35 |
| Amine derivative (Ic-3) | 2.50 ± 0.25 |
| Amine derivative (Ic-4) | 2.63 ± 0.25 |
| Amine derivative (Ic-5) | 2.58 ± 0.42 |
| Amine derivative (Ic-6) | 3.12 ± 0.25 |
| Amine derivative (Ic-7) | 2.50 ± 0.25 |
| Amine derivative (Ic-8) | 2.25 ± 0.25 |
| Amine derivative (Ic-9) | 2.25 ± 0.18 |
| Amine derivative (Ic-10) | 3.00 ± 0.35 |

As apparent from the result shown in Table 7, the wrinkles formed on the backs of the hairless mice were able to be removed by applying the amine derivatives (Ic-1) to (IC-10) thereto.

In order to further analyze the particulars of wrinkles, skin replicas of the size of 1 cm² in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown in Table 8.

TABLE 8

| Group | Area percent by image analysis (%) |
| --- | --- |
| Control | 6.42 ± 0.63 |
| Amine derivative (Ic-1) | 1.91 ± 0.50 |
| Amine derivative (Ic-2) | 3.25 ± 0.74 |
| Amine derivative (Ic-3) | 2.84 ± 0.64 |
| Amine derivative (Ic-4) | 3.76 ± 0.75 |
| Amine derivative (Ic-5) | 2.52 ± 0.54 |
| Amine derivative (Ic-6) | 4.03 ± 0.58 |
| Amine derivative (Ic-7) | 3.16 ± 0.72 |
| Amine derivative (Ic-8) | 3.33 ± 0.56 |

TABLE 8-continued

| Group | Area percent by image analysis (%) |
| --- | --- |
| Amine derivative (Ic-9) | 3.25 ± 0.47 |
| Amine derivative (Ic-10) | 3.93 ± 0.56 |

As apparent from the result shown in Table 8, the wrinkles formed on the backs of the hairless mice can be removed by applying the amine derivatives (Ic-1) to (Ic-10) thereto.

Example 37

Inhibitory effect of the amine derivatives on DNA synthesis of epidermic keratinocyte:
(1) Method:
a) Culture of human epidermic keratinocyte:
Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.
b) Determination of DNA synthesis (thymidine incorporation):
Keratinocytes cultured in a vegetative state in a 24-well plate were used. A medium in each well was first removed by suction to add 450 µl of K-GM, to which no pituitary gland extract was added, to the well, thereby making a medium exchange. Thereafter, each of the amine derivatives (Ic-1) to (Ic-10) obtained in the above synthesis examples was added thereto. Further, 0.2 µCi/ml of [$^3$H] thymidine was subsequently added to incubate the culture for 4 hours. After the supernatant was then removed by suction, and the well was washed 3 times with PBS(−), 500 µl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.
Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

TABLE 9

| Amine derivative | Relative amount of [$^1$H] thyimidine incorporated (%)* | |
| --- | --- | --- |
| | 10 µM | 100 µM |
| Amine derivative (Ic-1) | 76.2 ± 5.5 | 42.0 ± 1.5 |
| Amine derivative (Ic-2) | 67.6 ± 5.5 | 33.1 ± 1.2 |
| Amine derivative (Ic-3) | 81.7 ± 4.9 | 38.9 ± 2.7 |
| Amine derivative (Ic-4) | 87.3 ± 5.2 | 46.7 ± 2.8 |
| Amine derivative (Ic-5) | 65.7 ± 4.3 | 39.1 ± 1.5 |
| Amine derivative (Ic-6) | 78.3 ± 4.8 | 42.7 ± 1.5 |
| Amine derivative (Ic-7) | 63.9 ± 4.2 | 31.2 ± 1.2 |
| Amine derivative (Ic-8) | 75.0 ± 4.6 | 40.7 ± 1.3 |
| Amine derivative (Ic-9) | 57.5 ± 4.1 | 35.9 ± 1.2 |
| Amine derivative (Ic-10) | 81.9 ± 5.1 | 45.9 ± 1.7 |

*: Indicating the relative value where a control is assumed to be 100%.

It was apparent from Table 9 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells turn insoluble membrane (cornified envelope), i.e., become keratinized. It is understood from this fact that the amine derivatives according to the present invention are active in facilitating the keratinization of epidermis.

Example 38

A W/O type cream having the following composition was obtained in accordance with the below-described preparation process.

| (Composition) | (wt. %) |
| --- | --- |
| (1) One of amine derivatives (Ic-1)–(Ic-10) | 0.08 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 39

An O/W type cream having the following composition was obtained in accordance with the below-described preparation process.

| (Composition) | | (wt. %) |
| --- | --- | --- |
| (1) | Polyoxyethylene (10) hardened castor oil | 1.0 |
| (2) | Sorbitan monostearate | 0.5 |
| (3) | Sodium stearoylmethyltaurine | 0.5 |
| (4) | Cetostearyl alcohol | 2.0 |
| (5) | Stearic acid | 1.8 |
| (6) | One of amine derivatives (Ic-1)–(Ic-10) | 0.001 |
| (7) | Cholesterol | 1.5 |
| (8) | Cholesteryl isostearate | 1.0 |
| (9) | Neopentyl glycol dicaprate | 8.0 |
| (10) | Methylpolysiloxane | 5.0 |
| (11) | Glycerol | 5.0 |
| (12) | Purified water | Balance |

(Preparation process)

Components (1)–(10) were heated to 80° C. to melt them, and the components (11)–(12) were added to the melt. The resultant mixture was intimately mixed to prepare an O/W type cream.

Example 40

A sunscreen cream having the following composition was obtained in accordance with the below-described preparation process.

| (Composition) | | (wt. %) |
|---|---|---|
| (1) | One of amine derivatives (Ic-1)–(Ic-10) | 0.0005 |
| (2) | Silicon-coated zinc oxide | 7.0 |
| (3) | 2-Ethylhexyl p-methoxycinnamate | 3.0 |
| (4) | Cholesteryl isostearate | 1.0 |
| (5) | Polyether-modified silicone | 2.0 |
| (6) | Methylpolysiloxane | 5.0 |
| (7) | Cyclic silicone | 15.0 |
| (8) | Magnesium sulfate | 1.0 |
| (9) | Glycerol | 5.0 |
| (10) | Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 41

A pack having the following composition was obtained in accordance with the below-described preparation process.

| (Composition) | | (wt. %) |
|---|---|---|
| (1) | Hydrochloride of one of amine derivatives (Ic-1)–(Ic-10) | 0.05 |
| (2) | Polyvinyl alcohol | 15.0 |
| (3) | Sodium carboxymethylcellulose | 5.0 |
| (4) | Propylene glycol | 3.0 |
| (5) | Ethanol | 8.0 |
| (6) | Purified water | Balance |
| (7) | Perfume base | 0.5 |
| (8) | Antiseptic, oxidizing agent | q.s. |

(Preparation process)

Components (1)–(8) were heated to 70° C. to melt them, and then cooled, thereby preparing a pack.

Example 42

An ointment having the following composition was obtained in accordance with the below-described preparation process.

| (Composition) | | (wt. %) |
|---|---|---|
| (1) | One of amine derivatives (Ic-1)–(Ic-10) | 0.075 |
| (2) | White petrolatum | Balance |
| (3) | Cholesteryl isostearate | 3.0 |
| (4) | Liquid paraffin | 10.0 |
| (5) | Glyceryl ether | 1.0 |
| (6) | Glycerol | 10.0 |

(Preparation process)

Components (1)–(6) were heated to 80° C. to melt them, and then cooled, thereby preparing an ointment.

The dermatologic preparations according to the present invention, which were prepared in Examples 38–42, had excellent effects of preventing the occurrence of wrinkles and smoothing or removing wrinkles and moreover inhibited parakeratosis, epidermic hypertrophy and metabolic aberration of lipid and were excellent in recovery of normal functions and maintenance of homeostasis.

Preparation Example 12:

Preparation of 1-(2-hydroxyethylamino)-2-methyl-3-tetradecyloxy-2-propanol (IIa-1):

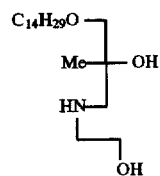

A 200-ml flask equipped with a stirrer was charged with 10 g (46.6 mmol) of tetradecanol, 50 ml of dimethylformamide, 2.86 g (71.5 mmol) of 60% NaH and 5.96 g (65.8 mmol) of methallyl chloride. The contents were stirred at 60° C. for 15 hours. After completion of the reaction, the reaction mixture was added with water and subjected to extraction with hexane, and the solvent was distilled off under reduced pressure. The resultant residue was charged into a 300-ml flask equipped with a stirrer, and 12.24 g (70.9 mmol) of m-chloroperbenzoic acid and 200 ml of dichloromethane were added thereto. The resultant mixture was stirred at room temperature for 19 hours. Solids formed were separated by filtration, and the resultant solution was concentrated under reduced pressure and then purified by column chromatography on silica gel, thereby obtaining 10.54 g (yield: 79.4%) of 1,2-epoxy-2-methyl-3-tetradecyloxypropane as an intermediate.

A 100-ml flask equipped with a stirrer and dropping funnel was then charged with 16.8 g (280 mmol) of ethanolamine and 15 g of ethanol. While stirring the mixture at 80° C., an ethanol solution of 5.00 g (17.6 mmol) of 1,2-epoxy-2-methyl-3-tetradecyloxypropane was added dropwise over 3 hours. The contents were stirred further for 2 hours. The resultant reaction mixture was concentrated under reduced pressure, and the resultant residue was purified by column chromatography on silica gel, thereby obtaining 4.13 g (yield: 68%) of the title compound.

Pale yellow solid.

Melting point: 49.1°–50.2° C.

IR (KBr, cm$^{-1}$): 3324, 2924, 2856, 1462, 1378, 1110, 1058.

$^1$H-NMR (CDCl$_3$, δ): 0.88(t,J=6.4 Hz,3H), 1.08–1.68(m, 27H), 3.34(s,2H), 3.43 (t,J=6.6 Hz,2H), 3.70(td,J=5.1 Hz,1,2 Hz,2H), 3.99(brs,3H).

Preparation Example 13:

Reactions were conducted in the same manner as in Preparation Example 12 except that crotyl chloride, prenyl chloride and 3-methyl-3-butenyl p-toluenesulfonate were respectively used in place of methallyl chloride in Preparation Example 12, thereby preparing the following amine derivatives (IIa-2)–(IIa-4).

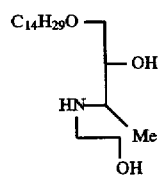

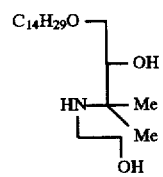

-continued

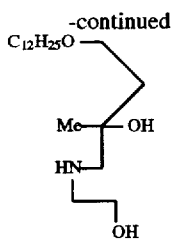
(IIa-4)

(IIa-2):
  Pale yellow solid.
  Melting point: 37.5°–38.8° C.
  IR (KBr, cm$^{-1}$): 3464, 2920, 2852, 1466, 1376, 1102, 1054.
  $^1$H-NMR (CDCl$_3$, δ): 0.88(t,J=6.4 Hz,3H), 1.07(d,J=6.5 Hz,3H), 1.22–1.82(m,24H), 2.60–3.15(m,6H), 3.32–3.39 (m,7H).

(IIa-3):
  Pale yellow oil.
  IR (NaCl, cm$^{-1}$): 3320, 2924, 2852, 1462, 1382, 1108.
  $^1$H-NMR (CDCl$_3$, δ): 0.88(t,J=6.4 Hz,3H), 1.10(s,3H), 1.16(s,3H), 1.18–1.70(m,24H), 2.72=2.86(m,2H), 2.92–3.35(m,3H), 3.36–3.76(m,7H).

(IIa-4):
  Pale yellow oil.
  IR (NaCl, cm$^{-1}$): 3380, 2928, 2856, 1462, 1372, 1112, 1060.
  $^1$H-NMR (CDCl$_3$, δ): 0.82–0.95(m,3H), 1.11–1.42(m, 21H), 1.48–1.74(m,3H), 1.87–2.03(m,1H), 2.56(d,J=11.7 Hz,1H), 2.58(br,3H), 2.62(d,J=11.7 Hz,1H), 2.77–2.85(m, 2H), 3.41(d,J=6.5 Hz,2H), 3.54–3.75(m,4H).

Preparation Example 14:
  Preparation of 1-(3-hydroxypropylamino)-3-tetradecyloxy-2-propanol (II-5):

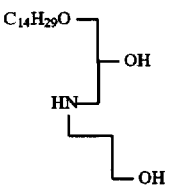
(IIa-5)

A 300-ml two-necked flask equipped with a stirrer and a dropping funnel was charged with 25.1 g (0.33 mol) of 3-amino-1-propanol and 6.00 g of ethanol, and the contents were heated and stirred at 80° C. in a nitrogen atmosphere. After 9.00 g (33 mmol) of tetradecyl glycidyl ether were added dropwise over 2 hours, the resultant mixture was stirred further for 1 hour. The reaction mixture was poured into 400 ml of ice water and stirred for 1 hour. Crystals formed were then collected by filtration and recrystallized from methanol, thereby obtaining 15.4 g (yield: 92%) of the title compound (IIa-5).
  Colorless solid.
  Melting point: 63.9°–65.2° C.
  IR (KBr, cm$^{-1}$): 3320, 2920, 2852, 1462, 1306, 1116, 1052.
  $^1$H-NMR (CDCl$_3$, δ): 0.88(t,J=6.29 Hz,3H), 1.16–1.80 (m,26H), 2.46–3.50(m,11H), 3.66–3.96(m,3H).

Preparation Example 15:
  Reactions were conducted in the same manner as in Preparation Example 14 except that 5-amino-1-propanol, 2-(2-aminoethoxy)ethanol, 3-(3-amino-2-hydroxypropyl)-1,2-propanediol and 3-amino-1-glucopyranosyloxy-2-propanol were respectively used in place of 3-amino-1-propanol in Preparation Example 14, thereby preparing the following amine derivatives (IIa-6)–(IIa-9).

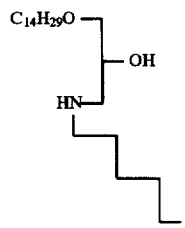
(IIa-6)

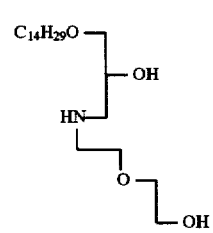
(IIa-7)

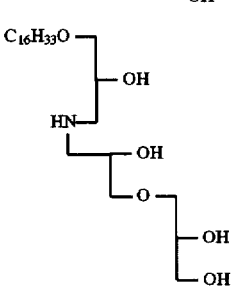
(IIa-8)

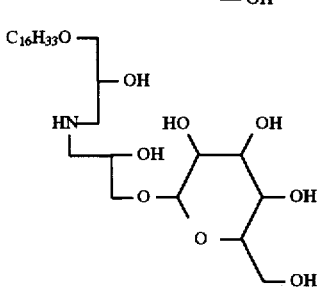
(IIa-9)

(IIa-6):
  Colorless solid.
  Melting point: 69.4°–70.5° C.
  IR (KBr, cm$^{-1}$): 3296, 2920, 2852, 1462, 1378, 1116, 1056.
  $^1$H-NMR (CDCl$_3$, δ): 0.88(t,J=5.66 Hz,3H), 1.10–1.68 (m,30H), 2.50–2.76(m,4H), 3.28–3.50(m,7H), 3.56–3.68(m, 2H), 3.77–3.92(m,1H).

(IIa-7):
  Colorless solid.
  Melting point: 56.5°–57.6° C.
  IR (KBr, cm$^{-1}$): 3376, 2920, 2852, 1466, 1378, 1126, 1070.
  $^1$H-NMR (CDCl$_3$, δ): 0.88(t,J=6.29 Hz,3H), 1.10–1.68 (m,24H), 2.50–2.88(m,4H), 2.86–3.76(m,13H), 3.80–3.98 (m,1H).

(IIa-8):
  Colorless solid.
  Melting point: 111.8°–113.0° C.
  IR (KBr, cm$^{-1}$): 3440, 2924, 2856, 1470, 1124.
  $^1$H-NMR (CDCl$_3$, δ): 0.86(t,J=6.40 Hz,3H), 1.20–1.41 (m,28H), 2.48–2.57(m,4H), 3.23–3.60(m,15H), 3.67–3.90 (m,1H).

(IIa-9):
  Colorless solid.
  IR (KBr, cm$^{-1}$): 3368, 2920, 2852, 1470, 1120, 1070, 1032.

$^1$H-NMR (CDCl$_3$, δ): 0.85–1.70(m,31H), 2.40–5.00(m, 26H).

Preparation Example 16:

Preparation of 4-(2-hydroxyethylamino)-1-dodecyloxy-2-methyl-2-butanol (IIa-10):

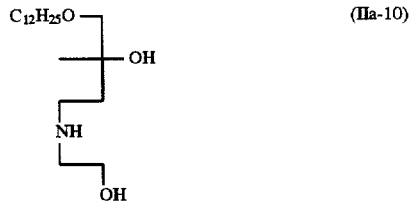

(IIa-10)

A 100-ml flask equipped with a stirrer was charged with 11.18 g (60 mmol) of 1-dodecanol, 0.20 g (5 mmol) of 60% NaH and 3.73 g (20 mmol) of 1,2-epoxy-2-methyl-4-(2-tetrahydropyranyloxy)butane. The contents were stirred at 20° C. for 16 hours, and excess 1-dodecanol was distilled off under reduced pressure. The resultant reaction mixture was then added with water and subjected to extraction with isopropyl ether, and the solvent was distilled off under reduced pressure. The resultant residue was added with 100 ml of methanol and 1.01 g (4 mmol) of pyridinium p-toluenesulfonate, and the mixture was stirred at 40° C. for 24 hours and neutralized with an aqueous solution of NaHCO$_3$, followed by extraction with isopropyl ether. The resultant extract was concentrated under reduced pressure.

A 200-ml flask equipped with a stirrer was then charged with the resultant residue and 70 ml of pyridine, and 3.82 g (20 mmol) of p-toluenesulfonyl chloride were added at 5° C. The mixture was stirred for 6 hours. The reaction mixture was then added with water and subjected to extraction with isopropyl ether, followed by concentration under reduced pressure. The resultant residue was charged into a 200-ml flask equipped with a stirrer, and 24.4 g (0.4 mol) of ethanolamine and 50 ml of ethanol were added thereto, followed by stirring at 80° C. for 18 hours. After completion of the reaction, the reaction mixture was added with aqueous KOH and subjected to extraction with chloroform, followed by concentration under reduced pressure. The resultant residue was purified by column chromatography on silica gel, thereby obtaining 2.00 g (yield: 30.2%) of the title compound (IIa-10).

Pale yellow paste.

IR (NaCl, cm$^{-1}$): 3380, 2920, 2852, 1462, 1378, 1110.

$^1$H-NMR (CDCl$_3$, δ): 0.82–0.94(m,3H), 1.14–1.41(m, 21H), 1.46–1.97(m,4H), 2.83–2.94(m,2H), 2.99(t,J=6.3 Hz,2H), 3.26(d,J=9.1 Hz,1H), 3.30(d,J=9.1 Hz,1H), 3.43(t, J=6.6 Hz,2H), 3.52–3.81(m,2H), 4.46(br,3H).

Preparation Example 17:

Preparation of (3-tetradecyloxy-2-hydroxypropylamino) acetic acid hydrochloride [(IIa-11) hydrochloride]:

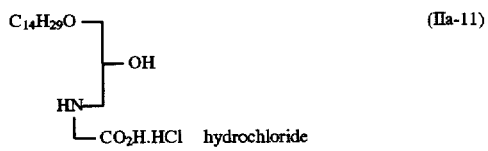

A 300-ml two-necked flask equipped with a stirrer was charged with 7.51 g (0.1 mol) of glycine, 8.3 g (0.1 mol) of 48% NaOH and 200 ml of ethanol. While stirring the mixture at 80° C., an ethanol solution of 2.70 g (10 mmol) of tetradecyl glycidyl ether was added, and the resultant mixture was stirred for 3 hours. After ethanol was distilled off under reduced pressure, methanol and hydrochloric acid was added to the mixture to acidify it. The mixture was subjected to extraction with chloroform. The resultant extract was concentrated under reduced pressure, and the residue was then purified by column chromatography on silica gel, thereby obtaining 1.17 g (yield: 30.7%) of the title compound [(IIa-10) hydrochloride].

Colorless solid.

Melting point: 180° C. (decomposed).

(KBr, cm$^{-1}$): 3340, 3008, 2916, 2852, 1750, 1594, 1468, 1424, 1364, 1274, 1224, 1130.

$^1$H-NMR (CDCl$_3$:CD$_3$OD=2:1, δ): 0.80–0.99(m,3H), 1.09–1.74(m,24H), 3.00–3.33(m,2H), 3.40–3.62(m,4H), 3.71–3.92(m,2H), 3.98–4.20(m,1H).

Preparation Example 18:

A reaction was conducted in the same manner as in Preparation Example 14 except that dimethyl 2-aminobutanedioate was used in place of 3-amino-1-propanol in Preparation Example 14, thereby synthesizing the following amine derivative (IIa-12). This product was further reacted with hydrochloric acid in ethanol, and the solvent was distilled off under reduced pressure, thereby preparing the hydrochloride of the amine derivative (IIa-12).

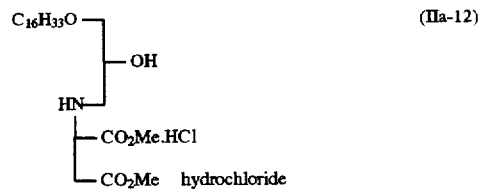

Colorless solid.

IR (KBr, cm$^{-1}$): 3356, 2920, 2852, 1734, 1464, 1254, 1214, 1138, 1116.

$^1$H-NMR (CDCl$_3$; CD$_3$OD, δ): 0.80(t,J=6.6 Hz,3H), 1.08–1.64(m,28H), 2.35–2.75(m,3H), 2.80–3.32(m,2H), 3.34–3.62(m,2H), 3.64–3.90(m,10H), 4.04–4.22(m,1H).

Preparation Example 19:

Preparation of 2-(3-methyl-branched isostearyloxy-2-methoxypropylamino)-1-ethanol (IIa-13):

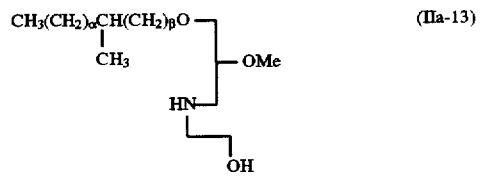

(in the formula, α nd β denote number satisfying the following relationship: α+β=11–17, α=4–10, β=5–11, and having a distribution that the peaks of α and β are 7 and 8, respectively.)

A 100-ml flask equipped with a stirrer was charged with 3.59 g (10 mmol) of 3-methyl-branched isostearyloxy-2-methoxy-1-propanol and 30 ml of pyridine, and 3.82 g (20 mmol) of p-toluenesulfonyl chloride were added at 5° C., followed by stirring for 6 hours. The reaction mixture was added with water and subjected to extraction with isopropyl ether, and the solvent was distilled off under reduced pressure. The resultant residue was charged into a 100-ml flask equipped with a stirrer, to which 12.2 g (0.2 mol) of ethanolamine and 50 ml of ethanol were added, followed by stirring at 80° C. for 18 hours. After completion of the reaction, aqueous KOH was added, extraction with chloroform was conducted, and the solvent was distilled off under reduced pressure. The resultant residue was purified by column chromatography on silica gel, thereby obtaining 2.58 g (yield: 64.2%) of the title compound (IIa-13).

Pale yellow oil.

IR (NaCl, cm$^{-1}$): 3316, 2924, 2856, 1456, 1114.

$^1$H-NMR (CDCl$_3$, δ): 0.75–0.98(m,6H), 1.00–1.76(m, 29H), 2.52(brs,2H), 2.62–2.88 (m,4H), 3.30–3.68 (m,10H).

Preparation Example 20:

Preparation of N-(2-hydroxyethyl)-N,N-dimethyl-N-[3-(methyl-branched isostearyloxy)-2-hydroxypropyl] ammonium iodide (IIb-1):

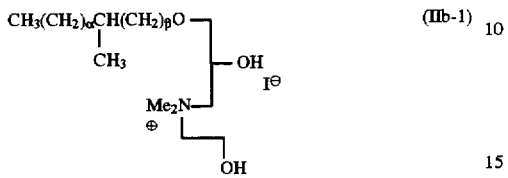

(in the formula, α and β have the same meaning as defined above.)

A 300-ml flask equipped with a stirrer was charged with 5.05 g (12.6 mmol) of 3-(methyl-branched isostearyl-1-[N-methyl-N-2-(hydroxyethyl)amino]-2-propanol prepared from methyl-branched isostearyl glycidyl ether and N-methylethanolamine in the same manner as in Preparation Example 14, and 100 ml of diethyl ether. While stirring the contents at 0° C., 9.13 g (64.3 mmol) of iodomethane were added, and the resultant mixture was stirred further for 14 hours at room temperature. The resultant reaction mixture was concentrated under reduced pressure, and the residue was purified by column chromatography on silica gel, thereby obtaining 3.01 g (yield: 44%) of the title compound (IIb-1).

Yellow oil.

IR (NaCl, cm$^{-1}$): 3360, 2920, 2856, 1464, 1368, 1112, 970.

$^1$H-NMR (CDCl$_3$, δ): 0.72–0.96(m,6H), 0.98–1.80(m, 29H), 3.30–3.75(m,12H), 3.80–4.25 (m,6H), 4.42–4.60(m, 1H).

Preparation Example 21:

Preparation of N-(2-hydroxypropyl)-N,N-dimethyl-N-[3-(methyl-branched isostearyloxy)-2-methoxypropyl] ammonium bromide (IIb-2):

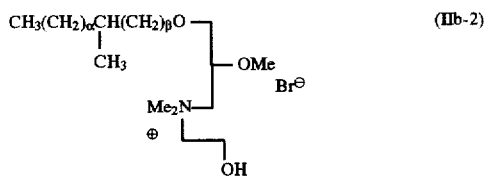

(in the formula, α and β have the same meaning as defined above.)

A 100-ml flask equipped with a stirrer was charged with 1.00 g (2.5 mmol) of the amine derivative (IIa-13) obtained in Preparation Example 19, 2.33 g (25 mmol) of methyl bromide and 300 mol of ethanol, and the contents were stirred at 50° C. for 72 hours. The resultant reaction mixture was concentrated under reduced pressure, and the residue was purified by column chromatography on silica gel, thereby obtaining 0.78 g (yield: 61%) of the title compound (IIb-2).

Yellow oil.

IR (NaCl, cm$^{-1}$): 3304, 2924, 2856, 1464, 1374, 1120, 1076.

$^1$H-NMR (CDCl$_3$, δ): 0.75–0.96(m,6H), 1.00–1.65(m, 29H), 3.05–4.25(m,20H), 4.95–5.08 (m,1H).

Preparation Example 22:

Preparation of monosodium 2-(2-hydroxy-3-tetradecyloxypropylamino)ethyl phosphate [Monosodium (IIa-14)]:

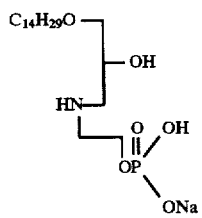

A 300-ml flask equipped with a stirrer was charged with 5.13 g (14.8 mmol) of 3-(2-hydroxyethylamino)-1-tetradecyloxy-2-propanol prepared from tetradecyl glycidyl ether and ethanolamine in the same manner as in Preparation Example 14, and 70 mol of tetrahydrofuran, 1.95 g (16.9 mmol) of 85% phosphoric acid and 3.54 g (30.7 mmol) of P$_2$O$_5$ were added thereto. The resultant mixture was stirred at 65° C. for 10 hours. After cooling the mixture to room temperature, 0.56 g of water was added to the mixture, stirring was conducted for 30 minutes, 5.0 g of 48% aqueous NaOH were added further. After concentrating the resultant reaction mixture under reduced pressure, the resultant residue was subjected to extraction with ethanol by means of a Soxhlet's extractor. The resultant extract was concentrated under reduced pressure, and the residue was purified by column chromatography on silica gel, thereby obtaining 2.32 g (yield: 34.9%) of the title compound monosodium (IIa-14).

Colorless solid.

IR (KBr, cm$^{-1}$): 3408, 2924, 2860, 1652, 1470, 1116, 978.

$^1$H-NMR (D$_2$O, δ): 0.80–1.10(m,3H), 1.26–1.95(m,24H), 3.02–4.64(m,11H).

Preparation Example 23:

Preparation of 3-[N-methyl-N-(2-phosphoryloxyethyl) amino]-1-tetradecyloxy-2-propyl phosphate (IIa-15):

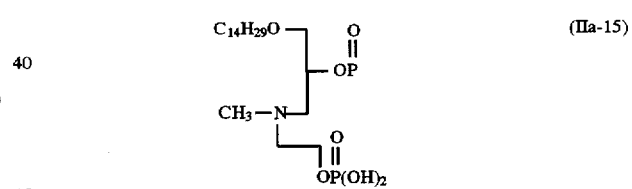

While stirring at –20° C., a chloroform solution of 2.94 g (8.52 mmol) of 3-[N-methyl-N-(2-hydroxyethyl)amino]-1-tetradecyloxy-2-propanol prepared from tetradecyl glycidyl ether and N-methyl-ethanolamine in the same manner as in Preparation Example 14 was added dropwise over 5 minutes to a solution of 1.46 g (9.52 mmol) of POCl$_2$ and 2.20 g (25.6 mmol) of pyridine in 30 ml of chloroform, which had been charged into a 100-ml flask equipped with a stirrer. The stirring was conducted further 30 minutes at –20° C., and 20 ml of water was added, followed by extraction with chloroform. The thus-obtained chloroform solution was concentrated under reduced pressure, and the residue was purified by column chromatography on silica gel, thereby obtaining 2.88 g (yield: 66.9%) of the title compound (IIa-15).

Colorless solid.

IR (KBr, cm$^{-1}$): 3464, 2924, 2852, 1462, 1072.

$^1$H-NMR (CDCl$_3$; CD$_3$OD, δ): 0.82–1.03(m,3H), 1.06–1.75(m,24H), 2.20–3.04(m,11H), 3.18–4.62(m,7H).

Preparation Example 24:

Preparation of N-(2-hydroxyethyl)-N,N-dimethyl-N-(3-(methoxy-2-hydroxypropyl)ammonium iodide (IIb-3):

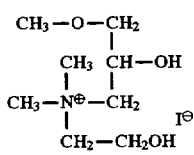

N-(3-Methoxy-2-hydroxypropyl)-N-methyl-2-hydroxyethylamine represented by the following formula was first prepared.

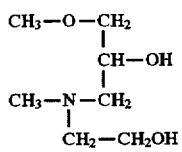

A 100-ml two-necked flask equipped with a reflux condenser and stirrer was charged with 8.8 g (0.1 mol) of methyl glycidyl ether, 9.0 g (0.12 mol) of 2-(methylamino)ethanol and 1.8 g of ethanol, and the contents were heated and stirred at 80° C. for 3 hours in a nitrogen atmosphere. After completion of the reaction, distillation was conducted, thereby obtaining 14.5 g (yield: 89%) of the above-mentioned compound.

Colorless oil.

IR (NaCl, cm$^{-1}$): 3396, 2892, 1448, 1324, 1192, 1030, 874.

$^1$H-NMR (CDCl$_3$, δ): 2.33(s,3H), 2.37–2.72(m,4H), 3.32–3.47(m,2H), 3.39(s,3H), 3.64(t,2H,J=5.2 Hz), 3.84–3.96(m,1H).

A 100-ml flask equipped with a stirrer was then charged with 1.00 g (6.13 mmol) of N-(3-methoxy-2-hydroxypropyl)-N-methyl-2-hydroxyethylamine obtained above and 10 ml of diethyl ether, and 0.45 ml of methyl iodide was added, followed by stirring for 10 hours. After the resultant reaction mixture was concentrated under reduced pressure, the resultant residue was purified by column chromatography on silica gel, thereby obtaining 1.31 g (yield: 70%) of the title compound (IIb-3).

Yellow oil.

IR (NaCl, cm$^{-1}$): 3368, 2932, 2896, 1480, 1114, 972.

$^1$H-NMR (D$_2$O, δ): 3.26(s,6H), 3.41(s,3H), 3.46–3.75(m, 6H), 4.00–4.15(m,2H), 4.35–4.55(m,1H).

Preparation Example 25:

Preparation of N-(2-hydroxypropyl)-N,N-dimethyl-N-[3-(12-hydroxyoctadecyl)-2-hydroxypropyl]ammonium bromide (IIb-4):

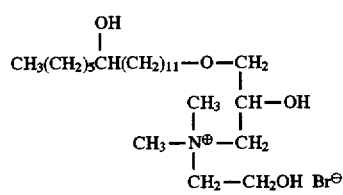

1-[N-Methyl-N-(2-hydroxyethyl)amino]-3-(12-hydroxyoctadecyl)-2-propanol was first prepared from 12-hydroxyoctadecyl glycidyl ether and N-methylethanolamine in the same manner as in the preparation of N-(3-methoxy-2-hydroxy-propyl)-N-methyl-2-hydroxyethylamine in Preparation Example 24. A 200-ml autoclave was charged with 6.3 g (15 mmol) of the thus-prepared compound, 100 ml of diethyl ether and 14.2 g of methyl bromide, and the resultant mixture was stirred at 48° C. for 8 hours. The reaction mixture was then concentrated under reduced pressure, and the resultant residue was dissolved in methanol. Diethyl ether was added to the solution to form crystals. The crystals were collected by filtration, thereby obtaining 6.9 g (yield: 90%) of the title compound (IIb-4).

Colorless crystals.

IR (KBr, cm$^{-1}$): 3320, 2920, 2852, 1470, 1122, 598.

$^1$H-NMR (CD$_3$OD, δ): 0.90(t,3H,J=6.5 Hz), 1.20–1.58 (m,30H), 3.25(s,6H), 3.33–4.29(m,12H).

Example 43

Inhibitory effect of the amine derivatives on DNA synthesis of epidermic keratinocyte:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (shown in Table 1) obtained in the above Preparation Examples was added thereto. Further, 0.2 μCi/ml of [$^3$H] thymidine was subsequently added to incubate the culture for 4 hours. After the supernatant was then removed by suction, and the well was washed 3 times with PBS(−), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells. The results are shown collectively in Table 10.

TABLE 10

| Amine derivative | Relative amount of [$^3$H] thymidine incorporated (%)* | |
|---|---|---|
| | 10 μM | 100 μM |
| (IIa-1) | 73.0 | 21.2 |
| (IIa-2) | 14.0 | 2.7 |
| (IIa-3) | 42.5 | 11.3 |
| (IIa-4) | 9.3 | 1.9 |
| (IIa-5) | 22.8 | 19.7 |
| (IIa-6) | 19.3 | 31.6 |
| (IIa-7) | 16.4 | 4.7 |
| (IIa-8) | 29.5 | 11.1 |
| (IIa-9) | 37.2 | 18.3 |
| (IIa-10) | 12.0 | 2.8 |
| (IIa-11) hydrochloride | 29.2 | 14.3 |
| (IIa-12) hydrochloride | 19.7 | 2.6 |
| (IIa-13) | 6.0 | 0.7 |
| (IIb-1) | 14.4 | 4.6 |
| (IIb-2) | 25.3 | 2.8 |
| (IIa-14) | 22.6 | 0.9 |
| (IIa-15) | 17.6 | 2.4 |

TABLE 10-continued

| Amine derivative | Relative amount of [$^3$H] thymidine incorporated (%)* | |
|---|---|---|
| | 10 µM | 100 µM |
| (IIb-3) | 65.5 | 12.0 |
| (IIb-4) | 12.4 | 3.2 |

*: Indicating the relative value where a control is assumed to be 100%.

It was apparent from the results shown in Table 10 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells turn insoluble membrane (cornified envelope), i.e., become keratinized. It is understood from this fact that the amine derivatives (IIa) and (IIb) according to the present invention are active in facilitating the keratinization of epidermis.

Example 44

Effect of the amine derivatives on the transglutaminase activity of epidermic keratinocyte:

(1) Determination of transglutaminase activity:

Keratinocytes cultured in a vegetative state in a 6-well plate were used. A medium in each well was removed by suction to add 2 ml of K-GM, to which no pituitary gland extract was added, to the well, thereby making a medium exchange. Thereafter, the amine derivative (IIb-1) was added thereto. After 24 hours, each well was washed 3 times with PBS(−), and the cells were then separated and collected by a rubber policeman. The thus-obtained cell suspension was centrifuged at 2,500 rpm for 10 minutes to collect the sediment. To this sediment, were added 200 µl of a buffer (a) [10 mM Tris-HCl buffer, 10 mM DTT, 0.5 mM EDTA; pH 7.4], followed by ultrasonication twice for 1 minute. The thus-obtained suspension was centrifuged at 25,000 rpm for 30 minutes to obtain a supernatant. This supernatant was divided into equiamount portions. To each of the portions, was added a reaction solution [a solution obtained by mixing 300 mM Tris-HCl buffer, pH 8.1; 100 µl of 60 mM CaCl$_2$; 100 µl of 30 mM DTT; 100 µl of distilled water containing 540 µg of dimethylcasein; 50 µl of 12 mM putrescine; 50 µl of 2.5 µCi [$^{14}$C] putrescine; and 100 µl of distilled water]. The thus-obtained mixture was incubated at 37° C. for 1 hour. After 600 µl of 10% trichloroacetic acid were then added to the mixture, and the resultant mixture was left at rest for 30 minutes, precipitate was collected on a nitrocellulose membrane of 0.45 µm. After this membrane was washed with 15 ml of 5% trichloroacetic acid (containing 1% of putrescine) chilled with ice water, the radioactivity of the precipitate on the membrane was determined by a liquid scintillation counter.

(2) Result:

The value (dpm) of transglutaminase activity where the amine derivative (IIb-1) has been added in an amount of 10 µM is shown in Table 11.

TABLE 11

| | Transglutaminase activity value (dpm) |
|---|---|
| Control | 731.3 |
| Amine derivative (IIb-1) | 3629.9 |

It is understood from the results shown in Table 11 that the amine derivatives (IIa) and (IIb) have an effect of markedly enhancing the transglutaminase activity of epidermic keratinocytes.

Example 45

Effect of the amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (shown in Table 12) in a concentration of 0.025% were applied 5 times a week to their corresponding groups of mice for 6 weeks in a dose of 80 µl. As a control, ethanol alone was applied in a dose of 80 µl like the samples.

After completion of the application, the degree of wrinkles was visually observed to rank the samples in accordance with the following standard (wrinkle index). The results are shown in Table 12.

(Wrinkle index; evaluation standard)

1: Wrinkles were completely removed;
2: Wrinkles were scarcely observed;
3: Wrinkles were somewhat observed;
4: Wrinkles were observed to a great extent.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 12.

TABLE 12

| Amine derivative | Wrinkle index | Area percent by image analysis (%) |
|---|---|---|
| Control | 3.75 ± 0.09 | 6.42 ± 0.63 |
| (IIa-1) | 2.89 ± 0.18 | 2.91 ± 0.28 |
| (IIa-6) | 2.95 ± 0.16 | 3.10 ± 0.30 |
| (IIa-7) | 3.20 ± 0.28 | 3.80 ± 0.41 |
| (IIa-8) | 3.07 ± 0.27 | 3.47 ± 0.33 |
| (IIa-10) | 3.24 ± 0.30 | 4.01 ± 0.41 |
| (IIa-11) hydrochloride | 3.25 ± 0.21 | 4.04 ± 0.39 |
| (IIa-12) hydrochloride | 3.00 ± 0.19 | 3.26 ± 0.32 |
| (IIa-13) | 3.25 ± 0.25 | 4.04 ± 0.41 |
| (IIb-1) | 3.40 ± 0.10 | 4.51 ± 0.42 |
| (IIb-2) | 3.33 ± 0.25 | 4.29 ± 0.44 |
| Mono Na (IIa-14) | 3.19 ± 0.25 | 3.85 ± 0.33 |

TABLE 12-continued

| Amine derivative | Wrinkle index | Area percent by image analysis (%) |
| --- | --- | --- |
| (IIa-15) | 3.15 ± 0.20 | 3.73 ± 0.34 |
| (IIb-3) | 3.38 ± 0.20 | 4.32 ± 0.50 |
| (IIb-4) | 3.41 ± 0.15 | 4.48 ± 0.40 |

As apparent from the result shown in Table 12, the wrinkles formed on the backs of the hairless mice can be removed by applying the amine derivatives thereto.

Example 46

A W/O type cream having the following composition was obtained in accordance with the below-described preparation process.

| (Composition) | | (wt. %) |
| --- | --- | --- |
| (1) | Amine derivative (IIa-1) | 0.08 |
| (2) | Cholesterol | 0.5 |
| (3) | Cholesteryl isostearate | 1.0 |
| (4) | Polyether-modified silicone | 1.5 |
| (5) | Cyclic silicone | 20.0 |
| (6) | Methylphenylpolysiloxane | 2.0 |
| (7) | Methylpolysiloxane | 2.0 |
| (8) | Magnesium sulfate | 0.5 |
| (9) | 55% Ethanol | 5.0 |
| (10) | Carboxymethylchithin (Chithin Liquid HV, product of Ichimaru Pharcos Co., Ltd.) | 0.5 |
| (11) | Purified water | Balance |

(Preparation process)

Components (1)–(7) were heated to 80° C. to melt them, and the components (8)–(11) were added to the melt. The resultant mixture was intimately mixed to prepare a W/O type cream.

Example 47

An O/W type cream having the following composition was obtained in accordance with the below-described preparation process.

| (Composition) | | (wt. %) |
| --- | --- | --- |
| (1) | Polyoxyethylene (10) hardened castor oil | 1.0 |
| (2) | Sorbitan monostearate | 0.5 |
| (3) | Sodium stearoylmethyltaurine | 0.5 |
| (4) | Cetostearyl alcohol | 2.0 |
| (5) | Stearic acid | 1.8 |
| (6) | Amine derivative (IIa-4) | 0.001 |
| (7) | Cholesterol | 1.5 |
| (8) | Cholesteryl isostearate | 1.0 |
| (9) | Neopentyl glycol dicaprate | 8.0 |
| (10) | Methylpolysiloxane | 5.0 |
| (11) | Glycerol | 5.0 |
| (12) | Purified water | Balance |

(Preparation process)

Components (1)–(10) were heated to 80° C. to melt them, and the components (11)–(12) were added to the melt. The resultant mixture was intimately mixed to prepare an O/W type cream.

Example 48

A moisturizing sunscreen cream having the following composition was obtained in accordance with the below-described preparation process.

| (Composition) | | (wt. %) |
| --- | --- | --- |
| (1) | Amine derivative (IIa-15) | 0.0005 |
| (2) | Silicon-coated zinc oxide | 7.0 |
| (3) | 2-Ethylhexyl p-methoxycinnamate | 3.0 |
| (4) | Cholesteryl isostearate | 1.0 |
| (5) | Polyether-modified silicone | 2.0 |
| (6) | Methylpolysiloxane | 5.0 |
| (7) | Cyclic silicone | 15.0 |
| (8) | Magnesium sulfate | 1.0 |
| (9) | Glycerol | 5.0 |
| (10) | Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 49

A pack having the following composition was obtained in accordance with the below-described preparation process.

| (Composition) | | (wt. %) |
| --- | --- | --- |
| (1) | Amine derivative (IIa-11) hydrochloride | 0.05 |
| (2) | Polyvinyl alcohol | 15.0 |
| (3) | Sodium carboxymethylcellulose | 5.0 |
| (4) | Propylene glycol | 3.0 |
| (5) | Ethanol | 8.0 |
| (6) | Purified water | Balance |
| (7) | Perfume base | 0.5 |
| (8) | Antiseptic, oxidizing agent | q.s. |

(Preparation process)

Components (1)–(8) were heated to 70° C. to melt them, and then cooled, thereby preparing a pack.

Example 50

An ointment having the following composition was obtained in accordance with the below-described preparation process.

| (Composition) | | (wt. %) |
| --- | --- | --- |
| (1) | Amine derivative (IIb-1) | 0.005 |
| (2) | White petrolatum | Balance |
| (3) | Cholesteryl isostearate | 3.0 |
| (4) | Liquid paraffin | 10.0 |
| (5) | Glyceryl ether | 1.0 |
| (6) | Glycerol | 10.0 |

(Preparation process)

Components (1)–(6) were heated to 80° C. to melt them, and then cooled, thereby preparing an ointment.

The dermatologic preparations according to the present invention, which were prepared in Examples 46–50, had excellent effects of preventing the occurrence of wrinkles and smoothing or removing wrinkles and moreover inhibited parakeratosis, epidermic hypertrophy and metabolic aberration of lipid and were excellent in recovery of normal functions and maintenance of homeostasis.

Preparation Example 26:

Preparation of 1-(2-hydroxyethylamino)-2-octadecanol (IIc-1):

$$C_{16}H_{33}-\underset{\underset{OH}{|}}{CH}-CH_2-\underset{\underset{H}{|}}{N}-(CH_2)_2-OH \quad \text{(IIc-1)}$$

A 300-ml flask equipped with a stirrer and a dropping funnel was charged with 45.8 g (0.75 mol) of ethanolamine and 9 g of ethanol. While stirring the mixture at 80° C., 13.4 g (50 mmol) of 1,2-epoxyoctadecane were added dropwise over 2 hours. Water was added to the resultant reaction mixture, and white crystals formed were collected by filtration, washed with water and then recrystallized from methanol, thereby obtaining 12.3 g (yield: 74.6%) of the title compound (IIc-1).

Colorless solid.

Melting point: 84.5°–86.0° C.

IR (KBr, cm$^{-1}$): 3400, 2920, 2852, 1472, 1126, 1076.

$^1$H-NMR (CDCl$_3$, δ): 0.82–0.96(m,3H), 1.14–1.51(m, 31H), 2.42–2.88(m,7H), 3.69(t,J=4.8 Hz,2H).

Preparation Example 27:

Preparation of 1-[N-(2-hydroxyethyl)-N-methylamino]-2-octadecanol (IIc-2):

$$C_{16}H_{33}-\underset{\underset{OH}{|}}{CH}-CH_2-\underset{\underset{CH_3}{|}}{N}-(CH_2)_2-OH \quad \text{(IIc-2)}$$

A 300-ml flask equipped with a stirrer was charged with 26.85 g (0.1 mol) of 1,2-epoxyoctadecane, 7.51 g (0.1 mol) of N-methylethanolamine and 50 ml of ethanol, and the contents were stirred at 80° C. for 18 hours. After the solvent was distilled off under reduced pressure, the resultant residue was purified by column chromatography on silica gel, thereby obtaining 23.0 g (yield: 67%) of the title compound (IIc-2).

Colorless solid.

Melting point: 39.0°–40.6° C.

IR (NaCl, cm$^{-1}$): 3392, 2920, 2852, 1660, 1466, 1300, 1080, 1042, 874.

$^1$H-NMR (CDCl$_3$, δ): 0.82–0.96(m,3H), 1.12–1.55(m, 30H), 2.33(s,3H), 2.34–2.77(m,6H), 3.55–3.84(m,3H).

Preparation Example 28:

Preparation of 2-(2-hydroxyethylamino)-3,7,11,15-tetramethyl-1,3-hexadecanediol (IIc-3):

(IIc-3) structure shown with CH$_3$ branches and CH$-$CH$-$N$-$(CH$_2$)$_2$$-$OH group with OH and H substituents.

A 100-ml two-necked flask equipped with a stirrer and a dropping funnel was charged with 8.79 g (0.14 mol) of ethanolamine and 20.0 g of ethanol. While heating and stirring the mixture at 80° C. in a nitrogen atmosphere, 3.01 g (9.6 mmol) of 2,3-epoxy-3,7,11,15-tetramethyl-1,3-hexadecanediol were added dropwise over 1 hour. After heating and stirring the mixture further for 2 hours, the resultant reaction mixture was concentrated under reduced pressure, and the resultant residue was purified by column chromatography on silica gel, thereby obtaining 3.02 g (yield: 84%) of the title compound (IIc-3).

Yellow solid.

Melting point: 49.1°–50.2° C.

IR (KBr, cm$^{-1}$): 3388, 3276, 2920, 2852, 1464, 1380, 1058, 1034.

$^1$H-NMR (CDCl$_3$, δ): 0.80–0.95(m,15H), 0.98–1.68(m, 21H), 2.44(t,J=4.3 Hz,1H), 2.72–3.08(m,6H), 3.58–3.66(m, 4H).

Preparation Example 29:

Preparation of 3-(2-hydroxyethylamino)-4-tetradecyloxy-2-methyl-2-butanol (IIc-4):

$$\underset{}{CH_3}\ \underset{}{CH_2OC_{14}H_{29}} \quad \text{(IIc-4)}$$
$$CH_3-\underset{\underset{OH}{|}}{CH}-\underset{}{CH}-\underset{\underset{H}{|}}{N}-(CH_2)OH$$

A 100-ml two-necked flask equipped with a stirrer and a dropping funnel was charged with 15.3 g (16.7 mmol) of ethanolamine and 5.0 g of ethanol. While heating and stirring the mixture at 80° C. in a nitrogen atmosphere, an ethanol solution of 5.00 g (16.7 mmol) of 1-tetradecyloxy-3-methyl-2-butene oxide was added dropwise over 3 hours. After heating and stirring the mixture further for 16 hours, the resultant reaction mixture was concentrated under reduced pressure, and the resultant residue was purified by column chromatography on silica gel, thereby obtaining 3.47 g (yield: 58%) of the title compound (IIc-4).

Pale yellow oil.

IR (NaCl, cm$^{-1}$): 3384, 2924, 2852, 1462, 1374, 1114, 1060.

$^1$H-NMR (CDCl$_3$, δ): 0.88(t,J=6.4 Hz,3H), 1.06–1.72(m, 30H), 2.55(dd,J=4.1 Hz,6.4 Hz,1H), 2.63–3.05(m,5H), 3.30–3.80(m,6H).

Preparation Example 30:

A reaction was conducted in the same manner as in Preparation Example 29 except that 1-tetradecyoxy-2-butene oxide was used in place of 1-tetradecyloxy-3-methyl-2-butene oxide in Preparation Example 29, thereby preparing the following amine derivative (IIc-5).

$$\underset{}{CH_2OC_{14}H_{29}} \quad \text{(IIc-5)}$$
$$CH_3-\underset{\underset{OH}{|}}{CH}-\underset{}{CH}-\underset{\underset{H}{|}}{N}-(CH_2)OH$$

Pale yellow solid.

Melting point: 54.4°–55.4° C.

IR (KBr, cm$^{-1}$): 3280, 2920, 2852, 1468, 1374, 1116, 1060.

$^1$H-NMR (CDCl$_3$, δ): 0.88(t,J=6.4 Hz,3H), 1.08–1.68(m, 27H), 2.41(brs,3H), 2.65(ddd,J=6.2 Hz,4.1 Hz,4.1 Hz,1H), 2.83(t,J=2.3 Hz,2H), 3.30–3.78(m,6H), 3.90(dq,J=3.9 Hz,6.2 Hz,1H).

Preparation Example 31:

Preparation of 2-(9-octadecenylamino)-1-ethanol (IIc-6):

$$C_8H_{17}\diagdown \qquad \diagup (CH_2)_8-\underset{\underset{H}{|}}{N}-(CH_2)_2OH \quad \text{(IIc-6)}$$
$$\qquad CH=CH$$

A 100-ml eggplant type flask equipped with a stirrer was charged with 1.40 g (37.2 mmol) of LiAlH$_4$ and 30 ml of tetrahydrofuran. While heating and stirring the contents at room temperature in an N$_2$ atmosphere, a tetrahydrofuran solution of 1.67 g (5.12 mmol) of N-(9-octadecenoyl)ethanolamine was added dropwise over 10 minutes. After the mixture was heated to 60° C. and stirred for 16 hours, the resultant reaction mixture was cooled to room temperature, and 14 g of 5% aqueous KOH. After a salt deposited was separated by filtration, the filtrate was concentrated under reduced pressure, and the resultant residue was purified by column chromatography on silica gel, thereby obtaining 0.96 g (yield: 65%) of the title compound (IIc-6).

Pale yellow oil.

IR (NaCl, cm$^{-1}$): 3328, 2920, 2852, 1458, 1376, 1118, 1060.

$^1$H-NMR (CDCl$_3$, δ): 0.88(t,J=6.6 Hz,3H), 1.15–1.65(m, 24H), 1.88–2.15(m,4H), 2.35(brs,2H), 2.61(t,J=7.3 Hz,2H), 2.76(t,J=5.3 Hz,2H), 3.64(t,J=5.3 Hz,2H), 5.22–5.48(m, 5H).

Preparation Examples 32–33:

Reactions were conducted in the same manner as in Preparation Example 31 except that N-octadecanoylethanolamine and N-methyl-branched isostearoylethanolamine were respectively used in place of N-(9-octadecenoyl)ethanolamine in Preparation Example 31, thereby synthesizing the following amine derivatives (IIc-7) and (IIc-8).

$$C_{18}H_{37}-\underset{H}{N}-(CH_2)_2OH \quad \text{(IIc-7)}$$

$$CH_3(CH_2)_\alpha\underset{CH_3}{CH}(CH_2)_\beta-\underset{H}{N}-(CH_2)_2OH \quad \text{(IIc-8)}$$

(in the formula, $\alpha$ and $\beta$ denote numbers satisfying the following relationship: $\alpha+\beta=11-17$, $\alpha=4-10$, $\beta=5-11$, and having a distribution that the peaks of $\alpha$ and $\beta$ are 7 and 8, respectively.)

(IIc-7):
Colorless solid.
Melting point: 57.3°–58.2° C.
IR (KBr, cm$^{-1}$): 3370, 2914, 2848, 1467, 1035.
$^1$H-NMR (CDCl$_3$, $\delta$): 0.88(t,J=6.7 Hz,3H), 1.04–1.75(m, 32H), 2.42(brs,2H), 2.61(t,J=7.3 Hz,2H), 2.77(t,J=5.1 Hz,2H), 3.65(t,J=5.1 Hz,2H).

(IIc-8):
Colorless oil.
IR (NaCl, cm$^{-1}$): 3196, 2924, 2856, 1460, 1376, 1122, 1062.
$^1$H-NMR (CDCl$_3$, $\delta$): 0.77–1.00(m,6H), 1.14–1.78(m, 29H), 2.24–2.56(m,2H), 2.62(t,J=7.3 Hz,2H), 2.77(t,J=5.1 Hz,2H), 3.65(t,J=5.1 Hz,2H).

Preparation Example 34:

Preparation of monosodium 2-[N-(2-hydroxyoctadecyl)-N-methylamino]ethyl phosphate [Monosodium (IIc-8)]:

$$C_{16}H_{33}-\underset{OH}{CH}-CH_2-\underset{CH_3}{N}-(CH_2)_2-\underset{O}{\overset{OH}{O-P}}-ONa \quad \text{Monosodium (IIc-8)}$$

A 200-ml flask equipped with a stirrer was charged with 5.10 g (14.8 mmol) of the amine derivative (IIc-2) obtained in Preparation Example 27, 50 mol of tetrahydrofuran and 3.54 g (30.7 mmol) of 85% phosphoric acid, and the contents were stirred at 65° C. for 7 hours. After allowing the mixture to cool, 0.56 g of water was added to stir the mixture for 30 minutes. Then, 2.38 g of NaOH and 3 g of water were added to the mixture, and the resultant reaction mixture was stirred for 30 minutes, followed by concentration under reduced pressure. The resultant residue was subjected to extraction with ethanol by means of a Soxhlet's extractor. After the solvent was distilled off under reduced pressure, the resultant residue was purified by column chromatography on silica gel, thereby obtaining 0.75 g (yield: 11%) of the title compound.

Colorless solid.
IR (KBr, cm$^{-1}$): 3296, 2920, 2852, 1470, 1148, 1074, 938.
$^1$H-NMR (CD$_3$OD, $\delta$): 0.78–0.98(m,3H), 1.04–1.87(m, 30H), 2.82–3.68(m,7H), 3.75–4.32(m,3H).

Example 51

Effect of the amine derivatives on wrinkles formed on hairless mice by exposure to UVB:

(1) Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (IIc-1)–(IIc-8) in a concentration of 0.025% were applied 5 times a week to their corresponding groups of mice for 6 weeks in a dose of 80 μl. As a control, ethanol alone was applied in a dose of 80 μl like the samples.

After completion of the application, the degree of wrinkles was visually observed to rank the samples in accordance with the following standard (wrinkle index). The results are shown in Table 13.

(Wrinkle index; evaluation standard)
1: Wrinkles were completely removed;
2: Wrinkles were scarcely observed;
3: Wrinkles were somewhat observed;
4: Wrinkles were observed to a great extent.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 13.

TABLE 13

| Amine derivative | Wrinkle index | Area percent by image analysis (%) |
|---|---|---|
| Control | 3.75 ± 0.09 | 6.42 ± 0.63 |
| (IIc-1) | 3.60 ± 0.10 | 6.08 ± 0.51 |
| (IIc-2) | 3.20 ± 0.27 | 3.88 ± 0.35 |
| (IIc-3) | 3.45 ± 0.31 | 4.67 ± 0.41 |
| (IIc-4) | 3.13 ± 0.15 | 3.66 ± 0.32 |
| (IIc-6) | 3.00 ± 0.21 | 3.26 ± 0.30 |
| (IIc-7) | 2.90 ± 0.17 | 2.92 ± 0.25 |
| Mono Na (IIc-8) | 3.40 ± 0.12 | 4.51 ± 0.41 |

As apparent from the result shown in Table 13, the wrinkles formed on the backs of the hairless mice can be removed by applying the amine derivatives (IIc-1)–(IIc-8) thereto.

Example 52

Inhibitory effect of the amine derivatives on DNA synthesis of epidermic keratinocyte:

(1) Method:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (IIc-1)–(IIc-8) obtained in the above Preparation Examples was added thereto. Further, 0.2 µCi/ml of [$^3$H] thymidine was subsequently added to incubate the culture for 4 hours. After the supernatant was then removed by suction, and the well was washed 3 times with PBS(−), 500 µl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells. The results are shown in Table 14.

TABLE 14

| Amine derivative | Relative amount of [$^3$H] thymidine incorporated (%)* | |
|---|---|---|
| | 10 µM | 100 µM |
| (IIc-1) | 48.4 | 8.9 |
| (IIc-2) | 63.2 | 14.6 |
| (IIc-3) | 5.2 | 0.9 |
| (IIc-4) | 9.7 | 1.9 |
| (IIc-5) | 14.3 | 4.3 |
| (IIc-6) | 23.0 | 4.7 |
| (IIc-7) | 51.6 | 10.1 |
| Mono Na (IIc-8) | 6.7 | 2.9 |

*: Indicating the relative value where a control is assumed to be 100%.

It was apparent from the results shown in Table 14 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells lead to insoluble membrane (cornified envelope), i.e., become keratinized. It is understood from this fact that the amine derivatives according to the present invention are active in facilitating the keratinization of epidermis.

Example 53

A W/O type cream having the following composition was obtained in accordance with the below-described preparation process.

| (Composition) | (wt. %) |
|---|---|
| (1) Amine derivative (IIc-1) | 0.01 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process) Components (1)–(7) were heated to 80° C. to melt them, and the components (8)–(11) were added to the melt. The resultant mixture was intimately mixed to prepare a W/O type cream.

Example 54

An O/W type cream having the following composition was obtained in accordance with the below-described preparation process.

| (Composition) | (wt. %) |
|---|---|
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (IIc-5) | 0.001 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 55

A moisturizing sunscreen cream having the following composition was obtained in accordance with the below-described preparation process.

| (Composition) | (wt. %) |
|---|---|
| (1) Amine derivative (IIc-4) | 0.05 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 56

A pack having the following composition was obtained in accordance with the below-described preparation process.

| (Composition) | (wt. %) |
|---|---|
| (1) Monosodium amine derivative (IIc-8) | 0.05 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 57

An ointment having the following composition was obtained in accordance with the below-described preparation process.

| (Composition) | (wt. %) |
| --- | --- |
| (1) Amine derivative (IIc-6) | 0.075 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations according to the present invention, which were prepared in Examples 53–57, had excellent effects of preventing the occurrence of wrinkles and smoothing or removing wrinkles and moreover inhibited parakeratosis, epidermic hypertrophy and metabolic aberration of lipid and were excellent in recovery of normal functions and maintenance of homeostasis.

Preparation Example 35:

Preparation of 1-(2-hydroxyethylamino)-2,16-hexadecanediol (IId-1):

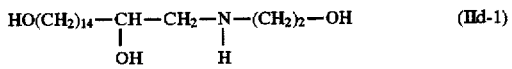

A 300-ml three-necked flask equipped with a stirrer, dropping funnel and $N_2$ inlet tube was charged with 40 ml of dimethyl sulfoxide and 1.2 g (30 mmol) of 60% sodium hydride. The contents were stirred at 75° C. for 1.5 hours in an $N_2$ atmosphere and then cooled to room temperature. To this mixture, a solution of 8.93 g (25 mmol) of methyltriphenylphosphonium bromide in 40 ml of dimethyl sulfoxide was added dropwise over 10 minutes. The resultant mixture was stirred further for 20 minutes at room temperature. To this mixture, a solution of 3.27 g (10 mmol) of 15-(2-tetrahydropyranyloxy)pentadecanal in 15 ml of THF was added dropwise over 5 minutes, followed by stirring further for 30 minutes. After completion of the reaction, the reaction mixture was added with water and subjected to extraction with hexane, followed by concentration under reduced pressure. Thereafter, the resultant residue was purified by flash column chromatography on silica gel, thereby obtaining 1.49 g (yield: 46%) of 1-(2-tetrahydropyranyloxy)-15-hexadecene.

A 500-ml flask equipped with a stirrer was charged with 1.49 g (4.6 mmol) of 1-(2-tetrahydropyranyloxy)-15-hexadecene, 70 ml of THF, 70 ml of methanol and 19 mg (0.1 mmol) of p-toluenesulfonic acid, and the contents were stirred at 40° C. for 12 hours. After completion of the reaction, the reaction mixture was concentrated under reduced pressure. The resultant residue was added with a 5% aqueous solution of $NaHCO_3$ and subjected to extraction with chloroform, and the solvent was distilled off under reduced pressure.

A 500-ml flask equipped with a stirrer and $N_2$ inlet tube was charged with this residue, 60 ml of dichloromethane and 2.64 g (15.3 mmol) of m-chloroperbenzoic acid, and the contents were stirred at room temperature for 3 days. After completion of the reaction, the reaction mixture was added with a 5% aqueous solution of $NaHCO_3$ and subjected to extraction with chloroform, the solvent was distilled off under reduced pressure, and the residue was then purified by chromatography on silica gel, thereby obtaining 0.89 g (yield: 76%) of 1,2-epoxy-16-hexadecanol.

A 50-ml two-necked flask equipped with a stirrer, dropping funnel and $N_2$ inlet tube was charged with 4.14 g (68 mmol) of ethanolamine and 0.8 g of ethanol. While heating and stirring the mixture at 80° C. in an $N_2$ atmosphere, an ethanol solution of 0.87 g (3.4 mmol) of 1,2-epoxy-16-hexadecanol was added dropwise over 1.5 hours. The resultant mixture was stirred further for 2 hours at 80° C. After completion of the reaction, ethanol and excess ethanolamine were distilled off under reduced pressure, and the resultant residue was purified by flash column chromatography on silica gel, thereby obtaining 0.72 g (yield: 68%) of the title compound (IId-1).

Colorless powder.

Melting point: 102.8° C.

IR (KBr, $cm^{-1}$): 3364, 2920, 2852, 1464, 1350, 1120, 1056.

$^1$H-NMR ($CD_3OD$, δ): 1.16–1.64(m,26H), 2.47–2.86(m, 4H), 3.37–3.77(m,5H).

Preparation Example 36:

Preparation of 1-(2-hydroxyethylamino)-12-methyl-2,12-heneicosanediol (IId-2):

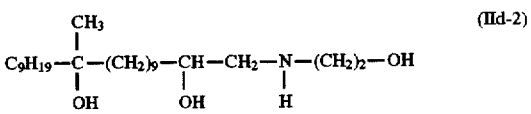

A 200-ml three-necked flask equipped with a stirrer, dropping funnel and $N_2$ inlet tube was charged with 1.22 g (50 mmol) of Mg for a Grignard reagent and 50 ml of anhydrous tetrahydrofuran. While stirring the contents at room temperature in an $N_2$ atmosphere, 11.66 g (50 mmol) of 1-bromo-10-undecene were added dropwise over 1 hour. After completion of the dropping, the resultant mixture was stirred further for 1 hour at room temperature. To this mixture, 8.52 g (50 mmol) of 2-undecanone were added, followed by stirring at room temperature for 1 hour. The resultant reaction mixture was added with an aqueous solution of $NH_4Cl$ and subjected to extraction with isopropyl ether, and the resultant extract was concentrated under reduced pressure.

The thus-obtained residue was transferred to a 200-ml flask equipped with a stirrer, to which 50 ml of dichloromethane and 12.18 g (60 mmol) of m-chloroperbenzoic acid were added. The contents were stirred at room temperature for 48 hours. Solids deposited were separated by filtration, and the resultant filtrate was concentrated under reduced pressure, and the residue was purified by chromatography on silica gel, thereby obtaining 10.16 g (yield: 59.7%) of 20,21-epoxy-9-methyl-9-heneicosanol.

A 50-ml two-necked flask equipped with a stirrer, dropping funnel and $N_2$ inlet tube was charged with 18.3 g (300 mmol) of ethanolamine and 3.8 g of ethanol. While heating and stirring the mixture at 80° C. in an $N_2$ atmosphere, 5.11 g (15 mmol) of 20,21-epoxy-9-methyl-9-heneicosanol were added dropwise over 1.5 hours. After completion of the dropping, ethanol and excess ethanolamine were distilled off under reduced pressure, and the resultant residue was purified by flash column chromatography on silica gel, thereby obtaining 4.52 g (yield: 75%) of the title compound (IId-2).

Pale yellow oil.

IR (NaCl, $cm^{-1}$): 3352, 2928, 2856, 1458, 1372, 1130, 1048, 748.

$^1$H-NMR ($CDCl_3$, δ): 0.88(t,J=6.5 Hz,3H), 1.14(s,3H), 1.01–1.78(m,34H), 2.45–3.30(m,8H), 3.53–3.80(m,3H).

Preparation Example 37:

Preparation of 16-[N,N-bis(2-hydroxyethyl)amino]-1-hexadecanol (IId-3):

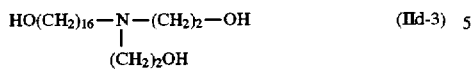

A 200-ml flask equipped with a stirrer was charged with 16.6 g (158 mmol) of diethanolamine and 20.1 g (79 mmol) of cyclohexadecanolide, to which 0.21 g (3.9 mmol) of sodium methoxide was added. The contents were stirred at 80° C. for 18 hours. After completion of the reaction, water was added, and solids deposited were collected by filtration and recrystallized from methanol, thereby obtaining 23.3 g (yield: 82%) of N,N-bis(2-hydroxyethyl)-16-hydroxyhexadecanamide.

A 500-ml flask equipped with a stirrer and reflux condenser was charged with 3.01 g (79.3 mmol) of LiAlH$_4$ and 200 ml of tetrahydrofuran. While stirring the mixture at room temperature in an N$_2$ atmosphere, 5.00 g (13.9 mmol) of N,N-bis(2-hydroxyethyl)-16-hydroxyhexadecanamide were added, followed by stirring at 65° C. for 18 hours. After cooling the reaction mixture to room temperature, 15 g of 3% aqueous KOH were added, and a salt deposited was separated by filtration. The solvent was then distilled off under reduced pressure, and the resultant residue was purified by column chromatography on silica gel, thereby obtaining 2.98 g (yield: 62%) of the title compound (IId-3).

Colorless solid.

Melting point: 67.6°–68.8° C.

IR (KBr, cm$^{-1}$): 3332, 2920, 2852, 1470, 1038. $^1$H-NMR (CDCl$_3$, δ): 1.15–1.68(m,31H), 2.52(t,J=7.6 Hz,2H), 2.66(t, J=5.2 Hz,4H), 3.54–3.68(m,6H).

Preparation Example 38:

Preparation of 16-(2-hydroxyethylamino)-1-(2-tetrahydropyranyloxy)hexadecane (IId-4):

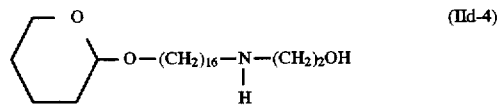

A reaction was conducted in the same manner as in Preparation Example 37 except that ethanolamine and methyl 16-(2-tetrahydropyranyloxy)hexadecanate were used in place of diethanolamine and cyclohexadecanolide, respectively, in Preparation Example 37, thereby obtaining the title compound (IId-4).

Colorless solid.

IR (KBr, cm$^{-1}$): 3276, 2920, 2852, 1474, 1368, 1116, 1064, 1032.

$^1$H-NMR (CDCl$_3$, δ): 0.90–1.98(m,34H), 2.10(brs,2H), 2.61(t,J=7.2 Hz,2H), 2.76(t,J=5.1 Hz,2H), 3.25–3.98(m, 6H), 4.52–4.65(m, 1H).

Preparation Example 39:

Preparation of 16-(2-hydroxyethylamino)-1-hexadecanol (IId-5):

A 200-ml flask equipped with a stirrer was charged with 4.82 g (12.5 mmol) of the amine derivative (IId-4) obtained in Preparation Example 38 and 100 ml of methanol, to which 1.45 ml (17.4 mmol) of 12N hydrochloric acid were added. The resultant mixture was stirred at 40° C. for 30 minutes. Then, 1.88 g (22.5 mmol) of 48% aqueous NaOH were added, followed by stirring at room temperature for 1 hour. The reaction mixture was concentrated under reduced pressure, and water was then added. Crystals thus deposited were collected by filtration and recrystallized from methanol, thereby obtaining 2.64 g (yield: 74%) of the title compound (IId-5).

Colorless solid.

Melting point: 80.0°–81.2° C.

IR (KBr, cm$^{-1}$): 3372, 2920, 2848, 1470, 1110, 1058.

$^1$H-NMR (CDCl$_3$, δ): 1.15–1.65(m,28H), 1.88(brs,3H), 2.62(t,J=7.0 Hz,2H), 2.76(t,J=5.2 Hz,2H), 3.54–3.68(m, 4H).

Example 58

Inhibitory effect of the amine derivatives on DNA synthesis of epidermic keratinocyte:

(1) Method:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (IId-1)–(IId-5) obtained in the above Preparation Examples was added thereto. Further, 0.2 μCi/ml of [$^3$H] thymidine was subsequently added to incubate the culture for 4 hours. After the supernatant was then removed by suction, and the well was washed 3 times with PBS(–), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

(2) Result:

The relative amounts of the [$^3$H] thymidine incorporated at the time each of the amine derivatives (IId-1) to (IId-5) has been added in amounts of 10 μM and 100 μM are shown in Table 1.

TABLE 15

| Amine derivative | Relative amount of [$^3$H] thymidine incorporated (%)* | |
|---|---|---|
| | 10 μM | 100 μM |
| (IId-1) | 52.6 | 18.3 |
| (IId-2) | 9.1 | 0.7 |
| (IId-3) | 16.2 | 3.9 |
| (IId-4) | 41.5 | 10.2 |
| (IId-5) | 8.8 | 1.1 |

*: Indicating the relative value where a control is assumed to be 100%.

It was apparent from Table 15 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells turn insoluble membrane (cornified envelope), i.e., become keratinized. It is understood from this fact that the amine derivatives according to the present invention are active in facilitating the keratinization of epidermis.

Example 59

Effect of the amine derivatives on wrinkles formed on hairless mice by exposure to UVB:

(1) Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (IId-1)–(IId-5) in a concentration of 0.025% were applied 5 times a week to their corresponding groups of mice for 6 weeks in a dose of 80 μl. As a control, ethanol alone was applied in a dose of 80 μl like the samples.

After completion of the application, the degree of wrinkles was visually observed to rank the samples in accordance with the following standard (wrinkle index). The results are shown in Table 16.

(Wrinkle index)

1: Wrinkles were completely removed;

2: Wrinkles were scarcely observed;

3: Wrinkles were somewhat observed;

4: Wrinkles were observed to a great extent.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 16.

TABLE 16

| Amine derivative | Wrinkle index | Area percent by image analysis (%) |
|---|---|---|
| Control | 3.75 ± 0.09 | 6.42 ± 0.63 |
| (IId-1) | 3.00 ± 0.43 | 3.26 ± 0.30 |
| (IId-2) | 3.21 ± 0.31 | 3.91 ± 0.41 |
| (IId-3) | 2.83 ± 0.42 | 2.72 ± 0.28 |
| (IId-5) | 2.50 ± 0.45 | 1.69 ± 0.18 |

As apparent from the result shown in Table 16, the wrinkles formed on the backs of the hairless mice can be removed by applying the amine derivatives (IId-1), (IId-2), (IId-3) and (IId-5) thereto.

Example 60

A W/O type cream having the following composition was obtained in accordance with the below-described preparation process.

| (Composition) | (wt. %) |
|---|---|
| (1) Amine derivative (IId-1) | 0.1 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 61

An O/W type cream having the following composition was obtained in accordance with the below-described preparation process.

| (Composition) | (wt. %) |
|---|---|
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (IId-3) | 0.001 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 62

A moisturizing sunscreen cream having the following composition was obtained in accordance with the below-described preparation process.

| (Composition) | (wt. %) |
|---|---|
| (1) Amine derivative (IId-5) | 0.05 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 63

A pack having the following composition was obtained in accordance with the below-described preparation process.

| (Composition) | (wt. %) |
| --- | --- |
| (1) Amine derivative (IId-3) hydrochloride | 0.05 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 64

An ointment having the following composition was obtained in accordance with the below-described preparation process.

| (Composition) | (wt. %) |
| --- | --- |
| (1) Amine derivative (IId-5) | 0.2 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations according to the present invention, which were prepared in Examples 60–64, had excellent effects of preventing the occurrence of wrinkles and smoothing or removing wrinkles and moreover inhibited parakeratosis of the skin, epidermic hypertrophy and metabolic aberration of lipid and were excellent in recovery of normal functions and maintenance of homeostasis.

Preparation Example 40

Preparation of 3-(2-hydroxyethylamino)-1-tetradecylthio-2-propanol (IIe-1):

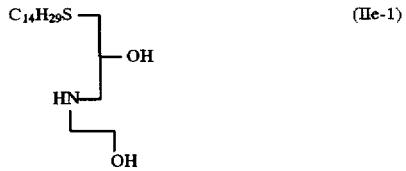

A 300-ml flask equipped with a stirrer and dropping funnel was charged with 61.1 g (1 mol) of ethanolamine and 61 g of ethanol. While stirring the contents at 80° C., a solution of 14.3 g (50 mmol) of 1-tetradecylthio-2,3-epoxypropane in 30 g ethanol was added dropwise over 3 hours. After completion of the dropping, the resultant reaction mixture was concentrated under reduced pressure, and the residue was recrystallized from hexane, thereby obtaining 15.8 g (yield: 91%) of the title compound (IIe-1).

Colorless solid.

Melting point: 71.4°–73.2° C.

IR (NaCl, cm$^{-1}$): 3364, 2914, 2842, 1464, 1428, 1077, 1038.

NMR (CDCl$_3$, δ): 1.11–1.67(m,24H), 2.47–3.19(m, 11H), 3.62–3.73(m,2H), 3.75–3.90(m, 1H).

Preparation Example 41:

Preparation of 3-[N-(2-hydroxyethyl)-N-methylamino]-2-hydroxy-1-propyl tetradecanate (IIe-2):

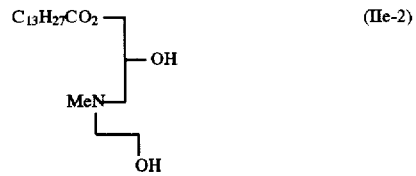

A 100-ml flask equipped with a stirrer and dropping funnel was charged with 6.01 g (80 mmol) of N-methylethanolamine, 50 ml of ethanol and 22.8 g (80 mmol) of glycidyl tetradecanate, and the contents were stirred at 80° C. for 2 hours. The resultant reaction mixture was concentrated under reduced pressure, and the residue was purified by chromatography on silica gel, thereby obtaining 17.5 g (yield: 60.8%) of the title compound (IIe-2).

Pale yellow oil.

IR (NaCl, cm$^{-1}$): 3384, 2928, 2852, 1730, 1460, 1174, 1030.

NMR (CDCl$_3$, δ): 0.76–0.92(m,3H), 1.02–1.70(m,22H), 2.14–2.77(m,9H), 3.29(br,2H), 3.54–4.22(m,5H).

Preparation Example 42:

Preparation of N-[3-(2-hydroxyethylamino)-2-hydroxypropyl]-12-hydroxyoctadecanamide (IIe-3):

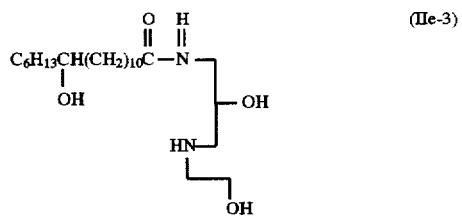

A 200-ml flask equipped with a stirrer was charged with 9.86 g (30 mmol) of ethyl 12-hydroxyoctadecanate, 2.73 g (30 mmol) of 3-amino-1,2-propanediol and 0.58 g (3 mmol) of 28% sodium methoxide, and the contents were stirred at 80° C. for 1 hour. After cooling the mixture to room temperature, 100 ml of pyridine and 5.72 g (30 mmol) of p-toluenesulfonyl chloride were added, followed by stirring at room temperature for 18 hours. The resultant reaction mixture was added with water and subjected to extraction with chloroform, followed by concentration under reduced pressure. Thereafter, the resultant residue was purified by column chromatography on silica gel, thereby obtaining N-[3-(4-methylphenylsulfonyloxy)-2-hydroxypropyl]-12-hydroxyoctadecanamide as an intermediate.

The intermediate obtained above was then transferred to a 200-ml flask equipped with a stirrer, to which 50 ml or ethanol and 18.3 g (300 mmol) of ethanolamine were added. The resultant mixture was stirred at 80° C. for 24 hours. Water was added to the resultant reaction mixture, followed by extraction with chloroform. The solvent was distilled off under reduced pressure, and the resultant residue was then purified by column chromatography on silica gel, thereby obtaining 4.92 g (yield: 39.4%) of the title compound (IIe-3).

Pale yellow solid.

Melting point: 97.7°–99.6° C.

IR (NaCl, cm$^{-1}$): 3300, 2924, 2848, 1642, 1548, 1468, 1126, 1072.

NMR (CDCl$_3$:CD$_3$OD=9:1, δ): 0.70–0.92(m,3H), 0.98–1.68(m,28), 2.13(t,J=7.5 Hz,2H), 2.53–2.94(m,4H), 3.07–3.89(m,6H).

Example 65

Effect of the amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (IIe-1), (IIe-2) and (IIe-3) in a concentration of 0.025% were applied 5 times a week to their corresponding-groups of mice for 6 weeks in a dose of 80 μl. As a control, ethanol alone was applied in a dose of 80 μl like the samples.

After completion of the application, the degree of wrinkles was visually observed to rank the samples in accordance with the following standard (wrinkle index). The results are shown in Table 17.
(Wrinkle index; evaluation standard)

1: Wrinkles were completely removed;

2: Wrinkles were scarcely observed;

3: Wrinkles were somewhat observed;

4: Wrinkles were observed to a great extent.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 17.

TABLE 17

| Amine derivative | Wrinkle index | Area percent by image analysis (%) |
|---|---|---|
| Control | 3.75 ± 0.09 | 6.42 ± 0.63 |
| (IIe-1) | 3.25 ± 0.28 | 4.04 ± 0.39 |
| (IIe-2) | 3.00 ± 0.20 | 3.26 ± 0.31 |
| (IIe-3) | 2.45 ± 0.21 | 1.53 ± 0.17 |

As apparent from the result shown in Table 17, the wrinkles formed on the backs of the hairless mice can be removed by applying the amine derivatives (IIe-1), (IIe-2) and (IIe-3) thereto.

Example 66

Inhibitory effect of the amine derivatives on DNA synthesis of epidermic keratinocyte:

a) Culture of human epidermic keratinocyte:

Human normal keratinocytes (trade name: Epipack) commercially available from Kurabo Industries Ltd. were purchased and used as keratinocyteso Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (IIe-1), (IIe-2) and (IIe-3) obtained in the above synthesis examples was added thereto. Further, 0.2 μCi/ml of [$^3$H] thymidine was subsequently added to incubate the culture for 4 hours. After the supernatant was then removed by suction, and the well was washed 3 times with PBS(−), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

TABLE 18

| | Relative amount of [$^3$H] thymidine incorporated (%)* | |
|---|---|---|
| Amine derivative | 10 μM | 100 μM |
| (IIe-1) | 43.1 | 7.4 |
| (IIe-2) | 29.8 | 6.7 |
| (IIe-3) | 31.0 | 9.4 |

*: Indicating the relative value where a control is assumed to be 100%.

It was apparent from Table 18 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells lead to insoluble membrane (cornified envelope), i.e., become keratinized. It is understood from this fact that the amine derivatives according to the present invention are active in facilitating the keratinization of epidermis.

Example 67

A W/O type cream having the following composition was obtained in accordance with the below-described preparation process.

| (Composition) | (wt. %) |
|---|---|
| (1) Amine derivative (IIe-3) | 0.08 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 68

An O/W type cream having the following composition was obtained in accordance with the below-described preparation process.

| (Composition) | (wt. %) |
|---|---|
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (IIe-1) | 0.001 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 69

A sunscreen cream having the following composition was obtained in accordance with the below-described preparation process.

| (Composition) | (wt. %) |
|---|---|
| (1) Amine derivative (IIe-3) | 0.05 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 70

A pack having the following composition was obtained in accordance with the below-described preparation process.

| (Composition) | (wt. %) |
|---|---|
| (1) Amine derivative (IIe-3) hydrochloride | 0.05 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 71

An ointment having the following composition was obtained in accordance with the below-described preparation process.

| (Composition) | (wt. %) |
|---|---|
| (1) Amine derivative (IIe-2) | 0.2 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations according to the present invention, which were prepared in Examples 67–71, had excellent effects of preventing the occurrence of wrinkles and smoothing or removing wrinkles and moreover inhibited parakeratosis, epidermic hypertrophy and metabolic aberration of lipid and were excellent in recovery of normal functions and maintenance of homeostasis.

Preparation Example 43:

Preparation of N-|2-(2-hydroxyethylamino)ethyl|-12-hydroxyoctadecanamide (IIf-1):

$$C_6H_{13}CH(OH)(CH_2)_{10}C(=O)NH-CH_2CH_2-NH-CH_2CH_2-OH \quad (IIf\text{-}1)$$

A 30-ml two-necked flask equipped with a stirrer and dropping funnel was charged with 2.08 g (20 mmol) of aminoethylaminoethanol and 0.054 g (1 mmol) of sodium methoxide. While heating and stirring the contents at 80° C. in an $N_2$ atmosphere, a solution of 3.29 g (10 mmol) of ethyl 12-hydroxystearate in 10 ml of THF was added dropwise over 2 hours. The resultant mixture was stirred further for 13 hours at 80° C. under reduced pressure. After completion of the reaction, the reaction mixture was poured into 500 ml of water, and precipitate formed was purified by flash column chromatography on silica gel, thereby obtaining 2.85 g (yield: 74%) of the title compound (IIf-1).

Colorless powder.

Melting point: 101.9°–102.4° C.

IR (KBr, $cm^{-1}$): 3292, 2920, 2852, 1642, 1552, 1470, 1068.

NMR ($CDCl_3$, δ): 0.90(t,J=6.6 Hz,3H), 1.18–1.71(m,3H), 2.19(t,J=7.8 Hz,2H), 2.70–2.77(m,4H), 3.29–3.68(m,5H).

Preparation Example 44:

A reaction was conducted in the same manner as in Preparation Example 43 except that methyl 12-hydroxydodecanate was used in place of ethyl 12-hydroxystearate in Preparation Example 43, thereby obtaining the following amine derivative (IIf-2).

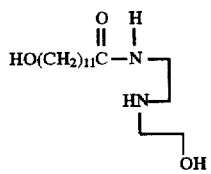
(IIf-2)

Pale yellow solid.

Melting point: 73.4°–74.0° C.

IR (KBr, cm$^{-1}$): 3284, 2924, 2848, 1628, 1554, 1468, 1388, 1040, 956.

$^1$H-NMR (CDCl$_3$, δ): 0.82–1.74(m,18H), 2.18(t,J=7.4 Hz,2H), 2.75–2.82(m,4H), 3.29–3.69(m,6H).

Example 72

Effect of the amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (IIf-1) and (IIf-2) in a concentration of 0.025% were applied 5 times a week to their corresponding groups of mice for 6 weeks in a dose of 80 μl. As a control, ethanol alone was applied in a dose of 80 μl like the samples.

After completion of the application, the degree of wrinkles was visually observed to rank the samples in accordance with the following standard (wrinkle index). The results are shown in Table 17.

(Wrinkle index; evaluation standard)

1: Wrinkles were completely removed;
2: Wrinkles were scarcely observed;
3: Wrinkles were somewhat observed;
4: Wrinkles were observed to a great extent.

TABLE 19

| Group | Wrinkle index |
|---|---|
| Control | 3.75 ± 0.09 |
| Amine derivative (IIf-1) | 2.95 ± 0.20 |
| Amine derivative (IIf-2) | 2.70 ± 0.19 |

As apparent from the result shown in Table 19, the wrinkles formed on the backs of the hairless mice were able to be removed by applying the amine derivatives (IIf-1) and (IIf-2) thereto.

In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown in Table 20.

TABLE 20

| Group | Area percent by image analysis (%) |
|---|---|
| Control | 6.42 ± 0.63 |
| Amine derivative (IIf-1) | 3.10 ± 0.31 |
| Amine derivative (IIf-2) | 2.31 ± 0.20 |

As apparent from the result shown in Table 20, the wrinkles formed on the backs of the hairless mice can be removed by applying the amine derivatives (IIf-1) and (IIf-2) thereto.

Example 73

Inhibitory effect of the amine derivatives on DNA synthesis of epidermic keratinocyte:

(1) Method:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 μl of K-GM, to which no pituitary gland extract was added, to the well, thereby making a medium exchange. Thereafter, each of the amine derivatives (IIf-1) and (IIf-2) obtained in the above Preparation Examples was added thereto. Further, 0.2 μCi/ml of [$^3$H] thymidine was subsequently added to incubate the culture for 4 hours. After the supernatant was then removed by suction, and the well was washed 3 times with PBS(−), 500 μl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

TABLE 21

| Amine derivative | Relative amount of [$^3$H] thymidine incorporated (%)* | |
|---|---|---|
|  | 10 μM | 100 μM |
| (IIf-1) | 7.1 | 1.5 |
| (IIf-2) | 52.3 | 11.3 |

*: Indicating the relative value where a control is assumed to be 100%.

It was apparent from Table 21 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells lead to insoluble membrane (cornified envelope), i.e., become keratinized. It is understood from this fact that the amine derivatives according to the present invention are active in facilitating the keratinization of epidermis.

Example 74

A W/O type cream having the following composition was obtained in accordance with the below-described preparation process.

| (Composition) | | (wt. %) |
|---|---|---|
| (1) | Amine derivative (IIf-1) | 0.08 |
| (2) | Cholesterol | 0.5 |
| (3) | Cholesteryl isostearate | 1.0 |
| (4) | Polyether-modified silicone | 1.5 |
| (5) | Cyclic silicone | 20.0 |
| (6) | Methylphenylpolysiloxane | 2.0 |
| (7) | Methylpolysiloxane | 2.0 |
| (8) | Magnesium sulfate | 0.5 |
| (9) | 55% Ethanol | 5.0 |
| (10) | Carboxymethylchithin (Chithin Liquid HV, product of Ichimaru Pharcos Co., Ltd.) | 0.5 |
| (11) | Purified water | Balance |

(Preparation process)

Components (1)–(7) were heated to 80° C. to melt them, and the components (8)–(11) were added to the melt. The resultant mixture was intimately mixed to prepare a W/O type cream.

Example 75

An O/W type cream having the following composition was obtained in accordance with the below-described preparation process.

| (Composition) | | (wt. %) |
|---|---|---|
| (1) | Polyoxyethylene (10) hardened castor oil | 1.0 |
| (2) | Sorbitan monostearate | 0.5 |
| (3) | Sodium stearoylmethyltaurine | 0.5 |
| (4) | Cetostearyl alcohol | 2.0 |
| (5) | Stearic acid | 1.8 |
| (6) | Amine derivative (IIf-2) | 0.001 |
| (7) | Cholesterol | 1.5 |
| (8) | Cholesteryl isostearate | 1.0 |
| (9) | Neopentyl glycol dicaprate | 8.0 |
| (10) | Methylpolysiloxane | 5.0 |
| (11) | Glycerol | 5.0 |
| (12) | Purified water | Balance |

(Preparation process)

Components (1)–(10) were heated to 80° C. to melt them, and the components (11)–(12) were added to the melt. The resultant mixture was intimately mixed to prepare an O/W type cream.

Example 76

A sunscreen cream having the following composition was obtained in accordance with the below-described preparation process.

| (Composition) | | (wt. %) |
|---|---|---|
| (1) | Amine derivative (IIf-2) | 0.05 |
| (2) | Silicon-coated zinc oxide | 7.0 |
| (3) | 2-Ethylhexyl p-methoxycinnamate | 3.0 |
| (4) | Cholesteryl isostearate | 1.0 |
| (5) | Polyether-modified silicone | 2.0 |

-continued

| (Composition) | | (wt. %) |
|---|---|---|
| (6) | Methylpolysiloxane | 5.0 |
| (7) | Cyclic silicone | 15.0 |
| (8) | Magnesium sulfate | 1.0 |
| (9) | Glycerol | 5.0 |
| (10) | Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 77

A pack having the following composition was obtained in accordance with the below-described preparation process.

| (Composition) | | (wt. %) |
|---|---|---|
| (1) | Amine derivative (IIf-2) hydrochloride | 0.05 |
| (2) | Polyvinyl alcohol | 15.0 |
| (3) | Sodium carboxymethylcellulose | 5.0 |
| (4) | Propylene glycol | 3.0 |
| (5) | Ethanol | 8.0 |
| (6) | Purified water | Balance |
| (7) | Perfume base | 0.5 |
| (8) | Antiseptic, oxidizing agent | q.s. |

(Preparation process)

Components (1)–(8) were heated to 70° C. to melt them, and then cooled, thereby preparing a pack.

Example 78

An ointment having the following composition was obtained in accordance with the below-described preparation process.

| (Composition) | | (wt. %) |
|---|---|---|
| (1) | Amine derivative (IIf-2) | 0.075 |
| (2) | White petrolatum | Balance |
| (3) | Cholesteryl isostearate | 3.0 |
| (4) | Liquid paraffin | 10.0 |
| (5) | Glyceryl ether | 1.0 |
| (6) | Glycerol | 10.0 |

(Preparation process)

Components (1)–(6) were heated to 80° C. to melt them, and then cooled, thereby preparing an ointment.

The dermatologic preparations according to the present invention, which were prepared in Examples 74–78, had excellent effects of preventing the occurrence of wrinkles and smoothing or removing wrinkles and moreover inhibited parakeratosis of the skin, epidermic hypertrophy and metabolic aberration of lipid and were excellent in recovery of normal functions and maintenance of homeostasis.

Preparation Example 79

Effect of amine derivatives on wrinkles formed on hairless mice by exposure to UVB:

Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm². The exposure was effected for 20 weeks. After confirming the fact that the mice had got wrinkles at their backs, they were divided into groups each consisting of 8 mice. Ethanol solutions (0.025%) separately containing sphingosine analogues (IIg-1) and (IIg-2) shown in Table 22 were applied 5 times a week to their corresponding groups of mice for 6 weeks in a dose of 80 µl. As a control, ethanol alone was applied in a dose of 80 µl like the samples.

TABLE 22

| Sphingosine analogue | Structure | Synthesis |
| --- | --- | --- |
| D-Erythro-spingosine (1a) | $C_{13}H_{27}$ ... NH₂ ... OH ... OH | Synthesized in accordance with Journal of Organic Chemistry, Vol. 53, 4395(1988). |
| DL-Erythro-dihydro-sphingosine (1b) | $C_{15}H_{31}$ ... NH₂ ... OH ... OH | Synthesized in accordance with Journal of Organic Chemistry, Vol. 29, 2783 (1964). |

After completion of the application, the degree of wrinkles was visually observed to rank the samples in accordance with the following standard (wrinkle index). The results are shown in Table 23.

(Wrinkle index; evaluation standard)

1: Wrinkles were completely removed;
2: Wrinkles were scarcely observed;
3: Wrinkles were somewhat observed;
4: Wrinkles were observed to a great extent.

TABLE 23

| Group | Wrinkle index |
| --- | --- |
| Control | 3.75 ± 0.09 |
| Sphingosine (IIg-1) | 3.20 ± 0.10 |
| Dihydrosphingosine (IIg-2) | 3.40 ± 0.36 |

As apparent from the result shown in Table 23, the wrinkles formed on the backs of the hairless mice were able to be removed by applying the sphingosine analogues (IIg-1) and (IIg-2) thereto.

In order to further analyze the particulars of wrinkles, skin replicas of the size of 1 cm² in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown in Table 24.

TABLE 24

| Group | Area percent by image analysis (%) |
| --- | --- |
| Control | 6.42 ± 0.63 |

TABLE 24-continued

| Group | Area percent by image analysis (%) |
| --- | --- |
| Sphingosine (IIg-1) | 5.41 ± 0.29 |
| Dihydrosphingosine (IIg-2) | 5.11 ± 0.28 |

As apparent from the result shown in Table 28, the wrinkles formed on the backs of the hairless mice can be removed by applying the sphingosine analogues (IIg-1) and (IIg-2) thereto.

Example 80

A W/O type cream having the following composition was obtained in accordance with the below-described preparation process.

| (Composition) | (wt. %) |
| --- | --- |
| (1) sphingosine (IIg-1) | 0.01 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 81

An O/W type cream having the following composition was obtained in accordance with the below-described preparation process.

| (Composition) | (wt. %) |
| --- | --- |
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Dihydrosphingosine (IIg-2) | 0.1 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 82

A sunscreen cream having the following composition was obtained in accordance with the below-described preparation process.

| (Composition) | (wt. %) |
|---|---|
| (1) Sphingosine (IIg-1) | 0.2 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 83

A pack having the following composition was obtained in accordance with the below-described preparation process.

| (Composition) | (wt. %) |
|---|---|
| (1) Sphingosine (IIg-1) | 0.05 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

Example 84

A pack having the following composition was obtained in accordance with the below-described preparation process.

| (Composition) | (wt. %) |
|---|---|
| (1) Sphingosine (IIg-1) | 0.005 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

The dermatologic preparations, which were prepared in Examples 80–84 and comprised the agent for preventing or smoothing wrinkles according to the present invention as an effective ingredient, had excellent effects of preventing the occurrence of wrinkles and smoothing or removing wrinkles.

Preparation Example 45:
Preparation of 1-benzylaminotridecane-2,3-diol (IIh-1):

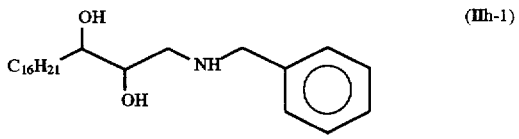

(1) Preparation of 1,2-epoxy-3-tridecanol:

A 500-ml flask equipped with a stirrer was charged with 23.8 g (0.12 mol) of 1-tridecen-3-ol, 25.0 g (0.145 mol) of m-chloroperbenzoic acid and 250 ml of benzene, and the contents were stirred at room temperature for 48 hours. After completion of the reaction, 200 ml of hexane. Solids deposited were separated by filtration, and the solvent was distilled off under reduced pressure. The resultant residue was purified by column chromatography on silica gel, thereby obtaining 19.0 g (yield: 74%) of 1,2-epoxy-3-tridecanol.

(2) Preparation of an amine derivative (IIh-1):

A 500-ml flask equipped with a stirrer was charged with 107 g (1 mol) of benzylamine, to which a solution of 5.2 g (71 mmol) of 1,2-epoxy-3-tridecanol in 170 ml of dioxane was added dropwise over 2 hours. After completion of the dropping, a reaction was conducted further for 12 hours at 80° C. Dioxane and excess benzylamine were distilled off under reduced pressure. The resultant residue was recrystallized from hexane, thereby obtaining 16.4 g (yield: 72%) of the title compound (IIh-1).

Pale yellow solid.

Melting point: 52.6°–53.0° C.

IR (KBr, cm$^{-1}$): 3352, 2920, 2854, 1473, 1107, 855, 696.
$^1$H-NMR (CDCl$_3$, δ): 0.90(t,3H), 1.25–1.55(m,16H), 2.6–3.0(m,2H), 3.5(m,2H), 3.75(m,2H), 7.2(m,5H).

Preparation Example 46:
Preparation of 1-aminotridecane-2,3-diol (IIh-2):

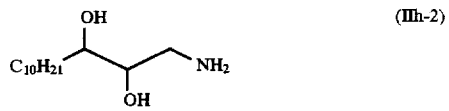

A 200-ml flask equipped with a stirrer was charged with 9.0 g (28 mmol) of the amine derivative (IIh-1) obtained in Preparation Example 45, 6.0 g (56 mmol) of 2,2-dimethoxypropane and 2 g (20 mmol) of sulfuric acid to react them at room temperature for 20 minutes. After neutralizing the reaction mixture with 2N aqueous NaOH, extraction with chloroform was conducted, followed by concentration under reduced pressure. A 300-ml autoclave was charged with the resultant residue, 1.0 g of 5% Pd/C and 60 ml of dioxane to conduct hydrogenolysis for 24 hours at room temperature under a hydrogen pressure of 5 atm. After the catalyst was separated by filtration, the filtrate was concentrated under reduced pressure. The resultant residue was charged into a 100-ml flask equipped with a stirrer, to which 15 ml of 2N HCl and 20 ml of tetrahydrofuran were added, followed by stirring at room temperature for 24 hours. The reaction mixture was neutralized with 2N aqueous NaOH, and solids deposited were collected by filtration and recrystallized from chloroform, thereby obtaining 3.43 g (yield: 53%) of the title compound (IIh-2).

Colorless solid.

Melting point: 98°–100° C.

IR (KBr, cm$^{-1}$): 3376, 3226, 2914, 2848, 1611, 1464, 1110 1080, 981.

$^1$H-NMR (CDCl$_3$, δ): 0.88(m,3H), 1.2–1.55(m,18H), 2.90 (m,2H), 3.44(m,1H), 3.71(m,1H).

Preparation Examples 47–48:

The following amine derivatives (IIh-3) and (IIh-4) were obtained in a manner similar to preparation Examples 45 and 46.

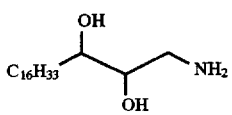
(IIh-3)

Colorless solid.
Melting point: 113°–117° C.
IR (KBr, cm$^{-1}$): 3376, 3304, 3226, 2920, 2848, 1611, 1464 1116, 1080, 984.
$^1$H NMR (CDCl$_3$, δ): 0.87(t,J=7 Hz,3H), 1.30(m,28H), 1.50(m,2H), 2.77(dd,J=6.0, 14.0 Hz,1H), 3.07(dd,J=4.0, 14.0 Hz,1H), 3.45(m,1H), 3.60(m,1H).

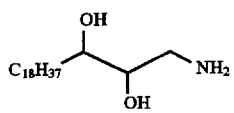
(IIh-4)

Colorless solid.
Melting point: 112.5–113.9° C.
IR (KBr, cm$^{-1}$): 3376, 3238, 2920, 2848, 1608, 1464, 1332, 987.
$^1$H-NMR (CDCl$_3$, δ): 0.87(t,J=7 Hz,3H), 1.25(m,32H), 1.45(m,2H), 2.76(dd,J=5.6,12.7 Hz,1H), 3.05(dd,J=3.5,12.7 Hz,1H), 3.42(m,1H), 3.60(m,1H).

Preparation Example 49:
Preparation of 3-aminononadecane-1,2-diol (IIh-5):

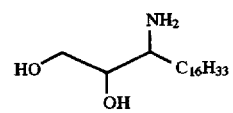
(IIh-5)

A 100-ml flask equipped with a stirrer was charged with 5.0 g (14 mmol) of 1,2-isopropylidenedioxy-3-nonadecanol, 10 ml of triethylamine and 30 ml of dichloromethane. While stirring the contents at 0° C., 2.4 g (21 mmol) of methanesulfonyl chloride were added. The resultant mixture was heated to room temperature and stirred for 2 hours to complete the reaction. The reaction mixture was added with water and subjected to extraction with dichloromethane, followed by concentration under reduced pressure. Thereafter, the resultant residue was purified by column chromatography on silica gel, thereby obtaining a methanesulfonylated intermediate. This intermediate was then transferred to a 100-ml flask equipped with a stirrer, to which 15 ml of dimethylformamide and 3.5 g (54 mmol) of NaN$_3$ were added. The contents were stirred at 80° C. for 15 hours. After cooling, the reaction mixture was added with water and subjected to extraction with diethyl ether, followed by concentration under reduced pressure. Thereafter, the resultant residue was purified by column chromatography on silica gel, thereby obtaining 4.6 g (86%) of an azide intermediate.

A 200-ml flask equipped with a stirrer was then charged with 0.3 g (7 mmol) of LiAlH$_4$ and 50 ml of tetrahydrofuran. While stirring the contents at room temperature, a tetrahydrofuran solution of 2.0 g (5.2 mmol) of the azide intermediate obtained above was added. After stirring the mixture at room temperature for 1 hour, 1.5 g of 5% aqueous KOH were added, and a salt deposited was separated by filtration. After the solvent was distilled off under reduced pressure, 12 ml of tetrahydrofuran and 8 ml of 2N HCl were added to the residue. The mixture was heated and stirred at 50° C. for 1 hour. After cooling the mixture to room temperature, it was neutralized with 2N aqueous NaOH, and solids deposited. were collected by filtration and recrystallized from chloroform, thereby obtaining 0.84 g (yield: 51%) of the title compound (IIh-5).

Colorless solid.
Melting point: 92°–93° C.
IR (KBr, cm$^{-1}$): 3394, 2920, 1608, 1467, 1338, 1065.
$^1$H-NMR (CDCl$_3$, δ): 0.88(t,J=7 Hz,3H), 1.3(m,30H), 2.77(m, 1H), 3.43(ddd,J=3.8,3.8,7.6 Hz,1H), 3.68(dd,J=3.8, 11.9 Hz,1H), 3.78(dd,J=3.8,11.9 Hz,1H).

Preparation Example 50:
The following amine derivative (IIh-6) was obtained in a manner similar to Preparation Example 49.

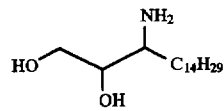
(IIh-6)

Colorless solid.
Melting point: 86°–89° C.
IR (KBr, cm$^{-1}$): 3388, 2920, 2850, 1608, 1464, 1338, 1062, 1002.
$^1$H-NMR (CDCl$_3$, δ): 0.87(t,J=7 Hz,3H), 1.3(m,26H), 2.78(m,1H), 3.45(ddd,J=4.5,4.5,8.7 Hz,1H), 3.69(dd,J=4.5, 12.4 Hz,1H), 3.78(dd,J=4.5,12.4 Hz,1H).

Preparation Example 51:
Preparation of 1-amino-2-octadecanol (IIh-7):

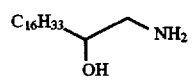
(IIh-7)

A 500-ml flask equipped with a stirrer was charged with 160 g (1.5 mol) of benzylamine, to which 29 g (0.11 mol) of 1,2-epoxyoctadecane were added dropwise over 3 hours while stirring at 100° C. Stirring was conducted further for 12 hours at 100° C. Benzyl alcohol was distilled off under reduced pressure, and the residue was charged into a 500-ml autoclave, to which 300 ml of ethanol and 10 g of 5% Pd/C were added to conduct hydrogenolysis for 48 hours at room temperature under a hydrogen pressure of 5 atm. After the catalyst was separated by filtration, the filtrate was concentrated under reduced pressure, and the residue was recrystallized from hexane, thereby obtaining 26.1 g (yield: 83%) of the title compound (IIh-7).

Colorless solid.
Melting point: 75.2°–76.5° C.
IR (KBr, cm$^{-1}$): 3377, 2927, 2855, 1647.
$^1$H-NMR (CDCl$_3$, δ): 0.90(t,J=7 Hz,3H), 1.25–1.50(m, 30H), 2.50(dd,J=8.4,13.0 Hz,1H), 2.84(dd,J=3.4,13.0 Hz,1H), 3.56(m,1H).

Preparation Example 52:
Preparation of 2-amino-1-octadecanol (IIh-8):

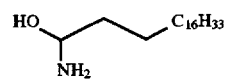
(IIh-8)

A 1-liter flask equipped with a stirrer and dropping funnel was charged with 20 g (70 mmol) of octadecane-1,2-diol, 0.7 g (3.5 mmol) of p-toluenesulfonic acid and 350 ml of dichloromethane. While stirring the contents at room temperature, 5.9 g (70 mmol) of dihydropyran were added dropwise. After stirring the mixture at room temperature for 30 minutes, it was neutralized with NaHCO$_3$ and concentrated under reduced pressure, and the resultant residue was then purified by column chromatography on silica gel, thereby obtaining 7.5 g (yield[: 29%) of 1-(2-tetrahydropyranyloxy)-2-octadecanol. This compound was charged into a 200-ml flask equipped with a stirrer, to which 5.1 g (50 mmol) of triethylamine and 50 ml of dichloromethane were added. Further, 3.8 g (33 mmol) of methanesulfonyl chloride were added at room temperature with stirring. After the resultant mixture was stirred at room temperature for 14 hours, the reaction mixture was added with water and subjected to extraction with dichloromethane, and the solvent was distilled off under reduced pressure. The resultant residue and 15 ml of dimethylformamide was charged into a 100-ml flask equipped with a stirrer, to which 5.5 g (83 mmol) of NaN$_3$ were added. The contents were stirred at 90° C. for 1.5 hours. After cooling the reaction mixture to room temperature, it was added with water and subjected to extraction with chloroform, followed by concentration under reduced pressure. Thereafter, the resultant residue was purified by column chromatography on silica gel, thereby obtaining 7.1 g (yield: 90%) of an azide intermediate.

A 100-ml flask equipped with a stirrer was charged with 3.4 g (8.6 mmol) of the azide intermediate, 0.02 g (0.1 mmol) of p-toluenesulfonic acid, 20 ml of methanol and 10 ml of tetrahydrofuran, and the contents were stirred at 40° C. for 1 hour. After neutralizing the mixture with NaHCO$_3$, it was concentrated under reduced pressure. A 200-ml flask equipped with a stirrer was then charged with 0.58 g (17.2 mmol) of LiAlH$_4$ and 50 ml of tetrahydrofuran, to which the residue obtained above was added. The contents were stirred at room temperature for 18 hours. To the mixture, were added 2.5 g of 5% aqueous KOH, and a salt deposited was separated by filtration. The filtrate was then concentrated under reduced pressure, and the resultant residue was purified by column chromatography on silica gel, thereby obtaining 1.77 g (yield: 72%) of the title compound (IIh-8).

Colorless powder.

Melting point: 80.8°–81.9° C.

IR (KBr, cm$^{-1}$): 3340, 2920, 2848, 1470, 1059, 717.

$^1$H-NMR (CDCl$_3$, δ): 0.90(t,3H), 1.25–1.50(m,30H), 2.80 (m,1H), 3.25(dd,J=7.0,11.0 Hz,1H), 3.57(dd,J=4.0,11.0 Hz,1H).

Preparation Example 53:

Preparation of 1-(4-morpholino)-3-methyl-branched isostearyloxy-2-propanol (IIh-9):

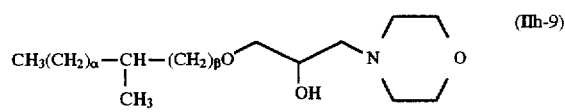
(IIh-9)

(in the formula, α and β denote numbers satisfying the following relationship: α+β=11–17, α=4–10, β=5–11, and having a distribution that the peaks of α and β are 7 and 8, respectively.)

A 200-ml eggplant type flask equipped with a stirrer was charged with 9.17 g (0.10 mol) of morpholine, 32.6 g (99.8 mmol) of methyl-branched isostearyl glycidyl ether and 6.40 g of ethanol, and the contents were heated and stirred at 80° C. in a nitrogen atmosphere. After 5 hours, the reaction mixture was concentrated under reduced pressure, and the resultant residue was purified by column chromatography on silica gel, thereby obtaining 38.0 g (yield: 92%) of the title compound (IIh-9).

Colorless oil.

IR (NaCl, cm$^{-1}$): 3468, 2924, 2856, 1456, 1118.

$^1$H-NMR (CDCl$_3$, δ): 0.70–0.98(m,6H), 1.10–1.75(m, 29H), 2.28–2.72(m,6H), 3.02–3.55(m,5H), 3.60–4.02(m, 5H).

Preparation Example 54:

Preparation of 1-(N,N-dimethylamino)-3-tetradecyloxy-2-propanol (IIh-10):

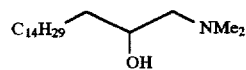
(IIh-10)

A reaction was conducted in the same manner as in Preparation Example 53 except that an aqueous solution of dimethylamine and tetradecyl glycidyl ether were used in place of morpholine and methyl-branched isostearyl glycidyl ether, respectively, in Preparation Example 53, thereby obtaining an amine derivative (IIh-10).

Colorless solid.

Melting point: 38.5°–39.4° C.

IR (NaCl, cm$^{-1}$): 3428, 2928, 2860, 2780, 1468, 1268, 1122, 1080.

$^1$H-NMR (CDCl$_3$, δ): 0.88(t,J=6.4 Hz,3H), 1.15–1.70(m, 24H), 2.05–2.60(m,2H), 2.28(s,6H), 3.30–3.50(m,4H), 3.75–3.95(m,1H).

Preparation Example 55:

Preparation of 1-amino-3-tetradecyloxy-2-propanol (IIh-11):

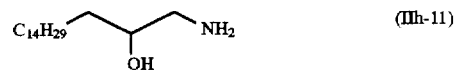
(IIh-11)

A reaction was conducted in the same manner as in Preparation Example 51 except that tetradecyl glycidyl ether was used in place of 1,2-epoxyoctadecane in Preparation Example 51, thereby synthesizing an amine derivative (IIh-11).

Colorless solid.

Melting point: 90.2°–91.1° C.

IR (NaCl, cm$^{-1}$): 3400, 2920, 2852, 1604, 1428, 1364, 1118.

$^1$H-NMR (CDCl$_3$, δ): 0.84–0.94(m,3H), 1.22–1.42(m, 22H), 1.45–1.65(m,2H), 1.65–1.90(br,3H), 2.65–2.88(m, 2H), 3.34–3.48(m,4H), 3.64–3.76(m,1H).

Preparation Example 56:

Preparation of N-(3-amino-2-hydroxypropyl)-12-hydroxydodecanamide (IIh-12):

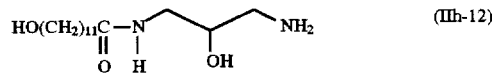
(IIh-12)

A 100-ml two-necked flask equipped with a stirrer and dropping funnel was charged with 9.39 g (104 mmol) of 1,3-diamino-2-propanol and 0.047 g (0.87 mmol) of sodium methoxide. While heating and stirring the contents at 80° C. in an N$_2$ atmosphere, a THF solution of 4.00 g (17.4 mmol) of methyl 12-hydroxydodecanate was added dropwise over 2.5 hours. Precipitate formed was washed with water and recrystallized from ethyl acetate-methanol (4:1 v/v), thereby obtaining 3.80 g (yield: 75%) of the title compound (IIh-12) as colorless powder.

Colorless solid.

Melting point: 118.7°–119.2° C.

IR (KBr, cm$^{-1}$): 3304, 2920, 2854, 1638, 1548, 1467, 1437, 1062.

$^1$H-NMR (CD$_3$OD, δ): 1.21–1.59(m,18H), 2.19(t,J=7.5 Hz,2H), 2.53(dd,J=7.5,13.2 Hz,1H), 2.63(dd,J=4.5,13.2 Hz,1H), 3.20–3.24(m,2H), 3.38–3.77(m,2H), 3.53(t,J=6.5 Hz,2H).

Example 85

Inhibitory effect of the amine derivatives on DNA synthesis of epidermic keratinocyte:

(1) Method:

a) Culture of human epidermic keratinocyte:

Human normal keratinocytes (trade name: Epipack) commercially available from Kurabo Industries Ltd. were purchased and used as keratinocytes. Incidentally, a medium for human normal keratinocytes (trade name: K-GM) commercially available from the said firm was used in the maintenance and subculture of the cells.

b) Determination of DNA synthesis (thymidine incorporation):

Keratinocytes cultured in a vegetative state in a 24-well plate were used. A medium in each well was first removed by suction to add 450 µl of K-GM, to which no pituitary gland extract was added, to the well, thereby making a medium exchange. Thereafter, each of the amine derivatives (IIh-1)–(IIh-12) obtained in the above synthesis examples was added thereto. Further, 0.2 µCi/ml of [$^3$H] thymidine was subsequently added to incubate the culture for 4 hours. After the supernatant was then removed by suction, and the well was washed 3 times with PBS(−), 500 µl of 2N NaOH were added. After the culture was incubated at 37° C. for 10 minutes, an equiamount of 2N HCl was added to neutralize the culture, and 4 ml of 10% trichloroacetic acid chilled with ice water were added, followed by leaving at rest for 30 minutes.

Precipitate was collected on a glass filter and then washed 3 times with 3 ml of 10% trichloroacetic acid chilled with ice water. The glass filter was washed further once with 3 ml of ethanol chilled with ice water and then air-dried to measure its radioactivity by a liquid scintillation counter, thereby calculating the thymidine incorporation into the cells.

(2) Result:

The relative amounts of the [$^3$H] thymidine incorporated at the time each of the amine derivatives (IIh-1) to (IIh-12) has been added in amounts of 10 µM and 100 µM are shown in Table 25.

TABLE 25

| Amine derivative | Relative amount of [$^3$H] thymidine incorporated (%)* | |
|---|---|---|
| | 10 µM | 100 µM |
| (IIh-1) | 41.7 | 13.0 |
| (IIh-2) | 24.3 | 1.6 |
| (IIh-3) | 29.6 | 1.5 |
| (IIh-4) | 21.0 | 2.0 |
| (IIh-5) | 26.2 | 4.6 |
| (IIh-6) | 1.9 | 1.6 |
| (IIh-7) | 72.8 | 1.5 |
| (IIh-8) | 38.2 | 10.1 |
| (IIh-9) | 72.1 | 25.1 |
| (IIh-10) | 10.7 | 0.8 |
| (IIh-11) | 8.1 | 6.6 |
| (IIh-12) | 7.1 | 1.4 |

*: Indicating the relative value where a control is assumed to be 100%.

It was apparent from Table 25 that the thymidine incorporation is markedly reduced by the addition of the amine derivatives, namely, that the DNA synthesis of the human epidermic keratinocytes is inhibited. Besides, the human epidermic keratinocytes treated under the same conditions as described above were observed on the fourth day. As a result, it was found that most of the cells lead to insoluble membrane (cornified envelope), i.e., become keratinized. It is understood from this fact that the amine derivatives according to the present invention are active in facilitating the keratinization of epidermis.

Example 86

Effect of the amine derivatives on wrinkles formed on hairless mice by exposure to UVB:

(1) Hairless mice (HR/ICR, aged 9 weeks at the beginning of the experiment) were each exposed to UVB 3 times a week by using 6 Toshiba healthy lamps, 20SE. The amount of energy was measured by means of a UV-Radiometer UVR-305/365D manufactured by TOKYO OPTICAL K.K. The dose upon one exposure was determined to be 1 MED or less, i.e., 65 mj in an amount of energy of 0.28 mM/cm$^2$. The exposure was effected for 20 weeks. After confirming the fact that the mice had got wrinkles at their backs, they were divided into groups each consisting of 8 mice. Ethanol solutions separately containing the amine derivatives (the samples tested are shown in Table 26) in a concentration of 0.025% were applied 5 times a week to their corresponding groups of mice for 6 weeks in a dose of 80 µl. As a control, ethanol alone was applied in a dose of 80 µl like the samples.

After completion of the application, the degree of wrinkles was visually observed to rank the samples in accordance with the following standard (wrinkle index). The results are shown in Table 26.

(Wrinkle index)

1: Wrinkles were completely removed;
2: Wrinkles were scarcely observed;
3: Wrinkles were somewhat observed;
4: Wrinkles were observed to a great extent.

(2) In order to further analyze the particulars of wrinkles, skin replicas of the size of 1 cm$^2$ in diameter were gathered from 3 portions of the back in each of the mice using a Hydrophilic Exaflex hydrophilic vinylsilicone impression material. Each of these replicas was held horizontally and illuminated at an angle of 30 degrees from the horizontal direction, thereby finding the proportion of shadows of the wrinkles as an area percent by means of an image analyzer. The results are shown collectively in Table 26.

TABLE 26

| Amine derivative | Wrinkle index | Area percent by image analysis (%) |
|---|---|---|
| Control | 3.75 ± 0.09 | 6.42 ± 0.63 |
| (IIh-1) | 3.51 ± 0.24 | 4.86 ± 0.39 |
| (IIh-3) | 3.33 ± 0.21 | 4.29 ± 0.31 |
| (IIh-5) | 3.25 ± 0.28 | 4.04 ± 0.34 |
| (IIh-7) | 3.15 ± 0.19 | 3.73 ± 0.29 |
| (IIh-8) | 3.20 ± 0.27 | 3.88 ± 0.29 |
| (IIh-9) | 3.19 ± 0.20 | 3.85 ± 0.32 |
| (IIh-10) | 3.17 ± 0.24 | 3.79 ± 0.20 |
| (IIh-12) | 3.05 ± 0.19 | 3.41 ± 0.32 |

As apparent from the result shown in Table 26, the wrinkles formed on the backs of the hairless mice can be removed by applying the amine derivatives (IIh) thereto.

Example 87

A W/O type cream having the following composition was obtained in accordance with the below-described preparation process.

| (Composition) | (wt. %) |
|---|---|
| (1) Amine derivative (IIh-3) | 0.01 |
| (2) Cholesterol | 0.5 |
| (3) Cholesteryl isostearate | 1.0 |
| (4) Polyether-modified silicone | 1.5 |
| (5) Cyclic silicone | 20.0 |
| (6) Methylphenylpolysiloxane | 2.0 |
| (7) Methylpolysiloxane | 2.0 |

| (Composition) | (wt. %) |
|---|---|
| (8) Magnesium sulfate | 0.5 |
| (9) 55% Ethanol | 5.0 |
| (10) Carboxymethylchithin (Chithin Liquid HV, product of Ichimaru Pharcos Co., Ltd.) | 0.5 |
| (11) Purified water | Balance |

(Preparation process)

Components (1)–(7) were heated to 80° C. to melt them, and the components (8)–(11) were added to the melt. The resultant mixture was intimately mixed to prepare a W/O type cream.

Example 88

An O/W type cream having the following composition was obtained in accordance with the below-described preparation process.

| (Composition) | (wt. %) |
|---|---|
| (1) Polyoxyethylene (10) hardened castor oil | 1.0 |
| (2) Sorbitan monostearate | 0.5 |
| (3) Sodium stearoylmethyltaurine | 0.5 |
| (4) Cetostearyl alcohol | 2.0 |
| (5) Stearic acid | 1.8 |
| (6) Amine derivative (IIh-6) | 0.05 |
| (7) Cholesterol | 1.5 |
| (8) Cholesteryl isostearate | 1.0 |
| (9) Neopentyl glycol dicaprate | 8.0 |
| (10) Methylpolysiloxane | 5.0 |
| (11) Glycerol | 5.0 |
| (12) Purified water | Balance |

(Preparation process)

Components (1)–(10) were heated to 80° C. to melt them, and the components (11)–(12) were added to the melt. The resultant mixture was intimately mixed to prepare an O/W type cream.

Example 89

A moisturizing sunscreen cream having the following composition was obtained in accordance with the below-described preparation process.

| (Composition) | (wt. %) |
|---|---|
| (1) Amine derivative (IIh-10) | 0.05 |
| (2) Silicon-coated zinc oxide | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methylpolysiloxane | 5.0 |
| (7) Cyclic silicone | 15.0 |
| (8) Magnesium sulfate | 1.0 |
| (9) Glycerol | 5.0 |
| (10) Purified water | Balance |

(Preparation process)

Components (1)–(7) were heated to 80° C. to melt them, and the components (8)–(10) were added to the melt. The resultant mixture was intimately mixed to prepare a moisturizing sunscreen cream.

Example 90

A pack having the following composition was obtained in accordance with the below-described preparation process.

| (Composition) | (wt. %) |
|---|---|
| (1) Amine derivative (IIh-11) hydrochloride | 0.01 |
| (2) Polyvinyl alcohol | 15.0 |
| (3) Sodium carboxymethylcellulose | 5.0 |
| (4) Propylene glycol | 3.0 |
| (5) Ethanol | 8.0 |
| (6) Purified water | Balance |
| (7) Perfume base | 0.5 |
| (8) Antiseptic, oxidizing agent | q.s. |

(Preparation process)

Components (1)–(8) were heated to 70° C. to melt them, and then cooled, thereby preparing a pack.

Example 91

An ointment having the following composition was obtained in accordance with the below-described preparation process.

| (Composition) | (wt. %) |
|---|---|
| (1) Amine derivative (IIh-12) | 0.2 |
| (2) White petrolatum | Balance |
| (3) Cholesteryl isostearate | 3.0 |
| (4) Liquid paraffin | 10.0 |
| (5) Glyceryl ether | 1.0 |
| (6) Glycerol | 10.0 |

(Preparation process)

Components (1)–(6) were heated to 80° C. to melt them, and then cooled, thereby preparing an ointment.

The dermatologic preparations according to the present invention, which were prepared in Examples 87–91, had excellent effects of preventing the occurrence of wrinkles and smoothing or removing wrinkles and moreover inhibited parakeratosis of the skin, epidermic hypertrophy and metabolic aberration of lipid and were excellent in recovery of normal functions and maintenance of homeostasis.

INDUSTRIAL APPLICABILITY

The amine derivatives (I) or (II), or the acid-added salts or quaternized products thereof and the dermatologic preparations containing such an effective component according to the present invention have excellent effects of markedly preventing the occurrence of wrinkles and smoothing or removing wrinkles, and moreover possess marked inhibitory effects on parakeratosis, dermal hypertrophy, metabolic aberration of lipid and the like caused by the influence of ultraviolet rays and/or other various factors, and besides recover the normal functions of the skin and contribute to the maintenance of homeostasis. In particular, they have excellent effects of preventing dandruff and improving the skin after sunburn.

The dermatologic preparations according to the present invention also have an effect of facilitating the keratinization of the skin and hence have an effect (beautifying effect) of accelerating the metabolism of melanin which is a causative substance of pigmentation in the skin caused by sunburn or the like, thereby improving the pigmentation in the skin.

Accordingly, their application to the skin is effective in the prevention and removal of wrinkles, improvement in keratinization and the skin, and the like.

We claim:

1. A method of smoothing or removing wrinkles, which comprises applying, to the skin, an amine derivative represented by the following general formula (I) or (II):

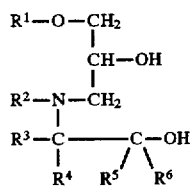 (I)

wherein $R^1$ means a hydrocarbon group having 1–3 carbon atoms or a heteroatom-containing hydrocarbon group having 1–40 carbon atoms, which may have a ring structure, and $R^2$, $R^3$, $R^4$, $R^5$ and $R^6$ are identical with or different from one another and denote individually a hydrogen atom or a hydrocarbon group having 1–20 carbon atoms, which may have at least one hydroxyl group,

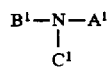 (II)

wherein $A^1$ means

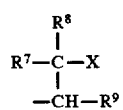

[$R^7$ means a hydrogen atom, a hydrocarbon group having 1–40 carbon atoms, which may have a hydroxyl, carboxyl, alkoxyl, alkylthio, acylamino or acyloxy group, or —$R^{10}$—Y ($R^{10}$ denotes a linear or branched hydrocarbon group having 8–40 carbon atoms, which may have a hydroxyl group, and Y is —$OR^{11}$, —$COOR^{12}$ or

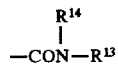

($R^{11}$, $R^{12}$, $R^{13}$ and $R^{14}$ each mean a hydrogen atom or a hydrocarbon group having 1–20 carbon atoms, which may contain an oxygen atom)), $R^8$ denotes a hydrogen atom or a hydrocarbon group having 1–40 carbon atoms, which may have a hydroxyl, carboxyl, alkoxyl, alkylthio, acylamino or acyloxy group, $R^9$ stands for a hydrogen atom, a hydrocarbon group having 1–40 carbon atoms, which may have a hydroxyl, carboxyl, alkoxyl, alkylthio, acylamino or acyloxy group, a carboxyl group, or

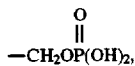

and X is a hydrogen atom, hydroxyl group or

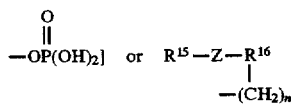

[$R^{15}$ denotes a linear, branched or cyclic hydrocarbon group having 1–40 carbon atoms, which may have a heteroatom, $R^{16}$ means a hydrocarbon group having 1–7 carbon atoms, which may have a hydroxyl or alkoxyl group or

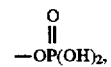

Z denotes —COO—, —O—, —S— or —$CONR^{17}$ ($R^{17}$ is a hydrogen atom or a hydrocarbon group having 1–10 carbon atoms, which may have a hydroxyl group), and n stands for an integer of 1–5]; $B^1$ denotes a hydrogen atom, a hydrocarbon group having 1–10 carbon atoms, which may have a hydroxyl group, or a nitrogen atom; and $C^1$ stands for a hydrogen atom, a hydrocarbon group having 1–10 carbon atoms, which may have a hydroxyl group, alkoxyl group, hydroxyalkyloxy group, phosphoric acid residue, carboxyl group or alkoxycarbonyl group, a nitrogen atom, or —$R^{18}$—O—X' [$R^{18}$ means a hydrocarbon group having 2–10 carbon atoms, which may have a hydroxyl group, and X' denotes a hydrogen atom or

and $B^1$ and $C^1$ may form a heterocyclic ring, which may contain an oxygen atom, together with the adjacent nitrogen atom, or an acid-added salt or quaternized product thereof.

2. The method of smoothing or removing wrinkles according to claim 1, wherein the amine derivative is represented by the following general formula (Ia):

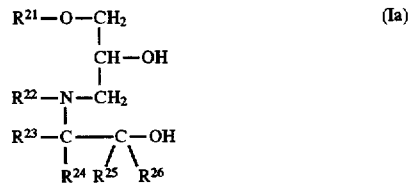 (Ia)

wherein $R^{21}$ means a linear or branched hydrocarbon group having 7–40 carbon atoms and containing a heteroatom, $R^{22}$, $R^{23}$, $R^{24}$, $R^{25}$ and $R^{26}$ are identical with or different from one another and denote individually a hydrogen atom or a hydrocarbon group having 1–10 carbon atoms, which may have one or more hydroxyl groups.

3. The method of smoothing or removing wrinkles according to claim 1, wherein the amine derivative is represented by the following general formula (Ib):

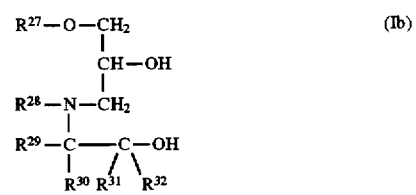 (Ib)

wherein $R^{27}$ means a hydrocarbon group having 7–40 carbon atoms, which has a ring structure and contains a heteroatom, and $R^{28}$, $R^{29}$, $R^{30}$, $R^{31}$ and $R^{32}$ are identical with or different from one another and denote individually a hydrogen atom or a hydrocarbon group having 1–10 carbon atoms, which may be substituted by a hydroxyl group.

4. The method of smoothing or removing wrinkles according to claim 1, wherein the amine derivative is represented by the following general formula (Ic):

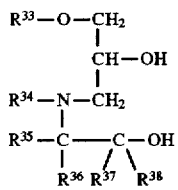
(Ic)

wherein $R^{33}$ means a hydrocarbon group having 1–3 carbon atoms or a heteroatom-containing hydrocarbon group having 1–5 carbon atoms, and $R^{34}$, $R^{35}$, $R^{36}$, $R^{37}$ and $R^{38}$ are identical with or different from one another and denote individually a hydrogen atom or a hydrocarbon group having 1–20 carbon atoms, which may be substituted by at least one hydroxyl group.

5. The method of smoothing or removing wrinkles according to claim 1, wherein the amine derivative is represented by the following general formula (IIa) or (IIb):

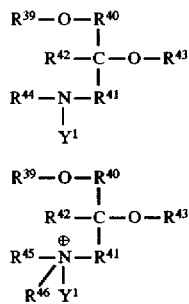
(IIa)

(IIb)

wherein $R^{39}$ means a linear, branched or cyclic hydrocarbon group having 1–40 carbon atoms, which may contain a heteroatom, $R^{40}$ and $R^{41}$ are identical with or different from each other and denote individually a divalent hydrocarbon group having 1–3 carbon atoms, $R^{42}$ represents a hydrogen atom or a hydrocarbon group having 1–3 carbon atoms, $R^{43}$ stands for a hydrogen atom or a hydrocarbon group having 1–3 carbon atoms or

$$\underset{\|}{\overset{O}{-P(OH)_2,}}$$

$R^{44}$ is a hydrogen atom or a hydrocarbon group having 1–10 carbon atoms, which may have one or more hydroxyl groups, $R^{45}$ and $R^{46}$ are identical with or different from each other and represent individually a hydrocarbon group having 1–3 carbon atoms, which may have 1–3 hydroxyl groups, and $Y^1$ means a hydrocarbon group having 1–10 carbon atoms and containing one or more groups selected from the group consisting of a hydroxyl group, alkoxyl group, hydroxyalkyloxy group, phosphoric acid residue, carboxyl group and alkoxycarbonyl group, with the proviso that in the formula (IIa), the case where both $R^{40}$ and $R^{41}$ are —$CH_2$—, both $R^{42}$ and $R^{43}$ are hydrogen atoms, and $Y^1$ is the following formula:

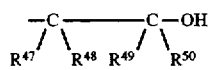

in which $R^{47}$, $R^{48}$, $R^{49}$ and $R^{50}$ have the same meaning as $R^{44}$, is excluded.

6. The method of smoothing or removing wrinkles according to claim 1, wherein the amine derivative is represented by the following general formula (IIc):

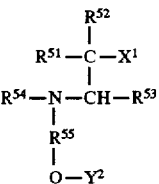
(IIc)

wherein $R^{51}$ means a hydrogen atom or a linear, branched or cyclic hydrocarbon group having 1–40 carbon atoms, $R^{52}$ denotes a hydrogen atom or a hydrocarbon group having 1–5 carbon atoms, which may have one or more hydroxyl groups, $R^{53}$ stands for a hydrogen atom or a hydrocarbon group having 1–22 carbon atoms, which may have one or more hydroxyl or alkoxyl groups, $R^{54}$ represents a hydrogen atom or a hydrocarbon group having 1–7 carbon atoms, which may have one or more hydroxyl groups, $R^{55}$ means a hydrogen atom or a hydrocarbon group having 2–6 carbon atoms, which may have one or more hydroxyl groups, $X^1$ denotes a hydrogen atom, hydroxyl group or

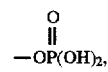
$$\underset{\|}{\overset{O}{-OP(OH)_2,}}$$

and $Y^2$ represents a hydrogen atom or

$$\underset{\|}{\overset{O}{-P(OH)_2.}}$$

7. The method of smoothing or removing wrinkles according to claim 1, wherein the amine derivative is represented by the following general formula (IId):

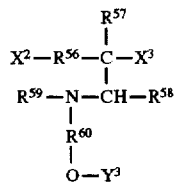
(IId)

wherein $R^{56}$ means a linear or branched hydrocarbon group having 8–40 carbon atoms, which may have a hydroxyl group, $R^{57}$, $R^{58}$ and $R^{59}$ are identical with or different from each other and denote individually denotes a hydrogen atom or a hydrocarbon group having 1–7 carbon atoms, which may have one or more hydroxyl groups, $R^{60}$ stands for a hydrocarbon group having 2–6 carbon atoms, which may have one or more hydroxyl or alkoxyl groups, $X^2$ is —$OR^{61}$, —$CO_2R^{62}$ or

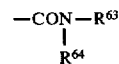

($R^{61}$, $R^{62}$, $R^{63}$ and $R^{64}$ are identical with or different from one another and denote individually a hydrogen atom or a hydrocarbon group having 1–20 carbon atoms, which may contain an oxygen atom), and $Y^3$ represents a hydrogen atom or a hydroxyl group.

8. The method of smoothing or removing wrinkles according to claim 1, wherein the amine derivative is represented by the following general formula (IIe):

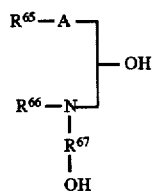

(IIe)

wherein $R^{65}$ means a linear, branched or cyclic hydrocarbon group having 1–40 carbon atoms, which may contain a heteroatom, $R^{66}$ and $R^{68}$ are identical with or different from each other and denote individually a hydrogen atom or a hydrocarbon group having 1–10 carbon atoms, which may have a hydroxyl group, $R^{67}$ stands for a hydrocarbon group having 2–10 carbon atoms, which may be substituted by a hydroxyl group, and A represents —$CO_2$—, —S— or

—CON—.

9. The method of smoothing or removing wrinkles according to claim 1, wherein the amine derivative is represented by the following general formula (IIf):

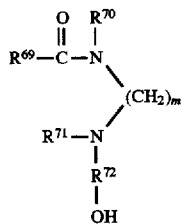

(IIf)

wherein $R^{69}$ means a linear, branched or cyclic hydrocarbon group having 1–40 carbon atoms, which may contain a heteroatom, $R^{70}$ and $R^{71}$ are identical with or different from each other and denote individually a hydrogen atom or a hydrocarbon group having 1–10 carbon atoms, which may have one or more hydroxyl groups, $R^{72}$ represents a hydrocarbon group having 2–6 carbon atoms, which may have one or more hydroxyl groups, and m stands for an integer of 2–6.

10. The method of smoothing or removing wrinkles according to claim 1, wherein the amine derivative is represented by the following general formula (IIg):

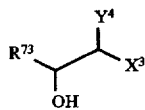

(IIg)

wherein $R^{73}$ means a linear, branched or cyclic hydrocarbon group having 1–40 carbon atoms, which may have a hydroxyl group, $X^3$ denotes —$CH_2OH$, —$CO_2H$ or —$CH_2OP(OH)_2$, and
$\overset{\|}{O}$ $Y^4$ stands for —$NH_2$, —$NHCH_3$, —$N(CH_3)_2$ or —$\overset{\oplus}{N}(CH_3)_3$.

11. The method of smoothing or removing wrinkles according to claim 1, wherein the amine derivative is represented by the following general formula (IIh):

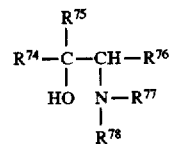

(IIh)

wherein $R^{74}$ and $R^{75}$ mean individually a hydrogen atom or a hydrocarbon group having 1–40 carbon atoms, which may have a hydroxyl, carboxyl, alkoxyl, alkylthio, acylamino or acyloxy group, $R^{76}$ denotes a hydrogen atom or a hydrocarbon group having 1–40 carbon atoms, which may have an alkoxyl, alkylthio, acylamino or acyloxy group, or a hydrocarbon group having 1–40 carbon atoms, which may have a hydroxyl or carboxyl group, with the proviso that the total number of carbon atoms contained in $R^{74}$, $R^{75}$ and $R^{76}$ is at least 5, and $R^{77}$ and $R^{78}$ stand individually for a hydrogen atom, a hydrocarbon group having 1–10 carbon atoms or a nitrogen atom, or may form a heterocyclic ring, which may contain an oxygen atom, together with the adjacent nitrogen atom.

12. A method of improving keratinization, which comprises applying, to the skin, an amine derivative represented by the following general formula (I) or (II):

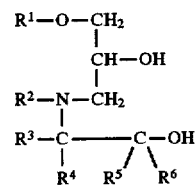

(I)

wherein $R^1$ means a hydrocarbon group having 1–3 carbon atoms or a heteroatom-containing hydrocarbon group having 1–40 carbon atoms, which may have a ring structure, and $R^2$, $R^3$, $R^4$, $R^5$ and $R^6$ are identical with or different from one another and denote individually a hydrogen atom or a hydrocarbon group having 1–20 carbon atoms, which may have at least one hydroxyl group,

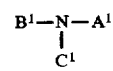

(II)

wherein $A^1$ means

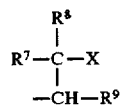

[$R^7$ means a hydrogen atom, a hydrocarbon group having 1–40 carbon atoms, which may have a hydroxyl, carboxyl, alkoxyl, alkylthio, acylamino or acyloxy group, or —$R^{10}$—Y ($R^{10}$ denotes a linear or branched hydrocarbon group having 8–40 carbon atoms, which may have a hydroxyl group, and Y is —$OR^{11}$, —$COOR^{12}$ or

($R^{11}$, $R^{12}$, $R^{13}$ and $R^{14}$ each mean a hydrogen atom or a hydrocarbon group having 1–20 carbon atoms, which may contain an oxygen atom)), $R^8$ denotes a hydrogen atom or a hydrocarbon group having 1–40 carbon atoms, which may have a hydroxyl, carboxyl, alkoxyl, alkylthio, acylamino or acyloxy group, $R^9$ stands for a hydrogen atom, a hydrocarbon group having 1–40 carbon atoms, which may have a hydroxyl, carboxyl, alkoxyl, alkylthio, acylamino or acyloxy group, a carboxyl group, or

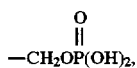

and X is a hydrogen atom, hydroxyl group or

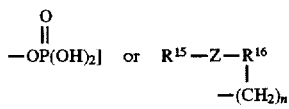

[$R^{15}$ denotes a linear, branched or cyclic hydrocarbon group having 1–40 carbon atoms, which may have a heteroatom, $R^{16}$ means a hydrocarbon group having 1–7 carbon atoms, which may have a hydroxyl or alkoxyl group or

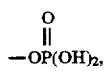

Z denotes —COO—, —O—, —S— or —CONR$^{17}$ ($R^{17}$ is a hydrogen atom or a hydrocarbon group having 1–10 carbon atoms, which may have a hydroxyl group), and n stands for an integer of 1–5]; $B^1$ denotes a hydrogen atom, a hydrocarbon group having 1–10 carbon atoms, which may have a hydroxyl group, or a nitrogen atom; and $C^1$ stands for a hydrogen atom, a hydrocarbon group having 1–10 carbon atoms, which may have a hydroxyl group, alkoxyl group, hydroxyalkyloxy group, phosphoric acid residue, carboxyl group or alkoxycarbonyl group, a nitrogen atom, or —$R^{18}$—O—X' [$R^{18}$ means a hydrocarbon group having 2–10 carbon atoms, which may have a hydroxyl group, and X' denotes a hydrogen atom or

and $B^1$ and $C^1$ may form a heterocyclic ring, which may contain an oxygen atom, together with the adjacent nitrogen atom, or an acid-added salt or quaternized product thereof.

13. A dermatologic preparation comprising an amine derivative represented by the following general formula (I) or (II):

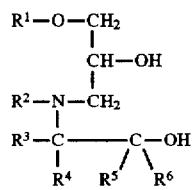

wherein $R^1$ means a hydrocarbon group having 1–3 carbon atoms or a heteroatom-containing hydrocarbon group having 1–40 carbon atoms, which may have a ring structure, and $R^2$, $R^3$, $R^4$, $R^5$ and $R^6$ are identical with or different from one another and denote individually a hydrogen atom or a hydrocarbon group having 1–20 carbon atoms, which may have at least one hydroxyl group,

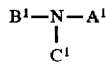

wherein $A^1$ means

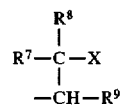

[$R^7$ means a hydrogen atom, a hydrocarbon group having 1–40 carbon atoms, which may have a hydroxyl, carboxyl, alkoxyl, alkylthio, acylamino or acyloxy group, or —$R^{10}$—Y ($R^{10}$ denotes a linear or branched hydrocarbon group having 8–40 carbon atoms, which may have a hydroxyl group, and Y is —OR$^{11}$, —COOR$^{12}$ or

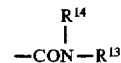

($R^{11}$, $R^{12}$, $R^{13}$ and $R^{14}$ each mean a hydrogen atom or a hydrocarbon group having 1–20 carbon atoms, which may contain an oxygen atom)), $R^8$ denotes a hydrogen atom or a hydrocarbon group having 1–40 carbon atoms, which may have a hydroxyl, carboxyl, alkoxyl, alkylthio, acylamino or acyloxy group, $R^9$ stands for a hydrogen atom, a hydrocarbon group having 1–40 carbon atoms, which may have a hydroxyl, carboxyl, alkoxyl, alkylthio, acylamino or acyloxy group, a carboxyl group, or

and X is a hydrogen atom, hydroxyl group or

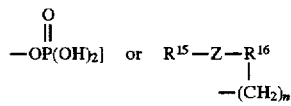

[$R^{15}$ denotes a linear, branched or cyclic hydrocarbon group having 1–40 carbon atoms, which may have a heteroatom, $R^{16}$ means a hydrocarbon group having 1–7 carbon atoms, which may have a hydroxyl or alkoxyl group or

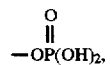

Z denotes —COO—, —O—, —S— or —CONR$^{17}$ ($R^{17}$ is a hydrogen atom or a hydrocarbon group having 1–10 carbon atoms, which may have a hydroxyl group), and n stands for an integer of 1–5]; $B^1$ denotes a hydrogen atom, a hydrocarbon group having 1–10 carbon atoms, which may have a hydroxyl group, or a nitrogen atom; and $C^1$ stands for a hydrogen atom, a hydrocarbon group having 1–10 carbon atoms, which may have a hydroxyl group, alkoxyl group, hydroxyalkyloxy group, phosphoric acid residue, carboxyl group or alkoxycarbonyl group, a nitrogen atom, or —$R^{18}$—O—X' [$R^{18}$ means a hydrocarbon group having 2–10 carbon atoms, which may have a hydroxyl group, and X' denotes a hydrogen atom or

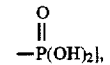

and $B^1$ and $C^1$ may form a heterocyclic ring, which may contain an oxygen atom, together with the adjacent nitrogen atom, or an acid-added salt or quaternized product thereof.

14. An amine derivative represented by the following general formula (Ia'):

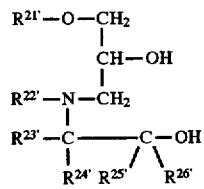 (Ia')

wherein $R^{21'}$ means a hydrocarbon group having 8–22 carbon atoms and a hydroxyl or alkoxyl group on its carbon chain, $R^{22'}$, $R^{23'}$ and $R^{24'}$ are identical with or different from one another and denote individually a hydrogen atom, or a methyl, hydroxymethyl or 2-hydroxyethyl group, and $R^{25'}$ and $R^{26'}$ stand for a hydrogen atom, or an acid-added salt thereof.

15. An amine derivative represented by the following general formula (Ib'):

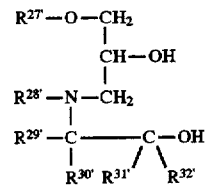 (Ib')

wherein $R^{27'}$ means a tocopheryl or 9,10-(isopropylidenedioxy)octadecyl group, and $R^{28'}$, $R^{29'}$, $R^{30'}$, $R^{31'}$ and $R^{32'}$ are identical with or different from one another and denote individually a hydrogen atom or a hydrocarbon group having 1–10 carbon atoms, which may be substituted by a hydroxyl group, or an acid-added salt thereof.

16. An amine derivative represented by the following general formula (IId'):

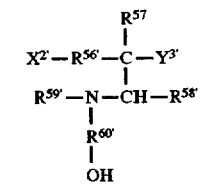 (IId')

wherein $R^{56'}$ means a linear or branched hydrocarbon group having 8–40 carbon atoms, $R^{57'}$, $R^{58'}$ and $R^{59'}$ are identical with or different from one another and denote individually a hydrogen atom or a hydrocarbon group having 1–7 carbon atoms, which may have one or more hydroxyl groups, $R^{60'}$ is a hydrocarbon group having 2–6 carbon atoms, which may have one or more hydroxyl groups, $X^{2'}$ stands for $-OR^{61'}$, $-CO_2OR^{62'}$ or

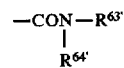

($R^{61'}$, $R^{62'}$, $R^{63'}$ and $R^{64'}$ are identical with or different from one another and denote individually a hydrogen atom or a hydrocarbon group having 1–20 carbon atoms, which may contain an oxygen atom), and $Y^{3'}$ means a hydroxyl group, or an acid-added salt thereof.

17. An amine derivative represented by the following general formula (IId''):

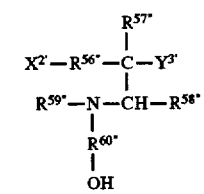 (IId'')

wherein $R^{56''}$ means an undecamethylene, dodecamethylene, tridecamethylene or tetradecamethylene group, $R^{57''}$, $R^{58''}$ and $R^{59''}$ denote individually a hydrocarbon group having 1–7 carbon atoms, which may have one or more hydroxyl groups, $R^{60''}$ is a hydrocarbon group having 2–6 carbon atoms, which may have one or more hydroxyl groups, $X^{2'}$ stands for a hydroxyl group, and $Y^{3'}$ means a hydrogen atom, or an acid-added salt thereof.

18. An amine derivative represented by the following general formula (IIe'):

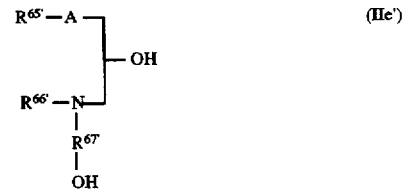 (IIe')

wherein $R^{65'}$ means a linear or branched hydrocarbon group having 7–24 carbon atoms and containing an oxygen atom, $R^{66'}$ and $R^{68'}$ denote individually a hydrogen atom or a hydrocarbon group having 1–10 carbon atoms, which may be substituted by a hydroxyl group, $R^{67'}$ stands for a hydrocarbon group having 2–10 carbon atoms, which may be substituted by a hydroxyl group, and A represents $-CO_2-$,

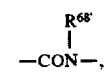

or an acid-added salt thereof.

19. The amine derivative of claim 14, which is a member selected from the group consisting of

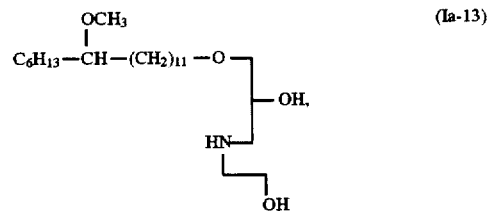 (Ia-13)

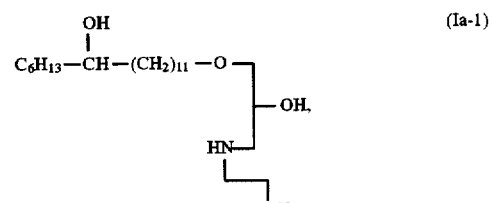 (Ia-1)

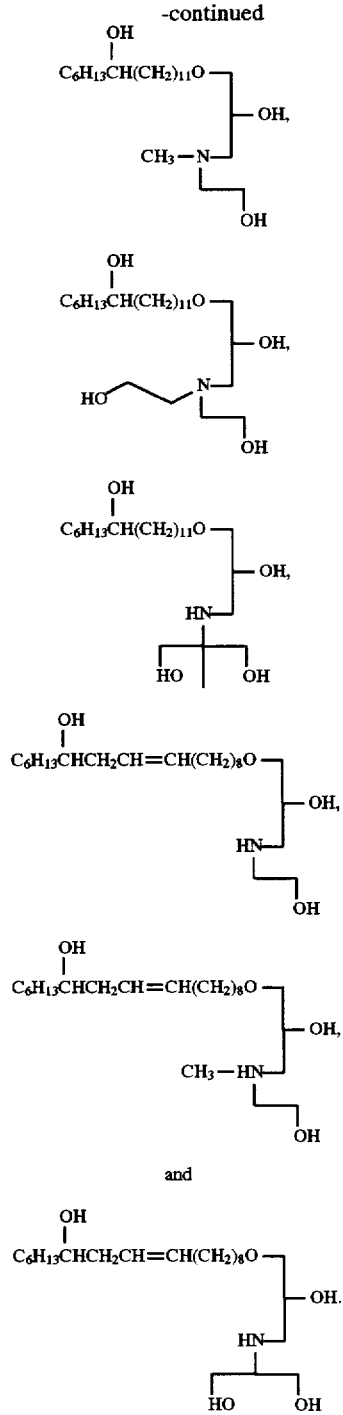
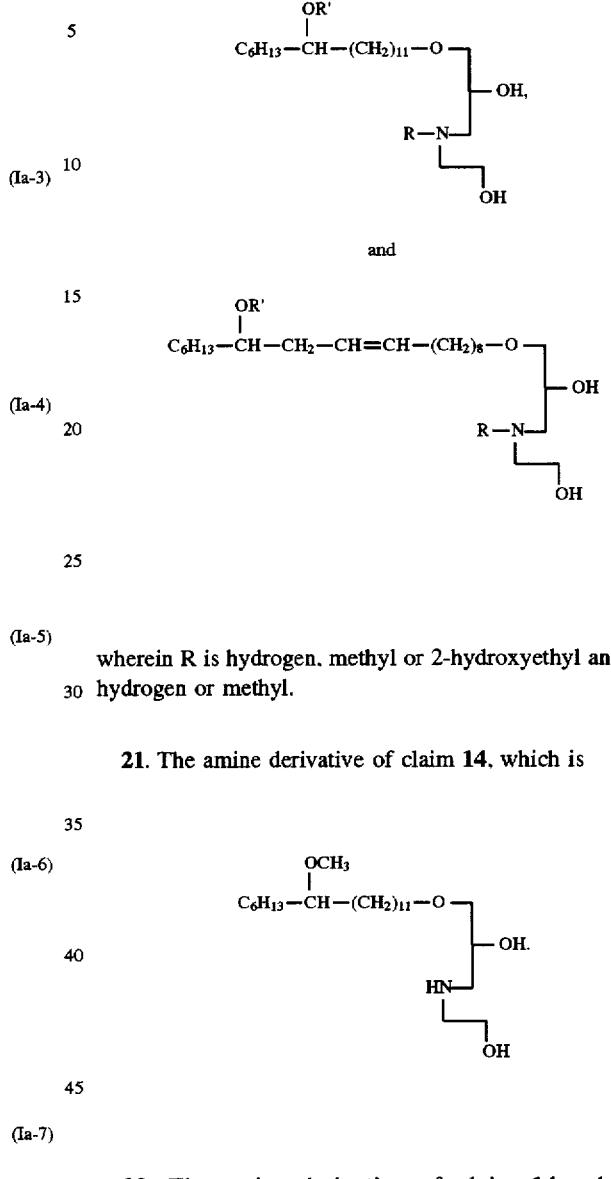
wherein R is hydrogen, methyl or 2-hydroxyethyl and R' is hydrogen or methyl.
21. The amine derivative of claim 14, which is
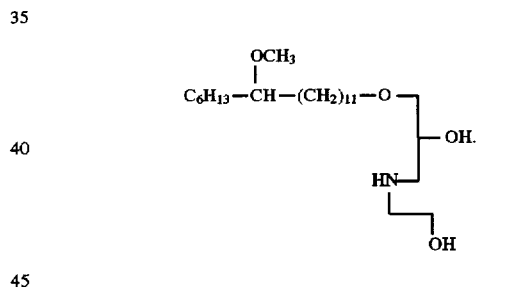
22. The amine derivative of claim 14, which is 1-(2hydroxyethylamino)-3-(12-hydroxyoctadecyloxy)-2-propanol.
* * * * *

UNITED STATES PATENT AND TRADEMARK OFFICE
CERTIFICATE OF CORRECTION

PATENT NO. : 5,723,497
DATED : March 3, 1998
INVENTOR(S) : Yukihiro OHASHI et al It is certified that error appears in the above-identified patent and that said Letters Patent is hereby corrected as shown below:

Column 110, line 38, "$-CO_2-$," should read -- $-CO_2-$, $-S-$ --.

Signed and Sealed this

Tenth Day of November 1998

Attest:

BRUCE LEHMAN

Attesting Officer

Commissioner of Patents and Trademarks